US011915105B2

(12) United States Patent
Steingrimsson et al.

(10) Patent No.: US 11,915,105 B2
(45) Date of Patent: Feb. 27, 2024

(54) MACHINE LEARNING TO ACCELERATE ALLOY DESIGN

(71) Applicant: Baldur Andrew Steingrimsson, Hillsboro, OR (US)

(72) Inventors: Baldur Andrew Steingrimsson, Hillsboro, OR (US); Peter K Liaw, Knoxville, TN (US); Xuesong Fan, Knoxville, TN (US); Anand A Kulkarni, Charlotte, NC (US); Duckbong Kim, Cookeville, TN (US)

(73) Assignee: IMAGARS LLC, Wilsonville, OR (US)

( * ) Notice: Subject to any disclaimer, the term of this patent is extended or adjusted under 35 U.S.C. 154(b) by 1059 days.

(21) Appl. No.: 16/782,829

(22) Filed: Feb. 5, 2020

(65) Prior Publication Data

US 2020/0257933 A1  Aug. 13, 2020

Related U.S. Application Data

(60) Provisional application No. 62/801,280, filed on Feb. 5, 2019.

(51) Int. Cl.
*G06N 20/00* (2019.01)
*G06F 30/27* (2020.01)
(Continued)

(52) U.S. Cl.
CPC .......... *G06N 20/00* (2019.01); *B22F 10/366* (2021.01); *B22F 10/368* (2021.01); *B22F 10/80* (2021.01);
(Continued)

(58) Field of Classification Search
None
See application file for complete search history.

(56) References Cited

U.S. PATENT DOCUMENTS 10,495,590 B2   12/2019   Vecchio et al.
2016/0034614 A1  2/2016   Wang et al.
(Continued)

FOREIGN PATENT DOCUMENTS

KR   20040008381 A  *  1/2004

OTHER PUBLICATIONS

U.S. Appl. No. 14/567,516, filed Dec. 11, 2014, B. Steingrimsson.
(Continued)

*Primary Examiner* — Roy Y Yi
*Assistant Examiner* — Geoffrey T Evans

(57) ABSTRACT

This invention presents an innovative framework for the application of machine learning for identification of alloys or composites with desired properties of interest. For each output property of interest, we identify the corresponding driving (input) factors. These input factors may include the material composition, heat treatment, process, microstructure, temperature, strain rate, environment or testing mode. Our framework assumes selection of optimization technique suitable for the application at hand and data available, starting with simple linear, or quadratic, regression analysis. We present a physics-based model for predicting the ultimate tensile strength, a model that accounts for physical dependencies, and factors in the underlying physics as a priori information. In case an artificial neural network is deemed suitable, we suggest employing custom kernel functions consistent with the underlying physics, for the purpose of attaining tighter coupling, better prediction, and extracting the most out of the—usually limited—input data available.

21 Claims, 40 Drawing Sheets

(51) Int. Cl.
| | | |
|---|---|---|
| *G16C 20/30* | (2019.01) | |
| *G06N 7/01* | (2023.01) | |
| *B29C 64/393* | (2017.01) | |
| *B29C 64/153* | (2017.01) | |
| *B29C 64/268* | (2017.01) | |
| *B33Y 50/02* | (2015.01) | |
| *G16C 20/70* | (2019.01) | |
| *G16C 60/00* | (2019.01) | |
| *B22F 12/45* | (2021.01) | |
| *B22F 12/90* | (2021.01) | |
| *B22F 10/366* | (2021.01) | |
| *B22F 10/368* | (2021.01) | |
| *B22F 10/80* | (2021.01) | |
| *B22F 10/85* | (2021.01) | |
| *G06F 18/211* | (2023.01) | |
| *G06F 18/213* | (2023.01) | |
| *B33Y 70/10* | (2020.01) | |
| *B33Y 10/00* | (2015.01) | |
| *B33Y 30/00* | (2015.01) | |
| *G06F 119/08* | (2020.01) | |
| *G06F 113/10* | (2020.01) | |
| *B22F 10/22* | (2021.01) | |
| *B22F 10/25* | (2021.01) | |
| *B22F 10/28* | (2021.01) | |
| *B22F 10/36* | (2021.01) | |

(52) U.S. Cl.
CPC .............. *B22F 10/85* (2021.01); *B22F 12/45* (2021.01); *B22F 12/90* (2021.01); *B29C 64/153* (2017.08); *B29C 64/268* (2017.08); *B29C 64/393* (2017.08); *B33Y 50/02* (2014.12); *G06F 18/211* (2023.01); *G06F 18/213* (2023.01); *G06F 30/27* (2020.01); *G06N 7/01* (2023.01); *G16C 20/30* (2019.02); *G16C 20/70* (2019.02); *G16C 60/00* (2019.02); *B22F 10/22* (2021.01); *B22F 10/25* (2021.01); *B22F 10/28* (2021.01); *B22F 10/36* (2021.01); *B33Y 10/00* (2014.12); *B33Y 30/00* (2014.12); *B33Y 70/10* (2020.01); *G06F 2113/10* (2020.01); *G06F 2119/08* (2020.01)

(56) References Cited

U.S. PATENT DOCUMENTS

2019/0337232 A1   11/2019  Narra et al.
2020/0210635 A1*  7/2020   Washburn .............. G06N 3/044

OTHER PUBLICATIONS

U.S. Appl. No. 15/613,183, filed Jun. 3, 2017, B. Steingrimsson, Yi.
U.S. Appl. No. 16/182,389, filed Jun. 8, 2018, Steingrimsson, Yi, Jones, Kisialiou.

\* cited by examiner

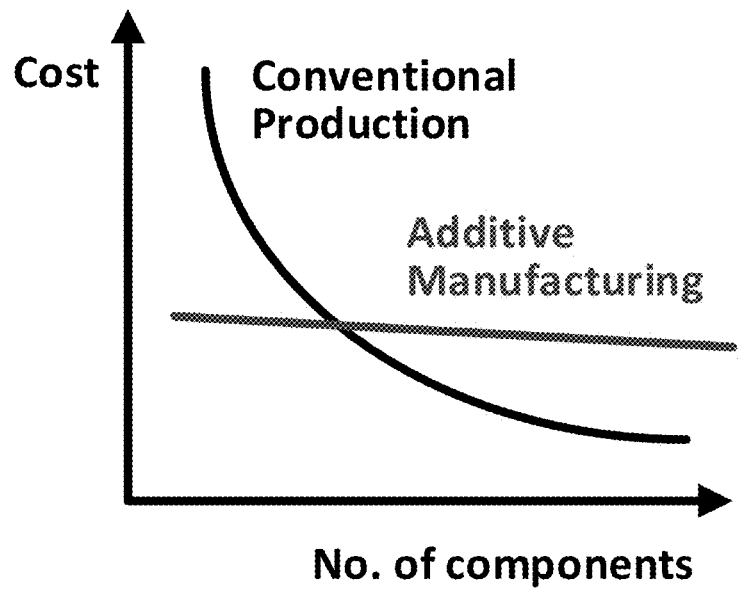
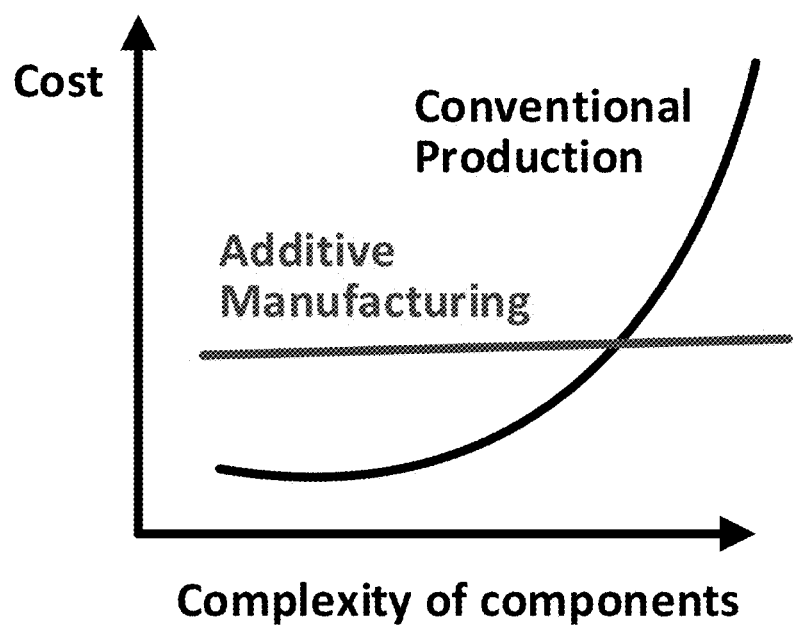
FIG. 9

Measured Composition:
(highest UTS measured, per original database)
Al0.5Mo0.5NbTa0.5TiZr

| Composition Yielding Highest UTS |||||
|---|---|---|---|---|
| Al0.5Mo0.5Nb Ta0.5TiZr | UTS measured | | a (Weights) | UTS predicted |
| Offset | 0 | | 0 | 2,169 MPa |
| %Al | 11.1% | | 9.76% | |
| %Mo | 11.1% | | 28.16% | |
| %Nb | 22.2% | | 37.94% | |
| %Ti | 22.2% | 2,468 MPa | -10.10% | |
| %V | 0.0% | | 9.70% | |
| %Ta | 11.1% | | 25.69% | |
| %Zr | 22.2% | | 37.97 | |
| %Hf | 0.0% | | -23.00 | |

| Composition Predicted | A (Weights) | UTS predicted |
|---|---|---|
| Offset | 0 | 0 |
| %Al | 11.1% | 9.76% |
| %Mo | 11.1% | 28.16% |
| %Nb | 27.2% | 37.94% |
| %Ti | 12.2% | -10.10% | 2,648 MPa
| %V | 0.0% | 9.70% |
| %Ta | 11.1% | 25.69% |
| %Zr | 27.2% | 37.97 |
| %Hf | 0.0% | -23.00 |

| Composition Predicted | a (Weights) | UTS predicted |
|---|---|---|
| Offset | 0 | 0 |
| %Al | 11.1% | 9.76% |
| %Mo | 11.1% | 28.16% |
| %Nb | 32.2% | 37.94% |
| %Ti | 2.2% | -10.10% | 3,128 MPa
| %V | 0.0% | 9.70% |
| %Ta | 11.1% | 25.69% |
| %Zr | 32.2% | 37.97 |
| %Hf | 0.0% | -23.00 |

Predicted Composition:
$Al_{0.5}Mo_{0.5}Nb_{1.5}Ta_{0.5}Zr_{1.5}$

FIG. 23

Measured Composition:
(highest UTS measured, per original database)
Al0.5Mo0.5NbTa0.5TiZr

| Composition Yielding Highest UTS | | | |
|---|---|---|---|
| Al0.5Mo0.5Nb Ta0.5TiZr | UTS measured | a | UTS predicted |
| Offset | 0 | | 0 | 2,139 MPa |
| %Al | 11.1% | | 11.80 | |
| %Mo | 11.1% | | 26.38 | |
| %Nb | 22.2% | 2,460 MPa | 29.09 | |
| %Ti | 22.2% | | -1.96 | |
| %V | 0.0% | | 6.82 | |
| %Ta | 11.1% | | 21.35 | |
| %Zr | 22.2% | | 39.36 | |
| %Hf | 0.0% | | -16.20 | |
| %Cr | 0.0% | | 38.70 | |

| Composition Predicted | a (Weights) | UTS predicted |
|---|---|---|
| Offset | 0 | 0 | |
| %Al | 11.1% | 11.80 | |
| %Mo | 11.1% | 26.38 | |
| %Nb | 27.2% | 29.09 | |
| %Ti | 12.2% | -1.96 | 2,499 MPa |
| %V | 0.0% | 6.82 | |
| %Ta | 11.1% | 21.35 | |
| %Zr | 27.2% | 39.36 | |
| %Hf | 0.0% | -16.20 | |
| %Cr | 0.0% | 38.70 | |

| Composition Predicted | a (Weights) | UTS predicted |
|---|---|---|
| Offset | 0 | 0 | |
| %Al | 11.1% | 11.80 | |
| %Mo | 11.1% | 26.38 | |
| %Nb | 32.2% | 29.09 | |
| %Ti | 2.2% | -1.96 | 2,861 MPa |
| %V | 0.0% | 6.82 | |
| %Ta | 11.1% | 21.35 | |
| %Zr | 32.2% | 39.36 | |
| %Hf | 0.0% | -16.20 | |
| %Cr | 0.0% | 38.70 | |

Predicted Composition:
$Al_{0.5}Mo_{0.5}Nb_{1.5}Ta_{0.5}Zr_{1.5}$

FIG. 24

Measured Composition:
(highest UTS measured, per enhanced database)
MoNbTiV0.75Zr

| Composition Yielding Highest UTS | | | |
|---|---|---|---|
| MoNbTiV0.75Zr | UTS measured | a | UTS predicted |
| Offset | 0 | | 0 |
| %Al | 0.0% | | -5.743 |
| %Mo | 21.05% | | 56.264 |
| %Nb | 21.05% | | 46.933 |
| %Ti | 21.05% | 3,929 MPa | 0.201 |
| %V | 15.79% | | 13.451 |
| %Ta | 0.0% | | -7.781 |
| %Zr | 21.05 | | 42.231 |
| %Hf | 0.0% | | -18.991 |
| %Cr | 0.0% | | -2.472% |

UTS predicted: 3,262.1 MPa

| Composition Predicted | a (Weights) | UTS predicted |
|---|---|---|
| Offset | 0 | 0 |
| %Al | 0.0% | -5.743 |
| %Mo | 26.1% | 56.264 |
| %Nb | 26.1% | 46.933 |
| %Ti | 11.1% | 0.201 |
| %V | 15.8% | 13.451 |
| %Ta | 0.0% | -7.781 |
| %Zr | 21.1% | 42.231 |
| %Hf | 0.0% | -18.991 |
| %Cr | 0.0% | -2.472% |

UTS predicted: 3,799.3 MPa

| Composition Predicted | a (Weights) | UTS predicted |
|---|---|---|
| Offset | 0 | 0 |
| %Al | 0.0% | -5.743 |
| %Mo | 33.3% | 56.264 |
| %Nb | 33.3% | 46.933 |
| %Ti | 0.0% | 0.201 |
| %V | 0.0% | 13.451 |
| %Ta | 0.0 | -7.781 |
| %Zr | 33.3% | 42.231 |
| %Hf | 0.0% | -18.991 |
| %Cr | 0.0% | -2.472% |

UTS predicted: 4,847.1 MPa

Predicted Composition:
$Mo_{1.25}Nb_{1.25}Ti_{0.5}V_{0.75}Zr$

Predicted Composition:
$Mo_{1.25}Nb_{1.25}Ti_{0.5}V_{0.5}Zr_{1.25}$

Predicted Composition:
MoNbZr

FIG. 25

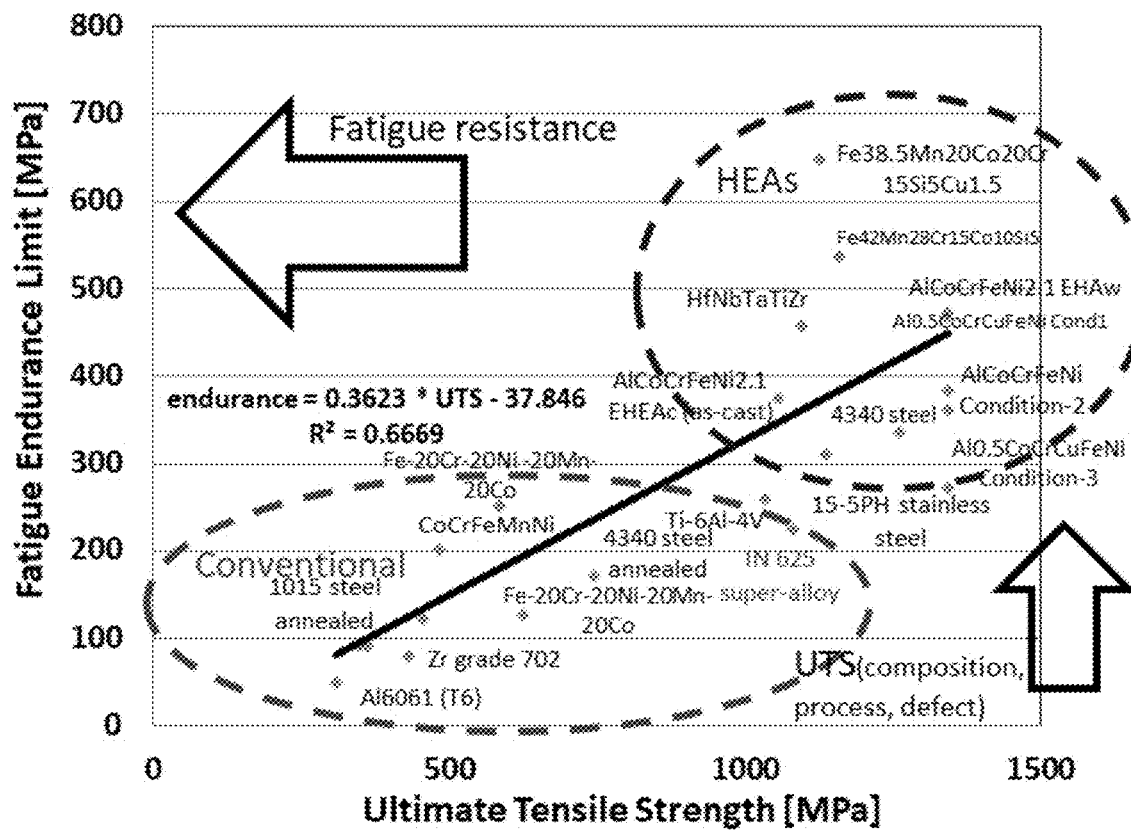
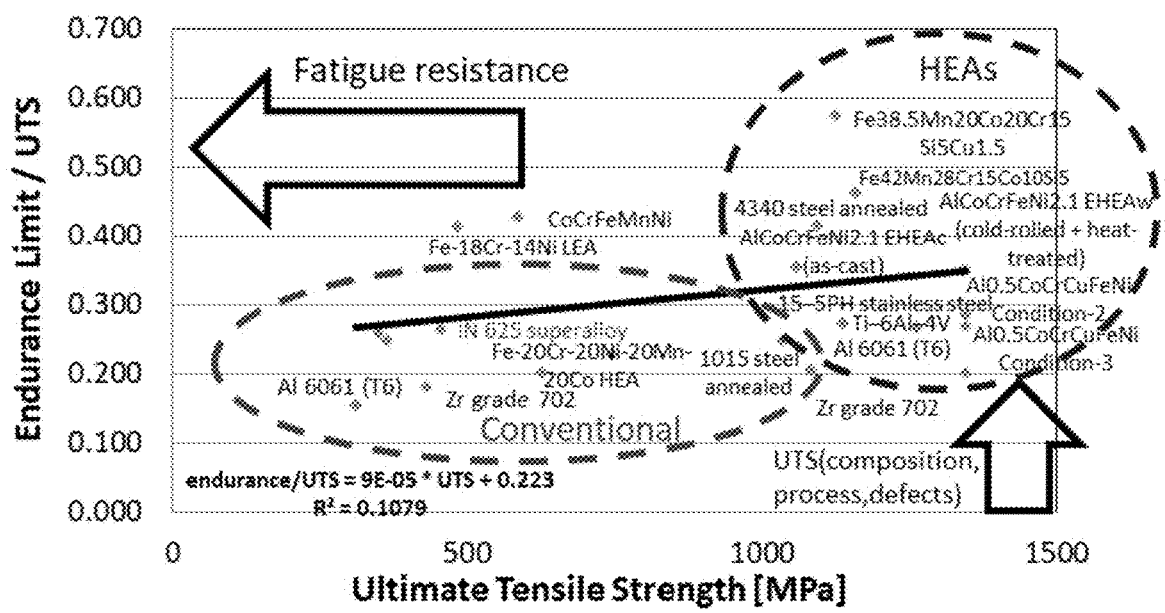
FIG. 26

Original Database
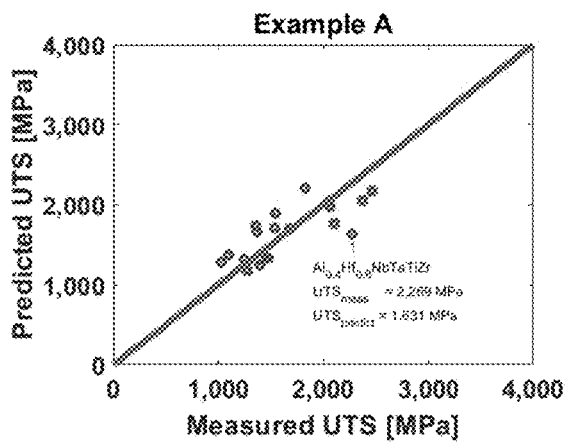
Overall standard deviation = 278.9 MPa
Normalized std. dev. per data point = 14.7 MPa
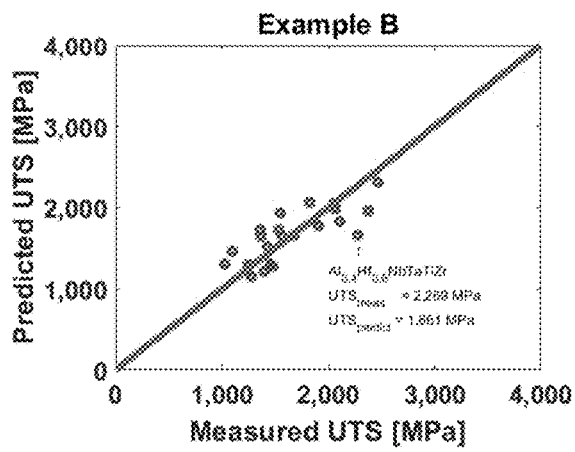
Overall standard deviation = 263.0 MPa
Normalized std. dev. per data point = 12.0 MPa
Enhanced Database
Example C
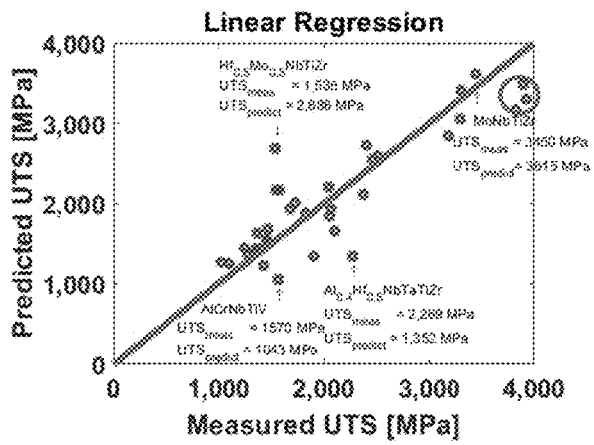
Overall standard deviation = 400.5 MPa
Normalized std. dev. per data point = 11.1 MPa
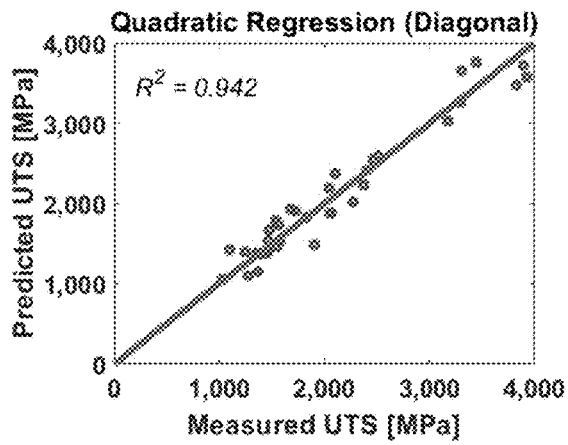
Overall standard deviation = 202.3 MPa
Normalized std. dev. per data point = 5.6 MPa
FIG. 36

MACHINE LEARNING TO ACCELERATE ALLOY DESIGN

CROSS REFERENCE TO RELATED APPLICATIONS

This application claims priority under 35 U.S.C. 119(e) to U.S. Patent Application Ser. No. 62/801,280, filed on Feb. 5, 2019, the entire contents of which are hereby incorporated by reference.

ACKNOWLEDGEMENT OF FEDERAL FUNDING

This utility patent traces its origin to research conducted under support of National Science Foundation Awards 1,447,395 and 1,632,408.

Xuesong Fan and Dr. Peter K. Liaw very much appreciate the support of the U.S. Army Research Office Project (W911NF-13-1-0438 and W911NF-19-2-0049) with the program managers, Drs. M. P. Bakas, S. N. Mathaudhu, and D. M. Stepp.

Dr. Peter K. Liaw thanks the support from the National Science Foundation (DMR-1611180 and 1809640) with the program directors, Drs. G. Shiflet and D. Farkas.

BACKGROUND OF THE INVENTION

This patent addresses the application of data analytics and optimization techniques, such as machine learning, to accelerate the design of alloys, exhibiting exceptional material properties, such as at high temperature. Specifically, we present apparatus and methods for accelerating the design of HEAs. Similar apparatus and methods can be used for accelerating the design of CMCs or PMCs, such as for high-temperature aerospace applications.

1. TECHNICAL FIELD DESCRIPTION 1.1 Alloys with Large Composition Space (High-Entropy Alloys)

Miracle & Senkov (MiracleSenkov 2017) noted in 2017 that the history of multi-component and high-entropy crystalline alloys, only extended over 14 years. Despite this relatively short history, the field has stimulated new ideas, and has inspired the exploration of the vast composition space offered by multi-principal element alloys. The two major, new concepts of this approach include (a) opening a vast, unexplored realm of alloy compositions and (b) the potential to influence solid-solution phase stability through control of configurational entropy. This discovery has catalyzed significant excitement in the materials community due to the attractive properties of HEAs. Extensive research has been carried out on numerous HEAs, and many attractive properties have been achieved, such as high hardness and strength, high fatigue resistance and fracture toughness, high-temperature oxidation resistance, high corrosion resistance, and unique electrical and magnetic properties (LiLiuLiaw 2018). HEAs have been established as potentially suitable applications for structural and functional materials. Another intriguing characteristic of HEAs involves exceptional fracture toughness at cryogenic temperatures, making them a candidate for low-temperature structural materials.

As further noted by Miracle & Senkov (MiracleSenkov 2017), a bold and expansive exploration of the vastness of the compositions space of HEAs is essential. This is a compelling prospect in the field of complex, concentrated alloys. The potential for new discoveries associated with this concept has hardly been scratched. Thirty-seven elements have been used to date in HEAs, giving 435,897 possible 5-element combinations and a total of 2,834,496 alloy systems with 3-6 elements. Considering the 72 elements that are not toxic, radioactive, or noble gases, the number of 5-element systems expands to 13,991,544, and the number of systems with 3-6 elements explodes to 171,318,882. Roughly 400 MPEAs have been reported to date, and many of those are non-equimolar variations of the same elements, giving only 112 different element combinations considered at the time (MiracleSenkov 2017).

To accelerate the exploration of complex compositions and microstructures, Miracle & Senkov (MiracleSenkov 2017) encourage the CCA community to develop and apply high-throughput computations and experiments, and to include data on complex, concentrated materials from other fields. For this purpose, the application of machine learning may accelerate the discovery of new materials by leveraging as input existing data on potential alloy compositions and processing. FIG. 1 presents a high-level summary of the primary input factors impacting the material properties of alloys, such as high-entropy alloys. FIG. 2 presents a more detailed overview, specific to fatigue properties, and one that illustrates dependence between the sources. FIG. 3 illustrates analogous driving factors, for the case of composites.

1.2 Composition Space of HEAs Relative to Conventional Alloys

According to Senkov, Miracle et. al. (SenkovMillerMiracle 2015), conventional alloys "have one principal element, with minor modifications achieved by adding relatively-small amounts of other elements. As many as a dozen other elements may be added, but conventional alloys still usually have a majority atom fraction of the base element. This strategy optimizes a suite of properties while retaining the characteristic properties of the base element that make this alloy family attractive. Multi-principal element alloys, out of which alloys with $\geq 5$ elements are also called high entropy alloys, are a new alloy development philosophy where the base alloy has significant atom fractions of several elements. Four or more base elements are commonly used, and although MPEAs often have equal concentrations of N base elements, this is not required. A common rationale for increasing N is to maximize the configurational entropy, in order to improve the stability of disordered solid-solution phases, thus suppressing the formation of intermetallic phases."

"This new alloying strategy vastly increases the number of possible alloy systems, giving a rich composition and phase space that has not yet been explored. For example, a palette of 12 elements gives 12 conventional alloy systems where 1 element dominates. Significant changes in the phases present and their reaction temperatures of MPEAs give a unique alloy system for each combination of elements. If an alloy base is made by combining 3 of the 12 elements in the palette above, then there are 220 distinct combinations of elements" (that is, the binomial coefficient) (SenkovMillerMiracle 2015). "Each of these 220 alloy families can be modified by altering the relative concentrations of the 3 base elements or by adding relatively-minor amounts of other elements as is done in conventional alloys. The same palette of 12 elements gives 495 alloy families with 4-base-elements; 792 systems with 5-base-elements, 924 with 6-base-element systems and a total of 4,017 alloy systems consisting of between 3 and 12 base elements. Thus, while the number of conventional alloy systems equals the number of elements in a palette, the number of MPEA systems is a function of N!, vastly increasing the number of systems." (SenkovMillerMiracle 2015).

1.3 Application of AI or ML to Alloy Design

1. Rapid Screening of Material Property Data Sets

It can be quite time-consuming and cost-intensive to fabricate alloy structures, esp. HEA structures via AM, using a trial & error approach. Data analysis methods using AI and ML have been applied to rapidly screen material property data sets (databases) for desirable material functions. By necessitating fewer experiments, AI and ML techniques offer the promise of reducing development times for new energy material manufacturing from discovery to marketable product to about 4-5 years, down from the current 15-20 years, with a corresponding reduction in development costs. To this effect, General Electric has been able to cut their jet engine alloy development cycle from 15 years to 9 years, by using computational approaches (NISTmgi2019). General Electric hopes to cut the time by half again using improved models and data (NISTmgi2019).

2. Material Property Data Sets Publicly Available

Citrine (CitrineResearch 2019) is aggregating data from multiple databases and making them available to integrated search and data mining. OPTiMaDe (OPTiMaDe 2020) is making a single portal to many databases of computed properties. For other pertinent material databases, refer to NIST CALPHAD Data Informatics databases (NISTCalPhad 2019), the CHIMAD Polymer Property Predictor Database (CHIMaD 2020), or the databases associated with the Materials Genome Initiative (NISTmgi2019).

3. Significance of Physics-Based Models for Improved Prediction Accuracy

The accuracy of prediction, resulting from the aforementioned screening of material property data sets, tends to be highly dependent upon quality and completeness of the input data. Oftentimes, the input data tends to be less complete than desired. In this case, it is of paramount importance to make the most of the limited data available. Here, physics-based models tend to help. As opposed to "blindly" extrapolating into sparsely populated, or even unpopulated, sections of the parameter space, it helps to account for underlying physics along the way.

1.4 Additive Manufacturing of Metallic Components

1. Introduction

AM is considered as a revolutionary technology to fabricate lightweight, flight- and marine-critical metallic components. The ability to produce complex and tailored structure designs opens the door for improved efficiency in existing products, and can function as a key enabler to new uses like hypersonic applications. Many merits, such as high efficiency, flexibility, and cost saving, give AM the potential to become a widely-utilized fabrication process for industrial applications.

With numerous, sometimes over 100, sources affecting the properties of additively manufactured components (ChernNandwana 2019), such as the fatigue life, the application of parametric models becomes infeasible. Traditional, parametric models can account for key sources, but not for all the 100+ sources. ML can help in terms of accounting for all the sources that impact the properties of AM components.

Additive manufacturing differs considerably from traditional manufacturing of alloys. The main difference relates to the speed of manufacturing. Additive manufacturing can be quite fast. The speed can impact aspects, such as the microstructure and kinetics, to name a few, and contribute to defects.

2. Primary Categories of Metal AM Technologies

FIG. 4 presents a generic overview over metal AM technologies (KokTanWangNai 2018). Metal AM processes can be grouped into three categories: powder-bed fusion, direct energy deposition and sheet lamination (Frazier 2014). Each process has its own advantages and disadvantages. Due to relative popularity, the primary focus here is on powder-bed fusion and DED.

The main undesirable features of metal AM processes often involve non-equilibrium thermal cycles. These can lead to solid-melting crystallization and solid-remelting recrystallization under fast heating and cooling conditions, which can result in anisotropic microstructures and defects (KokTanWangNai 2018) The microstructures and defects can significantly affect the performance of AM metallic parts, such as the fatigue life.

2.1 Powder-Bed Fusion

The PBF process includes selective laser melting, direct metal laser sintering, selective laser sintering, and electron beam melting.

For the powder bed fusion process, there are over 50 process parameters that impact the ultimate quality of the finished part, creating a significant challenge in understanding the process physics. Broadly speaking, these parameters can be classified into four categories:

TABLE 1

Summary of key process parameters of SLM and SLS (SpearsGold 2016).

| No. | Parameter | Description | Configuration |
|---|---|---|---|
| | | Laser and scanning parameters | |
| 1 | Average power | Measure of total energy output of a laser | Controlled |
| 2 | Mode | Continuous wave or pulsed | Predefined |
| 3 | Peak power | Maximum powder in a laser purse | Predefined |
| 4 | Pulse width | Length of a laser pulse when operating in pulsed mode | Predefined |
| 5 | Frequency | Pulses per unit time | Predefined |
| 6 | Wavelength | Distance between crests in laser electromagnetic waves | Predefined |
| 7 | Polarization | Orientation of electromagnetic waves in laser beam | Predefined |
| 8 | Beam quality | Related to intensity profile and used to predict how well beam can be focused and determine min. theoretical spot size | Predefined |
| 9 | Intensity profile | Determines how much energy added at a specific location | Predefined |
| 10 | Spot size | Length and width of elliptical spot | Controlled |
| 11 | Scan velocity | Velocity at which laser moves across build surface | Controlled |
| 12 | Scan spacing | Distance between neighboring laser passes | Controlled |
| 13 | Scan strategy | Pattern in which the laser is scanned across the build surface (hatches, zig-zags, spirals, etc.) and associated parameters | Controlled |

TABLE 1-continued

Summary of key process parameters of SLM and SLS (SpearsGold 2016).

| No. | Parameter | Description | Configuration |
|---|---|---|---|
| | | Powder material properties | |
| 14 | Bulk density | Material density, limits maximum density of final component | Predefined |
| 15 | Thermal conductivity | Measure of material's ability to conduct heat | Predefined |
| 16 | Heat capacity | Measure of energy required to raise temp. of material | Predefined |
| 17 | Latent heat fusion | Energy required for solid-liquid and liquid-solid phase change | Predefined |
| 18 | Melting temperature | Temperature at which material melts | Predefined |
| 19 | Boiling temperature | Temperature at which material vaporizes | Predefined |
| 20 | Melt pool viscosity | Measure of resistance of melt to flow | Predefined |
| 21 | Coef. Of thermal expansion | Measure of volume change of material on heating or cooling | Predefined |
| 22 | Surface free energy | Free energy required to form new unit area on heating or cooling | Predefined |
| 23 | Vapor pressure | Measure of the tendency of material to vaporize | Predefined |
| 24 | Heat (enthalpy) of reaction | Energy associated with a chemical reaction of material | Predefined |
| 25 | Material absorptivity | Measure of laser energy absorbed by the material | Predefined |
| 26 | Diffusivity | Important for solid state sintering, not critical for melting | Predefined |
| 27 | Solubility | Solubility of solid material in liquid melt | Predefined |
| 28 | Particle morphology | Measures of shape of individual particles and their distribution | Predefined |
| 29 | Surface roughness | Arithmetic mean of the surface profile | Predefined |
| 30 | Particle size distribution | Distribution of particle sizes, usually diameter, in a powder sample | Predefined |
| 31 | Pollution | Ill-defined factor describing change in properties of powder due to reuse | Predefined |
| | | Powder bed and recoat parameters | |
| 32 | Density | Measure of packing density of powder particles, influence heat balance | Predefined |
| 33 | Thermal conductivity | Measure of powder bed's ability to conduct heat | Predefined |
| 34 | Heat capacity | Measure of energy required to raise temp. of powder bed | Predefined |
| 35 | Absorpivity | Measure of laser energy absorbed | Predefined |
| 36 | Emissivity | Ratio of energy radiated to that of black body | Predefined |
| 37 | Deposition system param's | Recoater velocity, pressure, recoater type, dosing | Controlled |
| 38 | Layer thickness | Height of a single powder layer | Controlled |
| 39 | Powder bed temp. | Bulk temperature of the powder bed | Controlled |
| | | Build environment parameters | |
| 40 | Shield gas | Usually Ar or $N_2$, but may also be He or something else | Predefined |
| 41 | Oxygen level | Probably most important environment parameter; oxygen can lead to oxide formation in metal, change wettability, energy required for welding, etc. | Controlled |
| 42 | Shield gas mol. weight | Influences heat balance, diffusivity into and out of part | Predefined |
| 43 | Shield gas viscosity | May influence free surface activity of melt pool, convective heat balance | Predefined |
| 44 | Thermal conductivity | Term in heat balance | Predefined |
| 45 | Heat capacity of gas | Term in heat balance | Predefined |
| 46 | Pressure | Influences vaporization of metal as well as oxygen content | Controlled |
| 47 | Gas flow velocity | Influences convective cooling, removal of condensate | Controlled |
| 48 | Convective heat transfer coef. | Convective cooling of just melted part by gas flowing over the surface | Predefined |
| 49 | Ambient temperature | Appears in heat balance, may impact powder preheat and residual stress | Controlled |
| 50 | Surface free energy | Between liquid and surround gas influence melt pool shape | Predefined |

1. Laser and scanning parameters,
2. Powder material properties,
3. Powder bed properties and recoat parameters, and
4. Build environment parameters.

These properties (parameters) are summarized in Table 1.

2.2 Direct Energy Deposition

The DED process can be further classified with respect to the use of powder or wire as feedstock. The powder-based DED process includes laser engineered net shaping, direct metal deposition, laser metal deposition, and laser free-form fabrication. Meanwhile, the wire-based DED process includes electron beam free-form fabrication and shaped metal deposition. SMD include the WAAM process. The WAAM process can be further categorized into three types: MIG-based, TIG-based, and plasma-based processes.

Table 2 presents comparison between processing parameters of LENS and laser PBF. Table 3 presents further comparison between the SLM, EBM and WAAM processes for metal AM.

TABLE 2

Comparison of processing parameters for LENS and laser PBF.

| | LENS (e.g., OPTOMEC 450) | Laser PBF (e.g., EOS M290) |
|---|---|---|
| Maximum laser power | 400 W | 400 W (actual use, not exceed 370 W) |
| Maximum scan speed | 1016 mm/min | 7000 mm/s |
| Layer thickness | 200-300 μm | 20-50 μm |
| Focus diameter | 400 μm | 100 μm |
| Powder feed rate | 5-15 g/min | N/A |
| Oxygen concentration | Less than 10 ppm | Less than 0.1% (1000 ppm) |
| Particle size | 36-150 microns | 15-53 microns |
| Pre-heating | Can be heated to 600° C. or cooled to 20° C. by circulating coolant | Can be preheated to 200° C. |
| Hatch spacing | 200-400 μm | 50-150 μm |
| Scan strategy | Continuous, island, etc | Continuous, island, etc |

3. Review of Sources Impacting Properties and Performance of AM Metallic Components FIG. 5 lists some of the primary sources contributing to the fatigue life of additively-manufactured metallic components. Other parameters, which can impact the fatigue life failure of AM metallic components, include the powder characteristics (say, the powder size and distribution), weld pool, and cooling speed (DebRoyWei 2018), (ChernNandwana 2019).

The artifacts impacting the properties and performance of AM metallic components can be classified into macro, micro and nano-scale effects, as shown in Table 4.

TABLE 3

Comparison between SLM, EBM and WAAM metallic AM processes.

| Category | Sub-Category | Selective Laser Melting | Electron Beam Melting | Wire + Arc Additive Manufacturing |
|---|---|---|---|---|
| System | Energy source | Laser | Electron beam | TIG-based MIG-based Plasma-based |
|  | Max. Fabricated component size | 400 × 400 × 400 mm³ | 200 × 200 × 180 mm³ | 610 × 610 × 5,182 mm³ |
|  | Material deposition rate | 5-35 cm3/hr. | 80 cm3/hr. | Up to 10 kg/hr. |
|  | Functionally-graded material | Difficult | Difficult | Available |
| Material | Type | Powder | Powder | Wire |
|  | Available materials | Titanium alloy Carbon steels Stainless steels Inconel alloys . . . | Titanium alloy Carbon steels Stainless steels Inconel alloys . . . | Stainless steel Carbon steels Cobalt alloys Nickel alloys Aluminum alloys Copper-Nickel alloys Inconel alloys Titanium alloy . . . |

TABLE 4

Identification of the scale at which different artifacts apply.

| Scale | Artifact |
|---|---|
| Macro | Residual stress, surface roughness/waviness, voids, crack, geometric shape |
| Micro | Micro-voids, micro-cracks, micro-structure size, micro-structure orientation, segregation, intermetallic |
| Nano | Twin boundary, grain boundary |

4. Interrelationships between Sources Impacting Properties of AM Components and the Underlying Physics The sources listed in FIG. 6, such as residual stress, may exhibit dependence on other parameters, such as layer thickness or temperature. FIG. 7 provides insight into the relationship between the input parameters and the underlying physics (SamesListPannala 2016). Understanding the root causes of defects and inhomogeneities is one of the keys to successfully predicting the properties and performance of additively manufactured components.

1.5 Application of AI or ML to the Design of Material AM Processes or Intelligent AM Systems 1. Material AM Processes AI and ML approaches leading to the next generation of commercially viable energy materials manufacturing will require new models of materials and processes, based on experimental and computational data, and the use of models to predict material compositions of optimal material functionality correlated to manufacturing process conditions.

2. Intelligent AM Systems

AI and ML can also be used to better distribute, monitor and control the processing energy in a laser metal powder bed fusion AM systems, for the purpose of real-time process monitoring and control towards producing high-quality, defect-free AM parts with build periods comparable or shorter than present ones.

Despite continued progress in AM technologies, AM parts still require several trial and error runs with post-processing treatments and machining to optimize builds, reduce defects and residual stresses, and meet tolerances. AM still lacks a stable process that can produce consistent, defect-free parts on a first time basis due to our inability to reliably predict the optimal trajectory in the multidimensional process parameter space due to the inherent spatiotemporal variability in the process parameter and the chaotic nature of the AM process.

1.6 High-Temperature Applications

1. Motivation

By operating turbines with blades made of refractory HEAs (RHEAs) at significantly-higher temperatures than conventional alloys, one can expect drastic improvements in efficiency. Assuming a Brayton cycle and not accounting for losses, the thermal efficiency, $\eta$, of a gas turbine engine can be expressed as (Spakovszky 2019).

$$\eta = \frac{\text{network}}{\text{heat in}} = 1 - \frac{T_{atmospheric}}{T_{compressor\ exit}}. \quad (1)$$

Hence, by increasing the temperature at the compressor exit, $T_{compressor\ exit}$, the efficiency improves.

More specifically, assuming fossil-fuel combustion, the first stage of a modern turbine (the stage directly following the combustor), typically faces temperatures around 2,500° F. (1,370° C.). Modern military jet engines, like the Snecma M88, can experience turbine temperatures of 2,900° F. (1,590° C.). These high temperatures weaken the blades and make them more susceptible to creep failures. The high temperatures can also make the blades susceptible to corrosion failures. Specifically, vibrations from the engine and the turbine itself can cause fatigue failures (TurbineBlade 2019).

FIG. 8 provides glimpse into the "status quo", i.e., the benefits that RHEAs presently offer over conventional alloys, for high temperature applications. Per FIG. 8, the refractory HEAs of Type 3 (HEA-3) exhibit 2×-4× higher yield strength at high temperature (T>1200 K), compared to the conventional alloys. The higher yield strength of the RHEAs may allow turbine vendors to decrease the weight of the turbo blades, and hence reduce cost. In addition, per Eq. (1), the higher melting point may improve the theoretical efficiency by ~7-9%, from ~79% to ~87%, assuming $T_{atmospheric} \cong 273$ K for land-based turbines, assuming the idealized adiabatic and constant pressure processes in the Brayton cycle, and not accounting for losses.

2. Role of AI and ML for Development of Alloys Suitable for High-Temperature Applications Overall, there is need for refractory alloys (structural) yielding superior strength at higher temperature, together with favorable oxidation properties, while still exhibiting reasonable ductility at room temperature. To that end, AI or ML can help with rapid screening of candidate compositions.

3. Role of AM for High-Temperature Applications

AM technologies have an immense potential to allow for gas turbines of higher efficiency (up to 7%-9% increase in efficiency) and more cost-effective generator and steam turbine components (up to 15-20% cost reduction), by taking advantage of AM innovative component geometries. FIG. 9 shows that AM can result in lower manufacturing cost, compared to conventional manufacturing, in case of designs consisting of a few number of parts or of very complex components. Hence, AM can be one of the solutions to fabricate the RHEAs for energy conversion applications.

4. Environmental (Corrosion) Resistance

AI and ML can be utilized to detect data patterns and characteristic trends, learn from accumulated data, and evolve distinguishing characteristics between different types of hot corrosion attacks, such as calcium-magnesium-alumino-silicate and calcium sulfate attacks, with or without the influence of sea salt, in order to develop suitable coatings resistant to hot corrosion.

1.7 Other Applications—Composites

This invention also addresses development of new data analytics and machine learning methods, in an effort to investigate and understand structure-property-performance relationships in multi-functional PMCs and CMCs, to facilitate accelerated materials' design for next-generation multi-functional composites, such as for high-temperature aerospace applications.

DESCRIPTION OF PRIOR ART

2.1 Phase Diagrams and ICME

As noted by Miracle & Senkov (MiracleSenkov 2017), phase diagrams are roadmaps for the materials design. They give the essential information for a given alloy composition and temperature, including the phases present, their compositions, volume fractions, and transformation temperatures. Most binary and some ternary phase diagrams have been measured experimentally, but multi-component systems remain mostly unexplored. The experimental definition of multi-component phase diagrams is impractical, due to the tremendous amount of work involved. In recent years, the integration of the CALPHAD approach with key experiments has been demonstrated as an effective approach to determine complicated multi-component phase diagrams (MiracleSenkov 2017), (FengGaoZhangGuo 2018), (ZhangZhangDiaoGao 2016), (ShiCollinsFengZhang 2018).

ICME tool sets, based on the CALPHAD methodology, include Thermo-Calc (Thermo-Calc 2014) DICTRA and the Pandat software (CompuTherm2020). FIG. 28-FIG. 32 provide a high-level overview of CALPHAD. Existing toolsets for ICME cannot predict how AM affects material properties of additively manufactured parts. While machine learning or data analytics are yet to be incorporated into CALPHAD, to our knowledge, Ref (QuesTek 2020) lists patents addressing alloys developed by QuesTek Innovations LLC using ICME tools.

U.S. Pat. No. 10,495,590 B2 may or may not come across as similar to the present invention. U.S. Pat. No. 10,495,590 B2 presents methods for selecting material compositions and designing materials exhibiting a target property. Such methods seem to resemble the CALPHAD methodology (see FIG. 28-FIG. 32). Moreover, in U.S. Pat. No. 10,495,590 B2, there is no mention of the terms "regression", "neural networks" or "machine learning".

2.2 Application of Machine Learning for Accelerating Identification of Alloys with Desired Properties

1. Prior Art Considered

Liu et. al. (LiuKumarChen 2015) report that machine learning yields time reduction of 72%-88%, over exhaustive search (eSearch) or smarter-than-random guided search (gSearch), when applied to optimization of five design problems, involving a recently discovered alloy, Galfenol. Here both the eSearch and gSearch were applied as a part of a machine learning-based structure-property optimization route (LiuKumarChen 2015).

In (LiuKumarChen 2015), Liu et. al. address how one can identify the complete space (or as much of it as possible) of microstructures that are theoretically predicted to yield the desired combination of properties demanded by a selected application. The authors present a problem involving the design of the magnetoelastic Fe—Ga alloy microstructure for the enhanced elastic, plastic, and magnetostrictive properties. While theoretical models for computing properties given the microstructure are known for this alloy, the inversion of these relationships, to obtain microstructures that lead to desired properties, is challenging, primarily due to the high dimensionality of the microstructure space, due to multi-objective design requirements, and non-uniqueness of solutions. These challenges render traditional search-based optimization methods incompetent in terms of both searching for efficiency and result optimality. This invention presents machine learning as a route to address these challenges. A systematic framework, consisting of the random data generation, feature selection, and classification algorithms, is presented. Experiments with five design problems that involve the identification of microstructures that satisfy both linear and nonlinear property constraints show that the proposed framework outperforms traditional optimization methods with the average running time reduced by as much as 80%, and with the optimality that would not be achieved otherwise.

Agrawal et. al. (AgrawalDeshpande 2014) used machine learning methods to predict the fatigue strength of steels, based on their composition and processing. Oliynyk et. al. (OlinykAntonoSparks 2016) showed that a high-throughput machine learning approach could be used to screen for potential Heusler alloys. Xue et. al. (XueXueYuan 2017) used machine learning to predict the transformation temperature of shape memory alloys using computational results. Conduit et. al. (ConduitJonesStone 2017) built a neural network to design new nickel super-alloys and showed that if given composition and processing steps, they could build a model for several mechanical properties. DeCost et al. (DeCostFrancisHolm 2016) used a convolutional neural network to classify the microstructures of steel processed with different heat treatments. These and other studies demonstrate the applicability of machine learning algorithms to predict quantities of interest for both structural and functional alloys.

The platform of (LingAntonoBajaj 2018) uses ensemble ML algorithms, which means that instead of building a single model to predict a given quantity of interest, many models (often hundreds) are built on different random subsets of the training data. Each model makes a prediction for any new test point, and the final ensemble prediction is given by the average value of all the individual model predictions. Such ensemble models have been shown to give high performance and to be robust to noise in the training data (Polikar 2012). These ensemble models are implemented in such a way as to be capable of operating on sparse data sets, for which data on all the inputs and all the properties of interest are not available for every test point.

To address data limitations, in application of machine learning to material science, authors such as (JolySarkarMehta 2019) have suggested using multi-source learning or surrogate assisted optimization. These authors have suggested arranging the data in a hierarchy of fidelity. They have claimed that you can sample low-fidelity data and use to improve a prediction model (reduce variance, but not improve a mean).

Ref (KR20040008381A) references "an artificial intelligence data modeling techniques to introduce alloy neural network design program. The alloy design program is a program that we calculate on the basis of the thermodynamic and mechanical properties of the alloy composition when the input to the existing experimental data. In NNADP used in this example it is precisely predicted than the conventional alloy design program of the creep life of the most important characteristics in a single crystal alloy by using the neural network techniques that rely on multiple regression analysis." While Ref. (KR20040008381A) does describe an approach to alloy design relying on physical models, it appears the application of the physical models was conducted by a human, separate from the multiple regression analysis. It does not appear that the physical models were integrated into the neural network techniques. It appears that the neural network techniques employed were "out-of-the-box" (or in other words "off-the-shelf").

Ref (US20160034614A1) describes a materials property predictor for casting aluminum alloys. Ref. (US20160034614A1) differs from the present invention in the following aspects:
  1. Ref (US20160034614A1) seems limited to casting of aluminum alloys (and hence, does not address the vast composition space of HEAs).
  2. Ref (US20160034614A1) seems limited to prediction using a k-NN approach, whereas the present invention considers prediction based on regression analysis or an ANN predictor, based on what is suitable for the application at hand and the data available.
  3. Ref (US20160034614A1) seems limited to physical models obtained from a thermodynamic calculation module (which comes across as similar to CALPHAD), whereas the present invention considers a much broader set of physical models, including those based on first-principle effects, empirical rules or mesoscale models.

2. Prior Art Apparently Succeeding Provisional Patent No. 62/801,280

Among Ref. (CN110010210A), Ref (CN110415769A), Ref. (CN110428876A), Ref. (CN110442953A), Ref. (CN110442954A) and Ref. (JP2020009435A), there is discussion about application of machine learning to alloy design, including to multi-component alloy systems. However, the filing date of these references does succeed the filing date of Provisional Patent No. 62/801,280. Hence, these references are not considered here in the context of prior art.

3. Prior Art Specifically Addressing Corrosion Resistance

Hot corrosion has been studied for a number of years, although not through application of machine learning. Djinn from Corrdesa is a commercial software for addressing galvanic corrosion (CorrdesaDjinn 2020).

Ref (KulkarniEPRI 2020) presents a deposition model capable of identifying high-risk areas for deposit build-up for actual components in a gas turbine.

2.3 Application of AI or ML to Additive Manufacturing

Despite the high potential of additive manufacturing, it has been found that the fatigue life of as-deposited AM components is often low, compared to wrought components produced by the conventional technology. The AM process is comprised of numerous cycles of material addition and rapid heating and cooling (rapid melting and solidifying). As a result, the fatigue performance in AM parts has been attributed to a complex combination of material and process-induced imperfections. Due to the complexity of fatigue behavior of an AM part, a comprehensive toolset, based on an ICME framework, may be needed to predict fatigue strength and fatigue life in AM metallic components. For critical components, like those in airframe applications, developing a better understanding of fatigue performance is essential for further adoption of the technology.

1. Prior Art of Greatest Relevance

For relevant papers by the authors on HEA design for additive manufacturing, refer to (ChenTongLiaw 2018), (ZhuNguyenNgAnLiao 2018). (ZhuNgQiaoLiawChen 2018)

The closest analogue to the present invention, in terms of prior art, may involve Ref. (US20190337232A1). Ref. (US20190337232A1) addresses non-dimensionalization of variables to enhance machine learning in additive manufacturing processes. The method includes applying a transform to values of at least two variables of the process data to generate a dimensionless parameter having a parameter value corresponding to each measurement of the physical system for at least two variables. While this may seem like an approach for addressing the multiple sources that impact the quality of additively manufactured components, it does come across as a specific one (one only addressing non-dimensionalization). The approach certainly does not address the application of AI or ML to better distribute, monitor and control the processing energy in a laser metal powder bed fusion AM systems, for purpose of real-time process monitoring and control aimed at producing high-quality, defect-free AM parts with build periods comparable or shorter than present ones.

Existing software tools for fatigue prediction cannot consider how additive manufacturing affects the material properties of additively manufactured parts.

2. Prior Art Specifically Addressing Prediction of Properties of Additively Manufactured Components Prior art specifically addressing the prediction of properties of additively manufactured components includes (GarangerFeron 2017), (ZhuAnwarHuang 2018) and (VandoneBaraldo 2018).

3. Prior Art Specifically Addressing Intelligent AM Systems

Prior art specifically addressing intelligent AM systems includes (ZhuAnwarHuang 2018), (ScimeBeuth 2018) and (PeterZielinksi 2020).

REFERENCES (MiracleSenkov 2017) D. B. Miracle and O. N. Senkov, "A Critical Review of High Entropy Alloys and Related Concepts," *Acta Materialia*, vol. 122, pp. 448-511, 2017.

(Spakovszky 2019) Z. Spakovszky, "Thermo-dynamics and Propulsion," Available: https://web.mit.edu/16.unified/www/SPRING/propulsion/notes/node27.html. Accessed on 5 May 2019.

(ChernNandwana 2019) A. H. Chern, P. Nandwana, T. Yuan, M. M. Kirkna, R. R. Dehoff, P. K. Liaw and C. E. Duty, "A review on the fatigue behavior of Ti-6Al-4V fabricated by electron beam melting additive manufacturing," *International Journal of Fatigue*, vol. 119, pp. 173-184, 2019.

(SpearsGold 2016) T. G. Spears and S. A. Gold, "In-process sensing in selective laser melting (SLM) additive manufacturing", *Integrating Materials and Manufacturing Innovation*, vol. 5, no. 2, 2016.

(AsmHandbook 1990) ASM International. Handbook Committee (Ed.), ASM Handbook, Vol. 2, 1990.

(CN110010210A) Fu Huadong, Xie Jianxin, Wang Changsheng, "Multicomponent alloy composition design method based on machine learning and performance oriented requirement", filed on Mar. 29 2019.

(CN110415769A) Wang Chenchong, Cui Qing, Huang Jian, Xu Wei, Shen Chunguang, "The design method of the low activation steel of lower machine learning is instructed based on physical metallurgy", filed on Jul. 31 2019.

(CN110428876A) Xu Wei, Shen Chunguang, Huang Jian, Wang Chenchong, Yuan Jiahua, "A kind of steel material design method of the machine learning algorithm based on physical instruction", filed on Jul. 31 2019.

(CN110442953A) Xu Wei, Zhu Kaiyu, Huang Jian, Wang Chenchong, Shen Chunguang, "The design method of the Q&P steel of lower machine learning is instructed based on physical metallurgy", filed on Jul. 31 2019.

(CN110442954A) Xu Wei, Xu Ning, Huang Jian, Wang Chenchong, Yuan Jiahua, Shen Chunguang, "The super high strength stainless steel design method of lower machine learning is instructed based on physical metallurgy", filed on Jul. 31 2019.

(JP2020009435A) Keita Ozaki, Yo Okamoto, "Steel component learning device, steel component estimation device, steel type determination device, steel component learning method, steel component estimation method, steel type determination method, and program", filed on Jun. 27 2019.

(KR20040008381A) Korea Institute of Machinery and Materials, "Single crystal Ni based super-alloy having excellent high temperature creep characteristic", KR20040008381A, filed on Jul. 18 2002.

(U.S. Ser. No. 10/495,590 B2) K. Vecchio and J. L. Cheney, "Methods of Selecting Material Compositions and Designing Materials Having a Target Property", U.S. Pat. No. 10,495,590 B2, granted on Dec. 3 2019.

(US20160034614A1) Q. Wang, B. Li, Y. Wang, "Materials Property Predictor for Cast Aluminum Alloys", Pub. No. US 2016/0034614 A1, published on Feb. 4 2016.

(US20190337232A1) S. P. Narra and J. L. Beuth Jr., "Non-Dimensionalization of Variables to Enhance Machine Learning in Additive Manufacturing Processes", Pub. No 2019/0337232 A1, published on Nov. 7, 2019.

(VandoneBaraldo 2018) A. Vandone, S. Baraldo, and A. Valente, "Multisensor Data Fusion for Additive Manufacturing Process Control." IEEE Robotics and Automation Letters, Vol. 3, No. 4, 32018, pp. 279-3284. DOI: 10.1109/LRA.2018.2851792.

(ZhuAnwarHuang 2018) Z. Zhu, N. Anwar, Q. Huang, and L. Mathieu, "Machine learning in tolerancing for additive manufacturing." CIRP Annuals, Vol. 67, No. 1, pp. 157-160. DOI: 10.1016/j.cirp.2018.04.119, 2018.

(GarangerFeron 2017) K. Garanger, E. Feron, P. Garoche, J. J. Rimoli, J. D. Berrigan, M. Grover and K. Hobbs, "Foundations of Intelligent Additive Manufacturing", arxiv.org/pdf/1705.00960.pdf, May 12 2017.

(ScimeBeuth 2018) L. Scime, and J. Beuth, "Anomaly detection and classification in a laser powder bed additive manufacturing process using a trained computer vision algorithm." Additive Manufacturing, Vol 19, pp. 114-126. sciencedirect.com/science/article/pii/S221486041730180X, January 2018.

(PeterZielinksi 2020) Peter Zielinski (editor). How Machine Learning Is Moving AM Beyond Trial and Error (Originally titled 'Where AM Meets AI'). Additive Manufacturing. additivemanufacturing.media/articles/how-machine-learning-is-moving-am-beyond-trial-and-error, accessed on Jan. 29 2020.

(BrownHoMindlin 1979) W. F. Brown, C. Y. Ho and H. Mindlin, Aerospace structural metals handbook. CINDAS-USAF CRDA Handbooks Operation, Purdue University, 1979.

(DebRoyWei 2018) T. DebRoy, H. L. Wei, J. S. Zuback, T. Mukherjee, J. W. Elmer, J. O. Milewski, A. M. Beese, A. Wilson-Heid, A. De and W. Zhang, "Additive manufacturing of metallic components—Process, structure and properties," *Progress in Materials Science*, vol. 92, pp. 112-224, 2018.

(KulkarniEPRI 2020) A. A. Kulkarni, M. Senga, S. W. Kiliani, J. Sumner and N. J. Simms, "Component Level Hot Corrosion and Deposit Modeling for Large Gas Turbines," in Electric Power Research Institute, Charlotte, North Carolina, 2020.

(SamesListPannala 2016) W. J. Sames, F. A. List, S. Pannala, R. R. Dehoff, and S. S. Babu, "The metallurgy and processing science of metal additive manufacturing," *International Materials Reviews*, vol. 61, no. 5, pp. 315-360, 2016.

(JolySarkarMehta 2019) M. Joly, S. Sarkar and D. Mehta, "Machine Learning Enabled Adaptive Optimization of a Transonic Compressor Rotor with Precompression," Journal of Turbomachineary, vol. 141, no. 5, May 2019.

(KokTanWangNai 2018) Y. Kok, X. P. Tan, P. Wang, M. L. S. Nai, N. H. Loh, E. Liu and S. B. Tor, "Anisotropy and heterogeneity of microstructure and mechanical properties in metal additive manufacturing: A critical review," Materials and Design, vol. 139, pp. 565-586, 2018.

(Frazier 2014) W. E. Frazier, "Metal additive manufacturing: a review," *Journal of Materials Engineering and Performance*, vol. 23, no. 6, pp. 1917-1928, 2014.

(JosephStanford 2017) J. Joseph, N. Stanford, P. Hodgson and D. M. Fabijanic, "Understanding the mechanical behaviour and the large strength/ductility differences between FCC and BCC AlxCoCrFeNi high entropy alloys," *Journal of Alloys and Compounds*, vol. 726, pp. 885-895, 2017.

(GorsseHutchinson 2017) S. Gorsse, C. Hutchinson, M. Gouné and R. Banerjee, "Additive manufacturing of metals: a brief review of the characteristic microstructures and properties of steels, Ti-6Al-4V and high-entropy alloys," *Science and Technology of Advanced Materials*, vol. 18, no. 1, pp. 584-610, 2017.

(GrainBoundaryStrengthening 2019) Wikipedia, Grain Boundary Strengthening, https://en.wikipedia.org/wiki/Grain_boundary_strengthening, 2019.

(MenzelDauskardt 2006) B. C. Menzel and R. H. Dauskardt, "The fatigue endurance limit of a Zr-based bulk metallic glass," *Scripta Materialia*, vol. 55, pp. 601-604, 2006.

(HemphillYuanWang 2012) M. A. Hemphill, T. Yuan, G. Wang, J. Yeh, C. Tsai, A. Chuang, P. Liaw, "Fatigue behavior of al 0.5 cocrcufeni high entropy alloys," *Acta Materialia*, vol. 60,no. 16, pp. 5723-5734, 2012.

(KimHamKimLee 2019) Y.-K. Kim, G.-S. Ham, H. S. Kim, K.-A. Lee, "High-cycle fatigue and tensile deformation behaviors of coarse-grained equiatomic cocrfemnni high entropy alloy and unexpected hardening behavior during cyclic loading," *Intermetallics*, vol. 111, 2019.

(KashaevVentzke 2019) N. Kashaev, V. Ventzke, N. Petrov, M. Horstmann, S. Zherebtsov, D. Shaysultanov, V. Sanin, N. Stepanov, "Fatigue behaviour of a laser beam welded CoCrFeNiMn-type high entropy alloy," *Materials Science and Engineering: A*, vol. 766, 2019.

(SuzukiKoyamaHamada 2019) K. Suzuki, M. Koyama, S. Hamada, K. Tsuzaki and H. Noguchi, "Planar Slip-Driven Fatigue Crack Initiation and Propagation in an Equiatomic CrMnFeCoNi High-Entropy Alloy," *International Journal of Fatigue*, no. 2019.

(LiuGwalaniKomarasamy 2019) K. Liu, B. Gwalani, M. Komarasamy, S. Shukla, T. Wang and R. S. Mishra, "Effect of nano-sized precipitates on the fatigue property of a lamellar structured high entropy alloy," *Materials Science & Engineering A*, vol. 760, pp. 225-230, 2019.

(LiLiuLiaw 2018) W. Li, P. Liu, P. K. Liaw, "Microstructures and properties of high-entropy alloy films and coatings: a review," *Materials Research Letters*, vol. 6, no. 4, pp. 199-229, 2018/4/3.

(LiGazquez 2018) M. Li, J. Gazquez, A. Borisevich, R. Mishra and K. M. Flores, "Evaluation of microstructure and mechanical property variations in AlxCoCrFeNi high entropy alloys produced by a high-throughput laser deposition method," *Intermetallics*, vol. 95, pp. 110-118, 2018.

(LiuKumarChen 2015) R. Liu, A. Kumar, Z. Z. Chen, A. Agrawal, V. Sundararaghavan and A. Choudhary, "A Predictive Machine Learning Approach for Microstructure Optimization and Materials Design," *Scientific Reports*, vol. 5, p. Article number: 11551, 2015.

(TurbineBlade 2019) Wikipedia, "Turbine Blade," https://en.wikipedia.org/, May 5, 2019.

(SenkovMillerMiracle 2015) O. N. Senkov, J. D. Miller, D. B. Miracle and C. Woodward, "Accelerated exploration of multi-principal element alloys with solid solution phases," *Nature Communications*, vol. 6, no. 6529; DOI: 10.1038/ncomms7529, pp. 1-10, 2015.

(LingAntonoBajaj 2018) J. Ling, E. Antono, S. Bajaj, S. Paradiso, M. Hutchinson, B. Meredig and B. M. Gibbons, "Machine Learning for Alloy Composition and Process Optimization," in *ASME Turbo Expo* 2018*: Turbomachinery Technical Conference and Exposition; Volume 6: Ceramics; Controls, Diagnostics, and Instrumentation; Education; Manufacturing Materials and Metallurgy*, Oslo, Norway, Jun. 11-15, 2018.

(AgrawalDeshpande 2014) A. Agrawal, P. D. Deshpande, A. Cecen and G. P. Basavarsu, "Exploration of data science techniques to predict fatigue strength of steel from composition and processing parameters," *Integrating Materials and Manufacturing Innovation*, vol. 3, no. 1, p. 1-19, 2014.

(RadhakrishnanGorti 2019) B. Radhakrishnan, S. B. Gorti, J. A. Turner, R. Acharya, J. A. Sharon, A. Staroselsky and T. El-Wardany, "Phase Field Simulations of Microstructure Evolution in IN718 Using a Surrogate Ni—Fe—Nb Alloy during Laser Powder Fusion", Metals, Vol. 9, No. 1, 2019.

(RadhakrishnanGorti 2016) B. Radhakrishnan, S. B. Gorti and S. S. Babu, "Phase Field Simulations of Autocatalytic Formation of Alpha Lamellar Colonies in Ti-6Al-4V," *Metallurgical and Materials Transactions*. Vol, 47, pp. 6577-6592, 2016.

(OlinykAntonoSparks 2016) A. Oliynyk, E. Antono, T. Sparks, L. Ghadbeigi, M. Gaultois, B. Meredig and A. Mar, "High-throughput machine-learning-driven synthesis of full heusler compounds," *Chemistry of Materials*, vol. 28, no. 20, p. 7324-7331, 2016.

(XueXueYuan 2017) D. Xue, D. Xue, R. Yuan, Y. Zhou, P. Balachandran, X. Ding, J. Sun, and T. Lookman, "An informatics approach to transformation temperatures of NiTi-based shape memory alloys," *Acta Materialia*, vol. 125, p. 532-541, 2017.

(ConduitJonesStone 2017) B. Conduit, N. Jones, H. Stone and G. Conduit, "Design of a nickel-base superalloy using a neural network," *Materials and Design,* 2017.

(DeCostFrancisHolm 2016) B. L. Decost, T. Francis, and E. A. Holm, 2017. "Exploring the microstructure manifold: image texture representations applied to ultrahigh carbon steel microstructures", *Acta Materialia,* 133, pp. 30-40. 2017.

(Polikar 2012) R. Polikar, Ensemble Learning. Springer, 2012.

(FengGaoZhangGuo 2018) R. Feng, M. C. Gao, C. Zhang, W. Guo, J. D. Poplawsky, F. Zhang, J. A. Hawk, J. C. Neuefeind, Y. Ren and P. K. Liaw, "Phase Stability and Transformation in a Light-Weight High-Entropy Alloy," *Acta Materialia*, vol. 146, pp. 280-293, 2018.

(ZhangZhangDiaoGao 2016) C. Zhang, F. Zhang, H. Diao, M. C. Gao, Z. Tang, J. D. Poplawsky and P. K. Liaw, "Understanding Phase Stability of Al—Co—Cr—Fe—Ni High Entropy Alloys," *Materials and Design*, vol. 109, pp. 425-433, 2016.

(ShiCollinsFengZhang 2018) Y. Shi, L. Collins, R. Feng, C. Zhang, N. Balke, P. K. Liaw and B. Yang, "Homogenization of AlxCoCrFeNi High-Entropy Alloys with Improved Corrosion Resistance," *Corrosion Science*, vol. 133, pp. 120-131, 2018.

(HemphillYuanWang 2012) M. A. Hemphill, T. Yuan, G. Y. Wang, J. W. Yeh, C. W. Tsai, A. Chuang and P. K. Liaw, "Fatigue Behavior of Al0.5CoCrCuFeNi High Entropy Alloys," *Acta Materialia*, vol. 60, pp. 5723-5734, 2012.

(TangYuanTsai 2015) Z. Tang, T. Yuan, C.-W. Tsai, J.-W. Yeh, C. D. Lundin and P. K. Liaw, "Fatigue behavior of a wrought al 0.5 cocrcufeni two-phase high-entropy alloy," *Acta Materialia*, vol. 99, pp. 247-258, 2015.

(ChenWangSeifiLewandowski 2018) P. Y. Chen, S. Y. Wang, M. Seifi, J. J. Lewandowski, K. A. Dahmen, H. L. Jia, X. Xie, B. L. Chen, J. W. Yeh, C. W. Tsai, T. Yuan and P. K. Liaw, "Fatigue Behavior of High-Entropy Alloys: A Review," *Science China*, vol. 61, no. 2, pp. 168-178, 2018.

(ChlupFintovaHadraba 2019) Z. Chlup, S. Fintová, H. Hadraba, I. Kuběna, M. Vilémová and J. Matějíček "Fatigue Behavior and Crack Initiation in CoCrFeNiMn High-Entropy Alloy Processed by Powder Metallurgy," *Metals,* 2019.

(LyuLeeWangFan 2018) Z. Lyu, C. Lee, S. Y. Wang, X. Fan, J. W. Yeh, and P. K. Liaw, "Effects of Constituent Elements and Fabrication Methods on Mechanical Behavior of High-Entropy Alloys: A Review," *Metallurgical and Materials Transactions A*, Vols. Print ISSN 1073-5623, no. Online ISSN, p. 1-28, 2018.

(ZhangZuoTangGao 2014) Y. Zhang, T. T. Zuo, Z. Tang, M. C. Gao, K. A. Dahmen, P. K. Liaw and Z. P. Lu, "Microstructures and properties of high-entropy alloys," *Progress in Material Science*, vol. 61, pp. 1-93, 2014.

(CorrdesaDjinn 2020) Corrdesa, Djinn, https://www.corrdesa.com/corrosion-djinn/, Feb. 3, 2020.
(Abaqus 2019) Abaqus Ver. 6.8, "The Abaqus C++ API architecture," http://130.149.89.49:2080/v6.8/books/cmd/default.htm?startat=pt05ch10s08.html, Jun. 21 2019.
(ParaView 2019) ParaView, "ParaView for Structural Analysis," https://www.paraview.org/structural-analysis/., Jun. 21 2019.
(OpenFOAM 2019) OpenFOAM, "Free Open Source CFD," http://www.openfoam.org/, Jun. 21, 2019.
(PredictiveEngineering 2019) Predictive Engineering, "Automation and API Programming with FEmap and NX Nastran," https://www.appliedcax.com/support-and-training/training/automation_and_api_programing_with-_femap_and_nx_nastran_partial_notes.pdf, Jun. 21 2019.
(AltairHyperWorks 2019) Altair HyperWorks, "Altair OptiStruct," http://blog.altair.co.kr/wp-content/uploads/2011/03/optistruct_optimization_10-0.pdf, Jun. 21, 2019
(TsaiYeh 2014) M. H. Tsai & J. W. Yeh, "High-entropy alloys: a critical review," *Materials Research Letters*, vol. 2, no. 3, pp. 107-123, 2014.
(Jien-Wei 2006) Y. E. H. Jien-Wei, "Recent progress in high entropy alloys," *Ann. Chim. Sci. Mat*, vol. 31, no. 6, pp. 633-648, 2006.
(YehChenLinChen 2007) J. W. Yeh, Y. L. Chen, S. J. Lin and S. K. Chen, "High-entropy alloys—a new era of exploitation," in *Materials Science forum*, Vol. 560, Trans. Tech. Publications, 2007, pp. 1-9.
(ChenNiuLiLi 2011) X. Q. Chen, H. Niu, D. Li and Y. Li, "Modeling hardness of polycrystalline materials and bulk metallic glasses," *Intermetallics*, vol. 19, no. 9, pp. 1275-1281, 2011.
(FormanMettu 1992) R. G. Forman and S. R. Mettu, "Behavior of Surface and Corner Cracks Subjected to Tensile and Bending Loads in Ti-6Al-4V Alloy," *Fracture Mechanics: 22nd Symposium, Vol. 1* (Eds H. A. Ernst, A. Saxena, D. I. McDowell), vol. ASTM STP 1131, no. American Society for Testing and Materials, Philadelphia, pp. 519-546, 1992.
(SenkovMiracleChaput 2018) O. N. Senkov, D. B. Miracle, K. J. Chaput and J. P. Couzinie, "Development and exploration of refractory high entropy alloys—A review," *Journal of Material Research*, vol. 33, no. 19, pp. 3092-3128, 2018.
(ZhangYangLiaw 2012) Y. Zhang, X. Yang and P. K. Liaw, "Alloy design and properties optimization of high-entropy alloys," *Jom*, vol. 64, no. 7, pp. 830-838, 2012.
(DiaoFengDahmen 2017) H. Diao, R. Feng, K. A. Dahmen and P. K. Liaw, "Fundamental deformation behavior in high-entropy alloys. An overview," *Current Opinion in Solid State and Materials Science*, vol. 21, no. 5, pp. 252-266, 2017.
(GludovatzHohenwaterCatoor 2014) B. Gludovatz, A. Hohenwarter, D. Catoor, E. H. Chang, E. P. George and R. O. Ritchie, "A fracture-resistant high-entropy alloy for cryogenic applications," *Science*, vol. 345, no. 6201, pp. 1153-1158, 2014.
(YehChenLinGan 2014) J. W. Yeh, S. K. Chen, S. J. Lin, J. Y. Gan, T. S. Chin, T. T. Shun, . . . & S. Y. Chang, "Nanostructured high-entropy alloys with multiple principal elements: novel alloy design concepts and outcomes," *Advanced Engineering Materials*, vol. 6, no. 5, pp. 299-303, 2014.
(LeysonHectorCurtin 2012) G. P. M Leyson, L. G. Hector Jr and W. A. Curtin, "First-principles prediction of yield stress for basal slip in Mg—Al alloys," *Acta Materialia*, vol. 60, no. 13-14, pp. 5197-5203, 2012.
(RaoVarvenneWoodward 2017) S. I. Rao, C. Varvenne, C. Woodward, T. A. Parthasarathy, D. Miracle, O. N. Senkov and W. A. Curtin, "Atomistic simulations of dislocations in a model BCC multicomponent concentrated solid solution alloy," *Acta Materialia*, vol. 125, pp. 311-320, 2017.
(VarvenneLuqueCurtin 2016) C. Varvenne, A. Luque and W. A. Curtin, "Theory of Strengthening in FCC High-Entropy Alloys," *Acta Materialia*, vol. 118, pp. 164-176, 2016.
(LeysonCurtinHectorWoodward 2010) G. P. M. Leyson, W. A. Curtin, L. G. Hector J, & C. F. Woodward, "Quantitative prediction of solute strengthening in aluminium alloys," *Nature Materials*, vol. 9, no. 9, p. 750, 2010.
(NöhringCurtin 2018) W. G. Nöhring and W. A. Curtin, "Cross-slip of long dislocations in FCC solid solutions," *Acta Materialia*, vol. 158, pp. 95-117, 2018.
(VarvenneLeyson 2017) C. Varvenne, G. P. M. Leyson, M. Ghazisaeidi, and W. A. Curtin, "Solute Strengthening in Random Alloys," *Acta Materialia*, vol. 124, pp. 660-683, 2017.
(JiangZhaoQianSrolovitz 2019) W. Jiang, Q. Zhao, T. Qian, D. J. Srolovitz and W. Bao, "Application of Onsager's variational principle to the dynamics of a solid toroidal island on a substrate," *Acta Materialia*, vol. 163, pp. 154-160, 2019.
(LiPradeepDengRaabe 2016) Z. Li, K. G. Pradeep, Y. Deng, D. Raabe and C. C. Tasan, "Metastable high-entropy dual-phase alloys overcome the strength-ductility trade-off," *Nature*, vol. 534, no. 7606, p. 227, 2016.
(SarmaDawson 1996) G. B. Sarma and P. R. Dawson, "Texture Predictions Using a Polycrystal Plasticity Model Incorporating Neighbor Interactions," *International Journal of Plasticity*, vol. 12, no. 8, pp. 1023-1054, 1996.
(VanHoutteDelannay 2002) P. Van Houtte, L. Delannay and S. R. Kalidindi, "Comparison of two grain interaction models for polycrystal plasticity and deformation texture prediction," *International Journal of Plasticity*, vol. 18, no. 3, pp. 359-377, 2002.
(SignorelliBertinettiTurner 2009) J. W. Signorelli, M. A. Bertinetti and P. A. Turner, "Predictions of forming limit diagrams using a rate-dependent polycrystal self-consistent plasticity model," *International Journal of Plasticity*, vol. 25, no. 1, pp. 1-25, 2009.
(TothMolinariEstrin 2002) L. S. Toth, A. Molinari and Y. Estrin, "Strain hardening at large strains as predicted by dislocation based polycrystal plasticity model," *Journal of Engineering Materials and Technology*, vol. 124, no. 1, pp. 71-77, 2002.
(BoudifaSaanouniChaboche 2009) M. Boudifa, K. Saanouni and J. L. Chaboche, "A micromechanical model for inelastic ductile damage prediction in polycrystalline metals for metal forming," *International Journal of Mechanical Sciences*, vol. 51, no. 6, pp. 453-464, 2009.
(TangYuanTsaiYeh 2015) Z. Tang, T. Yuan, C. W. Tsai, J. W. Yeh, C. D. Lundin and P. K. Liaw, "Fatigue Behavior of a Wrought A10.5CoCrCuFeNi Two-Phase High-Entropy Alloy," *Acta Materialia*, vol. 99, pp. Pages 247-258, October 2015.
(ThurstonGludovatzHohenwater 2017) K. V. S. Thurston, B. Gludovatz, A. Hohenwarter, G. Laplanche, E. P. George and R. O. Ritchie, "Effect of Temperature on the Fatigue-Crack Growth Behavior of the High-Entropy Alloy CrMnFeCoNi," *Intermetallics*, vol. 88, pp. 65-72, 2017.
(ShuklaWangCottonMishra 2018) S. Shukla, T. Wang, S. Cotton and R. S. Mishra, "Hierarchical Microstructure for Improved Fatigue Properties in a Eutectic High Entropy Alloy," *Scripta Materialia*, vol. 156, pp. 105-109, 2018.

(LiuNeneFrankSinha 2018) K. Liu, S. S. Nene, M. Frank, S. Sinha & R. S. Mishra, "Metastability-Assisted Fatigue Behavior in a Friction Stir Processed Dual-Phase High Entropy Alloy," *Materials Research Letters*, vol. 6, no. 11, pp. 613-619, 2018.

(NeneFrankLiuSinhaMishra 2018) S. S. Nene, M. Frank, K. Liu, S. Sinha, R. S. Mishra, B. McWilliams and K. C. Cho, "Reversed strength-ductility relationship in microstructurally flexible high entropy alloy," *Scripta Materialia*, Vols. 163-167, p. 154, 2018.

(SeifiLiYongLiawLewandrowski 2015) M. Seifi, D. Li, Z. Yong, P. K. Liaw and J. J. Lewandowski, "Fracture Toughness and Fatigue Crack Growth Behavior of As-Cast High-Entropy Alloys," *The Journal of The Minerals, Metals & Materials Society (TMS)*, vol. 67, no. 10, pp. 2288-2295, 2015.

(GaoYehLiawZhang 2016) M. C. Gao, J. W. Yeh, P. K. Liaw and Y. Zhang, High-Entropy Alloys, Springer International Publishing, 2016.

(SangidMaierSehitoglu 2011) M. D. Sangid, H. J. Maier and H. Sehitoglu, "A physically based fatigue model for prediction of crack initiation from persistent slip bands in polycrystals," *Acta Materialia*, vol. 59, no. 1, pp. 328-341, 2011.

(LiLiawGao 2018) W. Li, P. K. Liaw and Y. Gao, "Fracture resistance of high entropy alloys: A review," *Intermetallics*, vol. 99, pp. 69-83, 2018.

(LiZhang 2016) D. Li and Y. Zhang, "The ultrahigh charpy impact toughness of forged AlxCoCrFeNi high entropy alloys at room and cryogenic temperatures," *Intermetallics*, vol. 70, pp. 24-28, 2016.

(SinghShetty 1989) D. Singh and D. K. Shetty, "Fracture toughness of polycrystalline ceramics in combined mode I and mode II loading," *Journal of the American Ceramic Society*, vol. 72, no. 1, pp. 78-84, 1989.

(ShenderovaBrennerOmeltchenko 2000) O.A. Shenderova, D. W. Brenner, A. Omeltchenko, X. Su and L. H. Yang, "Atomistic Modeling of the Fracture of Polycrystalline Diamond," *Physical Review B*, vol. 61, no. 6, p. 3877, 2000.

(LiWangWuLiaw 2018) W. Li, G. Wang, S. Wu and P. K. Liaw, "Creep, fatigue, and fracture behavior of high-entropy alloys," *Journal of Materials Research*, vol. 33, no. 19, pp. 3011-3034, 2018.

(ChenLiXieBrechtl 2018) S. Chen, W. Li, X. Xie, J. Brechtl, B. Chen, P. Li, G. Zhao, F. Yang, J. Qiao and P. K. Liaw, "Nanoscale Serration and Creep Characteristics of Al0.5CoCrCuFeNi High-Entropy Alloys," *Journal of Alloys and Compounds*, vol. 752, pp. 464-475, 2018.

(PraveenKim 2018) S. Praveen and H. S. Kim, "High-Entropy Alloys: Potential Candidates for High-Temperature Applications—An Overview," *Advanced Engineering Materials*, vol. 20, pp. 1-22, 2018.

(MuthupandiKimNaPark 2017) G. Muthupandi, K. R. Lim, Y. S. Na, J. Park, D. Lee, H. Kim, S. Park, Y. S. Choi, "Pile-up and sink-in nanoindentation behaviors in AlCoCrFeNi multi-phase high entropy alloy," *Materials Science & Engineering*, vol. 696, pp. 146-154, 2017.

(WongHellingClark 1988) B. Wong, D. E. Helling, and R. W. Clark, "A creep-rupture model for two-phase eutectic solders," *IEEE Transactions on Components, Hybrids and Manufacturing Technology*, vol. 11, no. 3, pp. 284-290, 1988.

(LiDasgupta 1993) J. Li and A. Dasgupta, "Failure-mechanism models for creep and creep rapture," *IEEE Transactions on Reliability*, vol. 42, no. 3, pp. 339-353, 1993.

(TroparevskyMorrisKent 2015) M. C. Troparevsky, J. R. Morris, P. R. C. Kent, Andrew R. Lupini and G. Malcolm Stocks, "Criteria for Predicting the Formation of Single-Phase High-Entropy Alloys," *Physical Review X*, vol. 5, no. 1, pp. 1-6, 2015.

(FengGaoLeeMathes 2016) R. Feng, M. C. Gao, C. Lee, M. Mathes, T. Zuo, S. Chen, J. A. Hawk, Y. Zhang and P. K. Liaw, "Design of Light-Weight High-Entropy Alloys," *Entropy*, vol. 18, no. 333, pp. 1-21, 2016.

(ZhangZhouLinChen 2008) Y. Zhang, Y. J. Zhou, J. P. Lin, G. L. Chen and P. K. Liaw, "Solid-Solution Phase Formation Rules for Multi-component Alloys," *Advanced Engineering Materials*, vol. 10, no. 6, pp. 534-538, 2008.

(GaoNgLuLiu 2011) S. Guo, C. Ng, J. Lu and C. T. Liu, "Effect of Valence Electron Concentration on Stability of FCC or BCC Phase in High Entropy Alloys," *Journal of Applied Physics*, vol. 109, no. 10, pp. 103505, https://doi.org/10.1063/1.3587228, 2011.

(CodeBurst 2019) codeburst.io, "Using python script for data ETL," [Online]. Available: https://codeburst.io/using-python-script-for-data-etl-53138c567906. [Accessed 14 Jan. 2019].

(Qt 2019) Qt 5.12, "Qt SQL," [Online]. Available: http://doc.qt.io/qt-5/qtsql-index.html. [Accessed 14 Jan. 2019].

(TensorFlow 2020) TensorFlow, https://www.tensorflow.org/, [Accessed 27 Jan. 2020].

(SciKit-Learn 2020) SciKit-Learn, https://scikit-learn.org/stable/, [Accessed 27 Jan. 2020].

(CitrineResearch 2019) Citrine Research, "Resources", https://citrination.org/learn/citrination-community-resources/. [Accessed 4 Feb. 2019].

(CitrineResearch 2019) Citrine Informatics, https://citrine.io/, Accessed 4 Feb. 2019.

(OPTiMaDe 2020) OPTiMaDe, http://www.optimade.org/. Accessed 15 Jan. 2020.

(CHIMaD 2020) Polymer Property Predictor and Database, http://pppdb.uchicago.edu. Accessed 15 Jan. 2020.

(NISTmgi 2019) NIST, "Materials Genome Initiative," https://www.nist.gov/mgi, Aug. 20, 2019.

(NISTCalPhad 2019) NIST, "CALPHAD Data Informatics," https://www.nist.gov/programs-projects/calphad-data-informatics, Aug. 21, 2019.

(NistAiUncertainty 2019) NIST, "AI/ML for Data Extraction and Uncertainty Predictions," [Online]. Available: https://www.nist.gov/programs-projects/aim1-data-extraction-and-uncertainty-predictions, Accessed 20 Aug. 2019.

(Thermo-Calc 2014) L. Kjellqvist, J. Brattberg, A. Jansson and H. Mao, "A Thermodynamic Database for Simulation of CMAS and TBC Interactions", Thermal Barrier Coatings IV, An ECI Conference Series, Irsee Germany, May 2014.

(CompuTherm 2020) Software Overview, https://computherm.com/?docs=documentations/software-overview, Accessed 28 Jan. 2020.

(QuesTek 2020) QuesTek Innovation LLC, Patents, https://www.questek.com/patents.html, Accessed 28 Jan. 2020.

(TernaryPlot2020) Wikipedia, "Ternary Plot", https://en.wikipedia.org/wiki/Ternary_plot, Accessed 28 Jan. 2020.

(VASP 2020) University of Vienna, "VASP", https://cmp.univie.ac.at/research/vasp/, Accessed 28 Jan. 2020.

(ZhangZhou 2008) Y. Zhang, Y. J. Zhou, J. P. Lin, G. L. Chen and P. K. Liaw, "Solid Solution Phase Formation Rules for Multi-component Alloys," Advanced Engineering Materials, pp. 534-538, 2008.

(CouzinieSenkovMiracle 2018) J. P. Couzinie, O. N. Senkov, D. B. Miracle and G. Dirras, "Comprehensive data compilation on the mechanical properties of refractory high-entropy alloys," *Data in Brief*, vol. 21, pp. 1622-1641, 2018.

(GorsseNguyenSenkovMiracle 2018) S. Gorsse, M. H. Nguyen, O. N. Senkov and D. B. Miracle, "Database on the mechanical properties of high-entropy alloys and complex concentrated alloys," *Data in Brief*, vol. 21, pp. 2664-2678, 2018.

(O'MaraMeredigMichel 2016) J. O'Mara, B. Meredig and K. Michel, "Materials Data Infrastructure: A Case Study of the Citrination," *The Journal of The Minerals, Metals & Materials Society*, vol. 68, no. 8, p. 2031-2034, 2016.

(LiuKomarasamyGwalani 2019) K. Liu, M. Komarasamy, B. Gwalani, S. Shukla and R. S. Mishra, "Fatigue behavior of ultrafine grained triplex Al0.3CoCrFeNi high entropy alloy," *Scripta Materialia*, vol. 158, pp. 116-120, 2019.

(JiaoSimKomarasamyMishra 2018) Q. Jiao, G. D. Sim, M. Komarasamy, R. S. Mishra, P. K. Liaw and J. A. El-Awady, "Thermo-mechanical response of single-phase face-centered-cubic AlxCoCrFeNi high-entropy alloy microcrystals," *Materials Research Letters*, vol. 6, no. 5, pp. 300-306, 2018.

(LyuFanLeeWang 2018) Z. Lyu, X. Fan, C. Lee and S. Y. Wang, "Fundamental understanding of mechanical behavior of high-entropy alloys at low temperatures: A review," *Journal of Materials Research*, vol. 33, no. 19, pp. 2998-3010, 2018.

(ChenTongLiaw 2018) S. Chen, Y. Tong, P. K. Liaw, "Additive Manufacturing of High-*Entropy* Alloys: A Review," *Entropy*, vol. 20, no. 12, p. 937, 2018.

(WangVoisinMcKeownYe 2018) Y. M. Wang, T. Voisin, J. T. McKeown, J. Ye, N. P. Calta, Z. Li, Z. Zeng, Y. Zhang, W. Chen, T. T. Roehling, R. T. Ott, M. K. Santala, P. J. Depond, M. J. Matthews, A. V. Hamza and T. Zhu, "Additively manufactured hierarchical stainless steels with high strength and ductility," *Nature Materials*, vol. 17, pp. 63-73, January 2018.

(ZhuNguyenNgAnLiao 2018) Z. G. Zhu, Q. B. Nguyen, F. L. Ng, X. H. An, X. Z. Liao, P. K. Liaw, S. M. L. Nai, J. Wei, "Hierarchical microstructure and strengthening mechanisms of a CoCrFeNiMn high entropy alloy additively manufactured by selective laser melting," *Scripta Materialia*, vol. 154, pp. 20-24, 2018.

(ZhuNgQiaoLiawChen 2018) Z. G. Zhu, F. L. Ng, J. W. Qiao, P. K. Liaw, H. C. Chen, S. M. L. Nai, J. Wei, G. J. Bi, "Interplay between microstructure and deformation behavior of a laser-welded CoCrFeNi high entropy alloy," *Materials Research Express*, no. http://iopscience.iop.org/article/10.1088/2053-1591/aafabe/meta, Accepted Manuscript online 21 Dec. 2018.

(SteingrimssonJonesKisialiou 2018) B. Steingrimsson, R. Jones, M. Kisialiou and K. Yi, "Decisions with Big Data". USA Patent Applications 16,182,389, 6 Nov. 2018.

(Steingrimsson 2017) B. Steingrimsson, "Digital Ecosystem for Engineering Design". filed on patent Ser. No. 15/613, 183, 3 Jun. 2017.

(DataScienceCentral 2018) Data Science Central, Artificial Intelligence vs. Machine Learning vs. Deep Learning, https://www.datasciencecentral.com/profiles/blogs/artificial-intelligence-vs-machine-learning-vs-deep-learning, 2018.

(LeviHutchinson 2012) C. G. Levi, J. W. Hutchinson, M-H Vidal-Setif and C. A. Johnson, "Environmental Degradation of Thermal-Barrier Coatings by Molten Deposits," *MRS Bulletin*, vol. 37, no. 10, pp. 932-941, October 2012.

SUMMARY OF THE INVENTION

1. Framework for an Engine, Employing Simple Prediction Models when Suitable

As opposed to applying machine learning, narrowly defined in terms of neural networks (single-layer or multi-layer), Bayesian graphical models, support vector machines or decision trees, to the identification of alloys or composites of interest, we reformulate the task in the broader context of engineering optimization. We recommend picking an optimization technique suitable for the application at hand and the data available. But we certainly include ML in that consideration.

In case of identification of HEA compositions yielding high tensile strength, the prediction engine is capable of yielding consistency amongst (a) prediction of HEA composition with attractive tensile strength, (b) empirical rules of thermodynamics (ZhangZhou 2008), (FengGaoLeeMathes 2016), and (c) experimental results, despite limited data being available, and the corresponding selection of a simple prediction algorithm (multi-variate regression).

In the case of prediction of fatigue resistance, the innovation demonstrates an indirect approach for predicting HEA compositions yielding attractive fatigue resistance, despite again limited fatigue data being available. This is a method that harvests a correlation identified between fatigue resistance and the ultimate tensile strength.

2. Framework for a Generic Prediction Engine, One Supporting Inverse Design Representations The prediction engine entails an innovative framework for the application of machine learning to the development of high-entropy alloys with desired properties. We present a framework for "forward" predicting the composition, yield strength, material ductility, fatigue, fracture toughness, and creep of alloys. For each output property of interest, we identify the corresponding driving factors. These driving factors may include the material composition, heat treatment, process, microstructure, temperature, strain rate, environment, or testing mode. We then carry out the "forward" prediction through a customized averaging process in the parameter space comprising the input parameters.

"Backward prediction" (identification of candidate compositions) is accomplished through an inverse design framework, one that identifies the candidate compositions to test next, based on a set of property specifications and design goals. Through a sequential learning workflow, the inverse design framework is used to identify candidate compositions. Data corresponding to these candidate compositions is then used to retrain the model, presumably leading to iterative refinements and convergence.

3. Framework for an Engine Supporting Advanced Physics-Based Prediction Models

The invention presents method and apparatus for employing physics-based models, i.e., models that account for physical dependencies, and factor in the underlying physics as a priori information, during the prediction process, for the purpose of making the most of the usually limited input data available.

In case an ANN is deemed suitable for the application at hand, the invention can employ custom kernel functions consistent with the underlying physics, for the purpose of attaining tighter coupling, better prediction, and extracting the most out of the—usually limited—input data available.

There can be great benefits derived from combining ML with physics-based modeling approaches for alloys and composites, for improved prediction accuracy. Such modeling approaches can offer physical insight as unexplored regions of the composition space are investigated. These approaches may include thermo-dynamics, first principle effects, empirical rules, mesoscale models, models for dislocation dynamics and slip bands to help with accurate prediction of stress/life curves, or feature representations for distinguishing between hot corrosion attacks.

4. Framework for an Engine Utilizing Statistical Prediction Models

One embodiment of the invention describes a comprehensive toolset for predicting properties, such as the fatigue life, of flight-critical metallic components fabricated by AM. To account for the complex underlying process, we present a ML framework for predicting fatigue properties. The framework is a generalization (augmentation) of a Statistical Fatigue Life model originally proposed by one of the authors. The comprehensive toolset helps predict the fatigue life of metallic components fabricated by additive manufacturing with accuracy superior to that of existing tools.

The comprehensive toolset systematically accounts for the wide variety of sources (over 100) that can impact the fatigue life of AM metallic components.

Through sensitivity analysis, provided by the augmented Statistical Fatigue Life model, the toolset provides feedback for manufacturing. The tool can provide feedback on the impact that variations in given input parameters have on the fatigue life.

Another embodiment of the invention describes a predictive methodology for fatigue properties of metallic AM components, one relating material and processing induced imperfections. The predictive methodology for fatigue properties of metallic AM components relates material and processing induced imperfections.

DESCRIPTION OF THE DRAWINGS

FIG. 9 presents qualitative comparison between cost of additive manufacturing and conventional production.

FIG. 13 also illustrates how prediction of material properties of alloys can be extended to matrix composites.

FIG. 23 presents an example, where a linear prediction model is derived from Data Set A in Table 13 through linear regression analysis.

FIG. 24 presents an example, where a linear prediction model is derived from Data Set B in Table 13 through linear regression analysis.

FIG. 25 presents an example, where a linear prediction model is derived from Data Set C in Table 13 through linear regression analysis.

FIG. 26 captures Step 2 in the prediction methodology outlined in FIG. 22.

FIG. 36 presents regression analysis applied to the Data Sets from Examples A, B and C.

FIG. 40 (bottom) shows a heating strategy, one that uses a melting beam of scan speed vi and a heating beam of v2 which is much faster and irradiates the layer multiple times while beam 1 melts the tracks.

DETAILED DESCRIPTION OF THE PREFERRED EMBODIMENTS

1. Definitions

Figure 1:
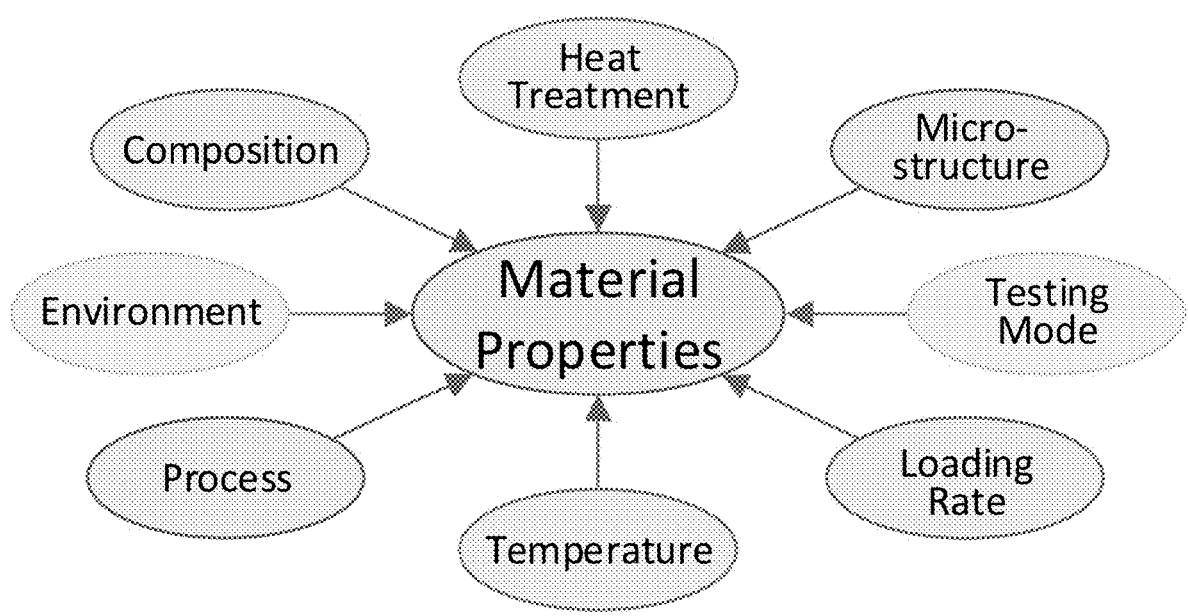
FIG. 1 presents the primary factors impacting the material properties of alloys, such as high-entropy alloys. The material properties considered include material hardness, yield strength, ultimate strength, plasticity, fatigue, fracture toughness and creep. The process part may include fabrication and machining processes.

Table 5 captures the primary acronyms used in the patent.

TABLE 5

Summary of the primary definitions and acronyms.

| Name | Definition |
|---|---|
| AM | Additive Manufacturing |
| ANN | Artificial Neural Network |
| API | Application Program Interface |
| CCA | Complex, Concentrated Alloy (or Canonical Component Analysis) |
| CCE | Carbon Conversion Efficiency |
| CFD | Computational Fluid Dynamics |
| CMAS | Calcium Magnesium Alumino Silicate |
| CMC | Ceramic Matrix Composite |
| DED | Direct Energy Deposition |
| DFT | Density Functional Theory |
| DMD | Direct Metal Deposition |
| DMLS | Direct Metal Laser Sintering |
| EBM | Electron Beam Melting |
| GE | General Electric |
| HEA | High-Entropy Alloy |
| HIP | Hot Isostatic Pressing |
| ICME | Integrated Computational Materials Engineering |
| IDE | Integrated Development Environment |
| IM | Intermetallic |
| JPL | Jet Propulsion Laboratory |
| JSON | JavaScript Object Notation |
| k-NN | k Nearest Neighbors |
| LENS | Laser Engineered Net Shaping |
| LMD | Laser Metal Deposition |
| MIG | Metal Inert Gas |
| ML | Machine Learning |
| MME | Mechanical and Materials Engineering |
| MPEA | Multi-Principal Element Alloy |
| NIST | National Institute of Standards and Technology |
| ODF | Oriental Distribution Function |
| PBF | Powder-Bed Fusion |
| PMC | Polymer Matrix Composite |
| PSU | Portland State University |
| RHEA | Refractory High-Entropy Alloy |
| SDK | Software Development Kit |
| SLM | Selective Laser Melting |
| SLS | Selective Laser Sintering |
| SMD | Shaped Metal Deposition |
| SPS | Spark Plasma Sintering |
| SS | Solid-Solution |
| TBC | Thermal Barrier Coating |
| TIG | Tungsten Inert Gas |
| UTS | Ultimate Tensile Strength |
| VASP | Vienna Ab initio Simulation Package |
| WAAM | Wire and Arc Additive Manufacturing |

We define artificial intelligence as the use of computers to mimic the cognitive functions of humans. When machines carry out tasks based on algorithms in an "intelligent" manner, that is Al. Artificial intelligence is a broader concept than machine learning (DataScienceCentral 2018).

We define machine learning as a subset of Al that focuses on the ability of machines to receive a set of data and learn for themselves, and change algorithms as they learn more about the information that they are processing (DataScienceCentral 2018).

We refer to deep learning as a subset of machine learning. We define deep learning in terms of "deep neural networks", i.e., neural networks comprising of two or more layers. Deep learning networks need to see large quantities of items in order to be trained (DataScienceCentral 2018).

Supervised learning is a data mining task that involves inference of a function from labeled training data.

Unsupervised learning is a type of machine learning algorithm used to draw inferences from datasets consisting of input data without labeled responses.

Reinforcement learning is an area of machine learning concerned with how software agents ought to take actions in an environment so as to maximize some notion of cumulative reward.

2. Best Mode of the Invention

FIG. 10, FIG. 14, FIG. 15, FIG. 18, FIG. 22, FIG. 26, FIG. 33 and FIG. 35 capture the best mode contemplated by the inventors, according to the concepts of the present invention.

3. System Structure at a High Level

Figure 10:
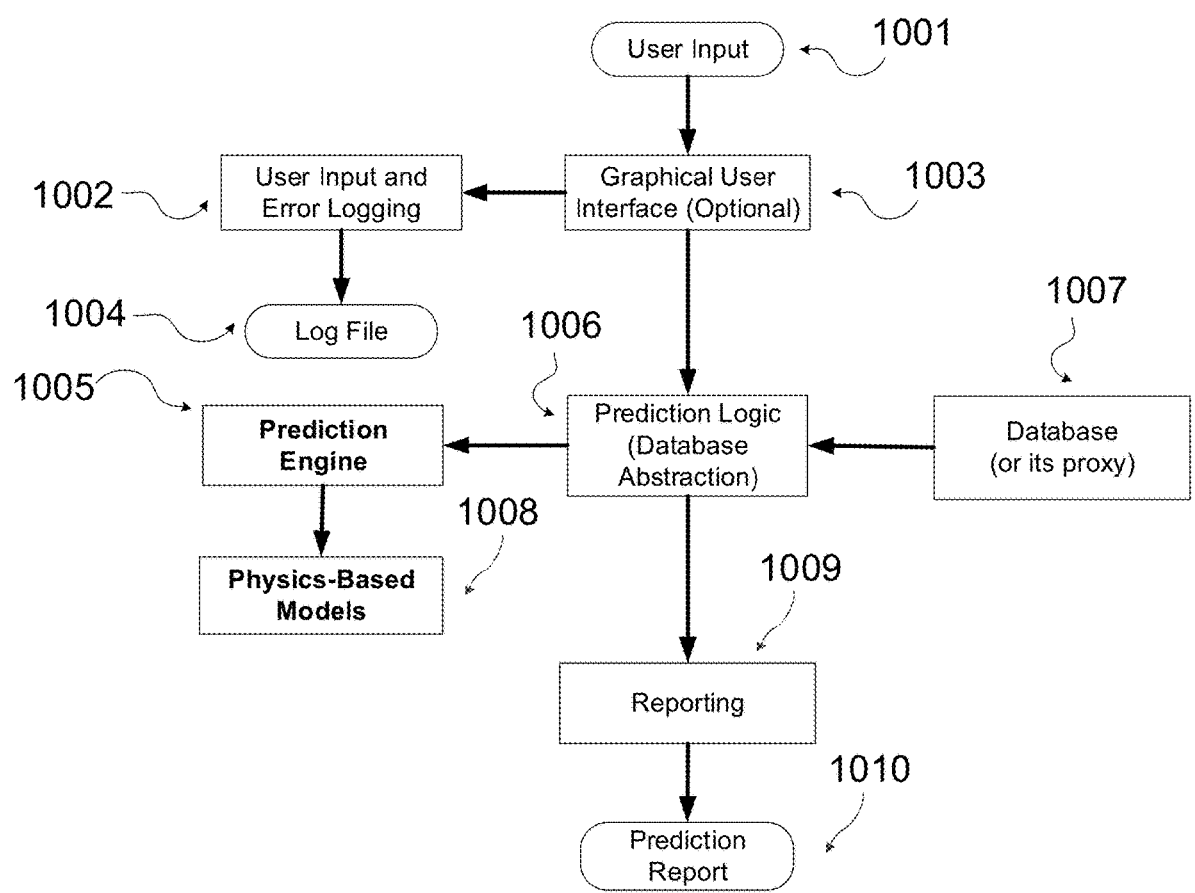
FIG. 10 presents a master architecture (a dependency diagram), one capturing the prediction engine.
Figure 11:
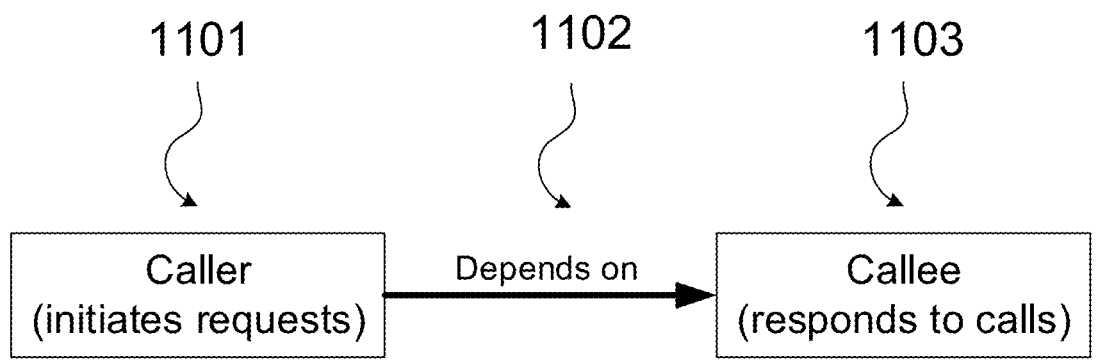
FIG. 11 presents the relationship, per the dependency diagram in FIG. 10 between the caller, that initiates a request, and the callee, that responds to a call.

FIG. 10 presents a dependency diagram for the overall system architecture. The architecture has been devised largely based on the requirements for the prediction engine. While the architecture may come across as simplistic, it has been artfully crafted such as not to contain any loops. This offers great value in terms of significantly expediting the process of confining the source of certain behavior (desired or undesired) to given modules.

With the graphical user interface and prediction logic being optional, the architecture supports both embedded (plugin or web service) and integrated applications of the prediction engine.

4. User Interface

4.1 General Consideration

The GUI is assumed to be based on the traditional Model-View-Controller model (Steingrimsson 2017). The GUI may be integrated into a host application, may be executed through a plugin, or may run through a web interface.

4.2 Specific Example: Prediction of Fatigue Life of AM Components

Given the large number of parameters that can impact the fatigue life of AM components, it is important to prioritize these parameters, based on importance to the customer, and systematically organize while still keeping the user interface efficient and user friendly.

5. Database System

5.1 General Assumptions

The typical use case assumes a relational database, such as SQL.

In order to be useful, the data needs to be collected into a single repository and have consistent format.

An in-memory implementation of the database stores as inputs vectors, k's, capturing the sources affecting the output quantity of interest, y. The in-memory database also stores the aforementioned output quantity. For further information, refer to the generic system model in Eq. (1). It is preferable that the database supports an in-memory mode. The prediction engine may require millions of comparative operations. Without an in-memory mode, every comparison may require an I/O call. This may introduce significant latency.

5.2 Extendable Solution for Importing Content from Disparate Databases: SQL and JSON A key challenge in applying ML algorithms to materials science data is that data can come in many formats. Determining how to featurize and utilize different materials data formats so that prior data can be used as training data for ML algorithms can be difficult. Feature engineering, including extraction, transformation, and selection, is critical for improved ML accuracy. To fully realize data analytics and machine learning tools for materials development, it may be necessary to transform various raw data inputs into information-rich features suitable for modeling. Hence, it may be necessary to unify disparate data sets into a consistent format that can be utilized by the prediction engine.

A SQL server may be an ideal solution for supporting importing of data from disparate databases, for use by the prediction engine. A SQL server, such as a MySQL server, would allow one to import and translate many data types. It would enable one to import data from any database supporting the SQL language, search for data of interest, export into a standardized format, and import into the prediction engine.

JSON data is represented in a logical, organized and easy-to-access manner. JSON can contain multiple levels of objects, arrays and various field data. JSON is supported in order to provide access to open materials data bases, such as the Citerine's JSON-based database (CitrineResearch 2019). Alternatively, the data may originate from the NIST CAL-PHAD Data Informatics databases (NISTCalPhad 2019), the CHIMAD Polymer Property Predictor Database (CHIMaD 2020), databases associated with the Materials Genome Initiative (NISTmgi 2019) or OPTiMaDe (OPTiMaDe 2020). Both Citrine and OPTiMaDe offer APIs providing convenient access for users.

Figure 12:
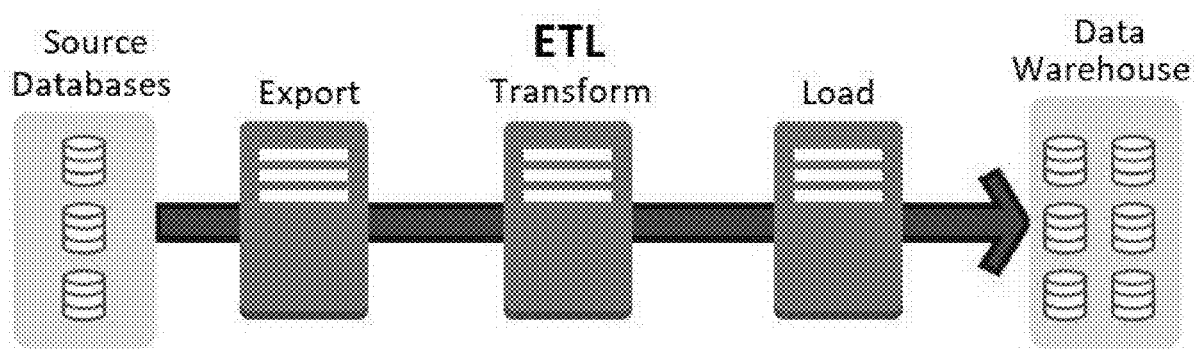
FIG. 12 presents the essential mechanism of Export, Transform and Load.

5.3 Mechanism for Supporting Multiple Data Formats: ETL—Extract, Transform and Load ETL is a generic principle representing three database functions (extract, transform and load) that are combined into a single tool to pull data out of one database and place into another database (see FIG. 12). Extract is the process of reading from a database. In this stage, the data is collected, often from multiple and different types of sources. Transform is the process of converting the extracted data from its previous form into the form it needs to be in so that it can be placed into another database. Transformation occurs by using rules or lookup tables or by combining the data with other data. Load is the process of writing the data into the target database. Traditional symmetric multi-processing data warehouses use an ETL process for loading the data. Ref. (CodeBurst 2019) shows how to Extract data from mysql, sql-server or firebird, Transform the data, and then Load into a SQL server (a data warehouse) using python 3.6.

5.4 Preparation of Data Sets for Prediction—Implications of Incomplete Data Ref (AgrawalDeshpande 2014) suggests that one may be able to employ standard, off-the-shelf, free or open-source machine learning libraries, such as TensorFlow (TensorFlow 2020) or scikit-learn (SciKit-Learn 2020), and obtain reasonably accurate prediction results, assuming one has access to data sets that are clean, usable, abundant and trustworthy (and do not contain outliers).

However, in practice material scientists usually find themselves operating in the realm of limited data.

Hence, in practice, it may be of importance to incorporate physics-based models, in order to extract the most out of the (limited) data sets available.

6. Prediction Database Logic

The prediction database logic serves as an interface, or abstraction layer, between the prediction engine and the database. The prediction database logic can provide the ability to store internal data structures in memory and later archive in a data base (e.g., by saving on a hard disk drive or a flash drive). The prediction database logic can represent data in a format convenient to the prediction engine.

7. Prediction Engine

7.1 General Approach to Prediction of Properties and Feature Sets for Compositions of Interest FIG. 10-FIG. 11 and FIG. 13-FIG. 17 summarize the general approach for predicting feature sets (or properties) for alloy or composite compositions of interest.

1. Structure of a Generic System Model
We assume a generic system model:

$$\tilde{y} = f(\tilde{x}). \tag{1}$$

TABLE 6

Recommended features for prediction of composition of RHEA and parameters of powder bed AM.

| Abbrev | Category | Details |
|---|---|---|
| Cr | Composition | % Chromium |
| Hf | | % Hafnium |

TABLE 6-continued

Recommended features for prediction of composition of RHEA and parameters of powder bed AM.

| Abbrev | Category | Details |
|---|---|---|
| Mn | | % Manganese |
| Mo | | % Molybdenum |
| Nb | | % Niobium |
| Os | | % Osmium |
| Re | | % Rhenium |
| Rh | | % Rhodium |
| Ru | | % Ruthenium |
| Ta | | % Tantalum |
| Tc | | % Technetium |
| Ti | | % Titanium |
| V | | % Vanadium |
| W | | % Tungsten |
| Zr | | % Zirconium |
| Al | | % Aluminum |
| Temp | Heat Treatment | Temperature |
| HeatTime | | Treatment time |
| HeatEnvir | | Heat treatment environment |
| LoadRate | Loading Rate | $10^{-5}$ sec$^{-1}$- $10^{6}$ sec$^{-1}$ |
| ColdRoll | Environ-ment | Cold rolling |
| HotRoll | | Hot rolling |
| FCC | Micro-structure | Face centered cubic structure |
| BCC | | Body centered cubic structure |
| HCP | | Hexagonal closed packed structure |
| Precip | | Precipitate |
| Tension | Testing Mode | Tension |
| Compres | | Compression |
| Bending | | Bending |
| Torsion | | Torsion |
| PowdBT | Temperature | Powder bed temp |
| PowdFT | | Powder feeder temp |
| ElevatT | | Elevated temp |
| LaserPow | Process | Laser power |
| SpotSize | | Spot size |
| PulseDur | | Pulse duration |
| PulseFreq | | Pulse frequency |
| ScanSpd | | Scan speed |
| HatchDist | | Hatch distance |
| ScanPattn | | Scan pattern |
| PartShape | | Particle shape |
| PartSize | | Particle size |
| PartDist | | Particle distribution |

TABLE 7

Recommended features for prediction of fatigue endurance limit of HEAs.

| Abbrev. | Category | Details |
|---|---|---|
| Ag | Composition | % Silver |
| Al | | % Aluminum |
| Au | | % Gold |
| B | | % Boron |
| C | | % Carbon |
| Co | | % Cobolt |
| Cr | | % Chromium |
| Cu | | % Copper |
| Dy | | % Dysprosium |
| Fe | | % Iron |
| Gd | | % Gadolinium |
| Ge | | % Germanium |
| Hf | | % Hafnium |
| Li | | % Lithium |
| Lu | | % Lutetium |
| Mn | | % Manganese |
| Mo | | % Molybdenum |
| Nb | | % Niobium |
| Nd | | % Neodymium |
| Ni | | % Nickel |
| P | | % Phosphorus |
| Pd | | % Palladium |
| Rh | | % Rhodium |
| Ru | | % Ruthenium |
| S | | % Sulphur |
| Sc | | % Scandium |
| Si | | % Silicon |
| Sn | | % Tin |
| Ta | | % Tantalum |
| Tb | | % Terbium |
| Ti | | % Titanium |
| Tm | | % Thulium |
| V | | % Vanadium |
| W | Composition | % Tungsten |
| Y | | % Yttrium |
| Zn | | % Zinc |
| Zr | | % Zirconium |
| Temp | Heat Treatment | Temperature |
| HeatTime | | Heat treatment time |
| HeatEnvir | | Heat treatment environment |
| LoadRate | Loading Rate | $10^{-5}$ sec$^{-1}$- $10^{6}$ sec$^{-1}$ |
| FCC | Micro-structure | Face centered cubic structure |
| BCC | | Body centered cubic structure |
| HCP | | Hexagonal closed packed structure |
| Precip | | Precipitate |
| Tension | Testing Mode | Tension |
| Compres | | Compression |
| Bending | | Bending |
| Torsion | | Torsion |
| CryoT | Temperature | Cryogenic temp |
| RoomT | | Room temperature |
| ElevatT | | Elevated temp |
| DropCast | Process | Drop casting |
| AddMfg | | Additive manufacturing |
| Powder | | Powder metallurgy |
| Sputter | | Sputtering |
| VolPreci | | Vol. % of precipitate |
| SizePrec | | Size of precipitate |
| ShapePre | | Shape of precipitate |
| ColdRoll | Environment | Cold rolling |
| HotRoll | | Hot rolling |

The input vector, $\tilde{x}$, can be considered as the definition of a feature set comprising of parameters related to the composition, defect properties, heat treatment, and manufacturing, essentially all the sources that impact the output quantity of interest, $\tilde{y}$. The transformation, $f(\cdot)$, can be a non-linear function of the input, x. We present artificial intelligence, regression analysis and supervised learning as options to construct (train) the system model.

Figure 15:
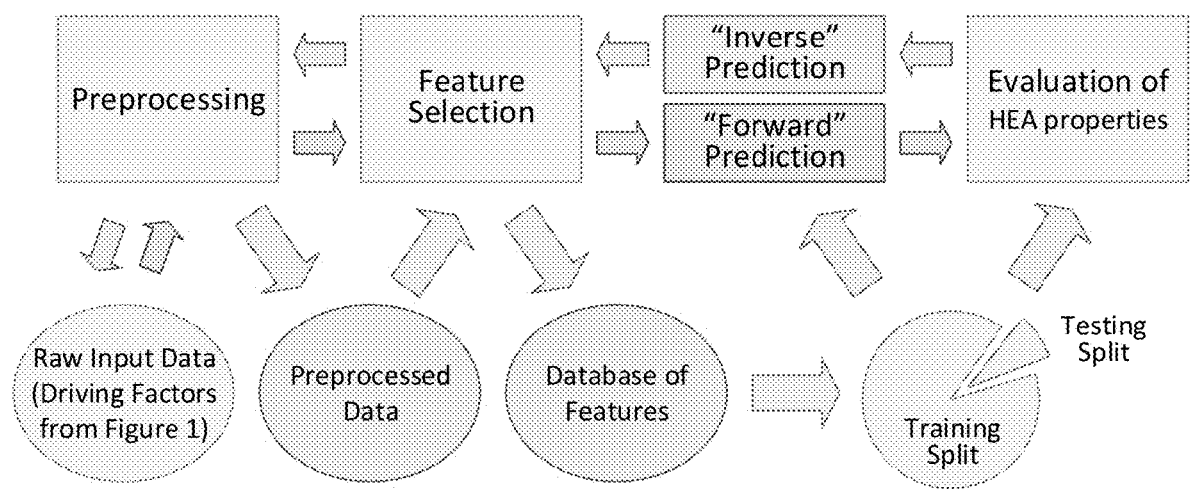
FIG. 15 presents a high-level approach to machine learning with knowledge discovery and data mining.

2. Key Characteristics of "Forward" and "Backward" Prediction 2.1 Quantity Predicted We "forward" predict the observed properties, such as the properties listed in FIG. 1, FIG. 2, FIG. 3 and FIG. 13. We "backward" predict the properties comprising the feature set, as shown in FIG. 15. For examples of representative feature sets, refer to Table 6 and Table 7.

2.2 Preprocessing

For fair comparison, we normalize the input data, as appropriate. In case of the endurance limit, $S_e$, we normalize with the ultimate tensile strength, UTS:

$$S_{e,norm} = \frac{S_e}{UTS}. \quad (2)$$

2.3 Feature Selection

We derive the features selected from the driving factors listed in FIG. 1, FIG. 2, FIG. 3 and FIG. 13. Table 6 presents a sample feature selection suitable for identification of RHEAs for high-temperature applications. Note the feature set also captures the AM processing parameters. Hence, the feature set correlates material functionality both with material compositions and manufacturing process conditions. Table 7 presents another representative sample of feature selection suitable for prediction of fatigue endurance limit of HEAs.

3. Approach to Building a Generic System Model Through "Forward" Prediction

We present a scalable solution for deriving the system model, one that accounts for the application at hand and the input data available. In the case of a small set of input data, we present regression as a suitable tool for deriving (constructing) the system model. But for a large set of input data, say, hundreds, thousands, or millions of (x, y) duplets, we present feed-forward neural networks as a suitable tool for constructing the system model.

Figure 5:
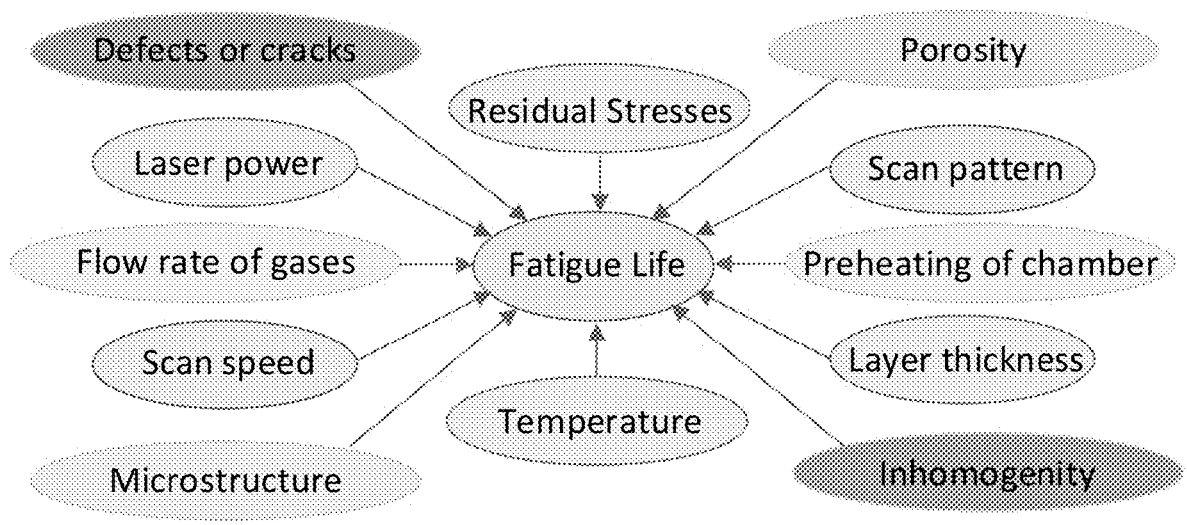
FIG. 5 presents a high-level overview of primary sources contributing to the fatigue life of additively manufactured metallic components.
Figure 6:
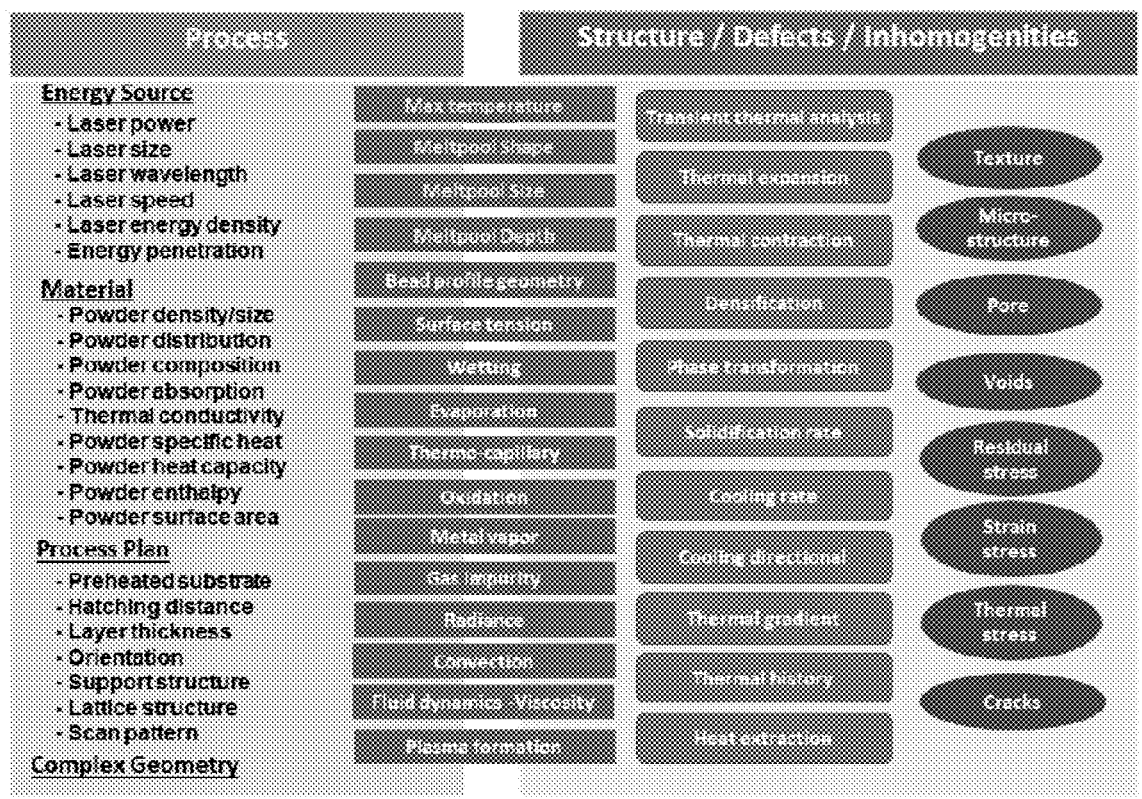
FIG. 6 presents an overview more complete than FIG. 5, but still not comprehensive, of the sources contributing to the fatigue life of AM metallic components.
Figure 7:
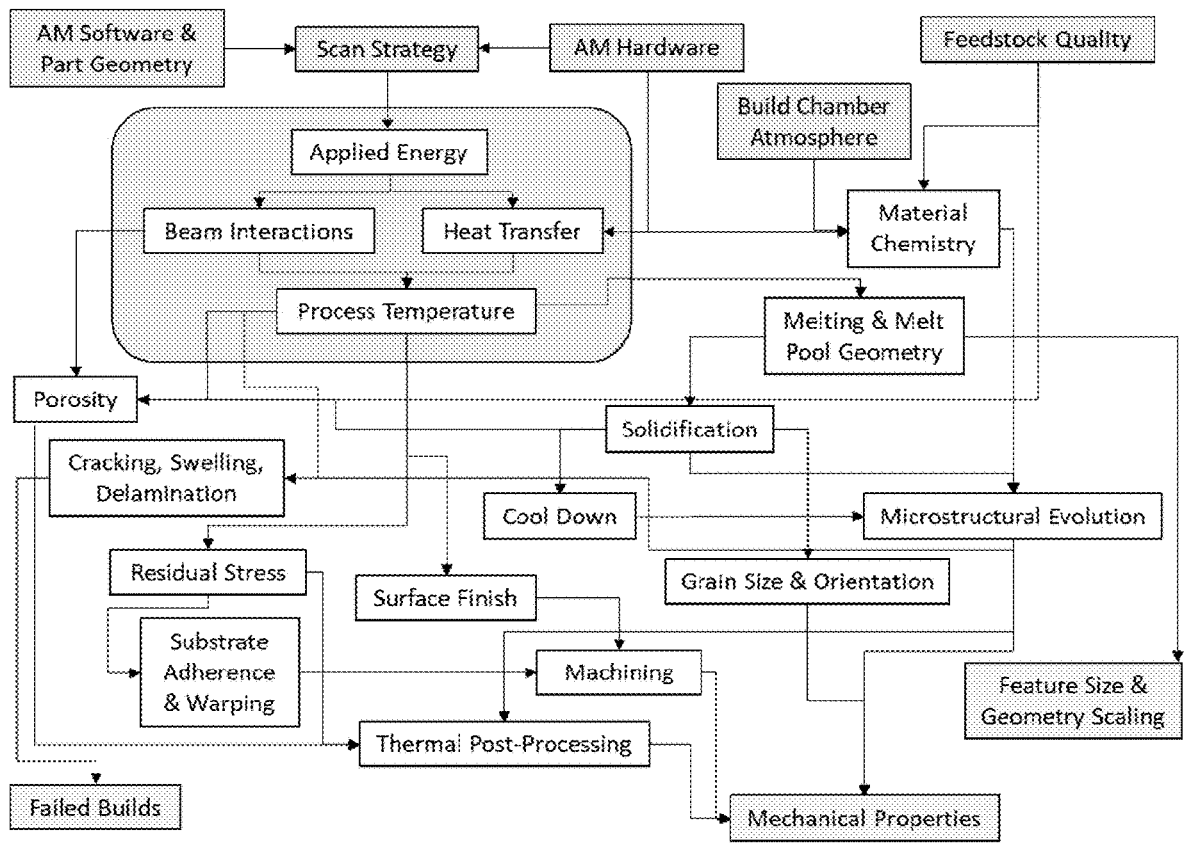
FIG. 7 depicts a processing map for metal additive manufacturing.

Our approach is founded in part on observations of Agrawal et. al. (AgrawalDeshpande 2014). Table 2 and FIG. 5 of (AgrawalDeshpande 2014) illustrate that there is at most a few percentage difference between the techniques applied to predict the fatigue strength of stainless steel. Table 2 of (AgrawalDeshpande 2014) shows that both the simple linear regression and pace regression yield the coefficient of determination, $R^2$, of 0.963, while the artificial neural network, a traditional ML approach, results in $R^2$ of 0.972.

4. More on "Forward" Prediction: Review of Predictive Modeling Techniques Considered The predictive modeling techniques considered include, but are not limited to, linear regression, pace regression, regression post non-linear transformation of select input variables, robust fit regression, multivariate polynomial regression (including quadratic regression), decision tables, support vector machines, artificial neural networks, reduced error pruning trees and M5 model trees.

4.1. Statistical Regression

For background information on statistical regression, refer to (SteingrimssonJonesKisialiou 2018).

4.2. k-Nearest Neighbor Averaging

Figure 13:
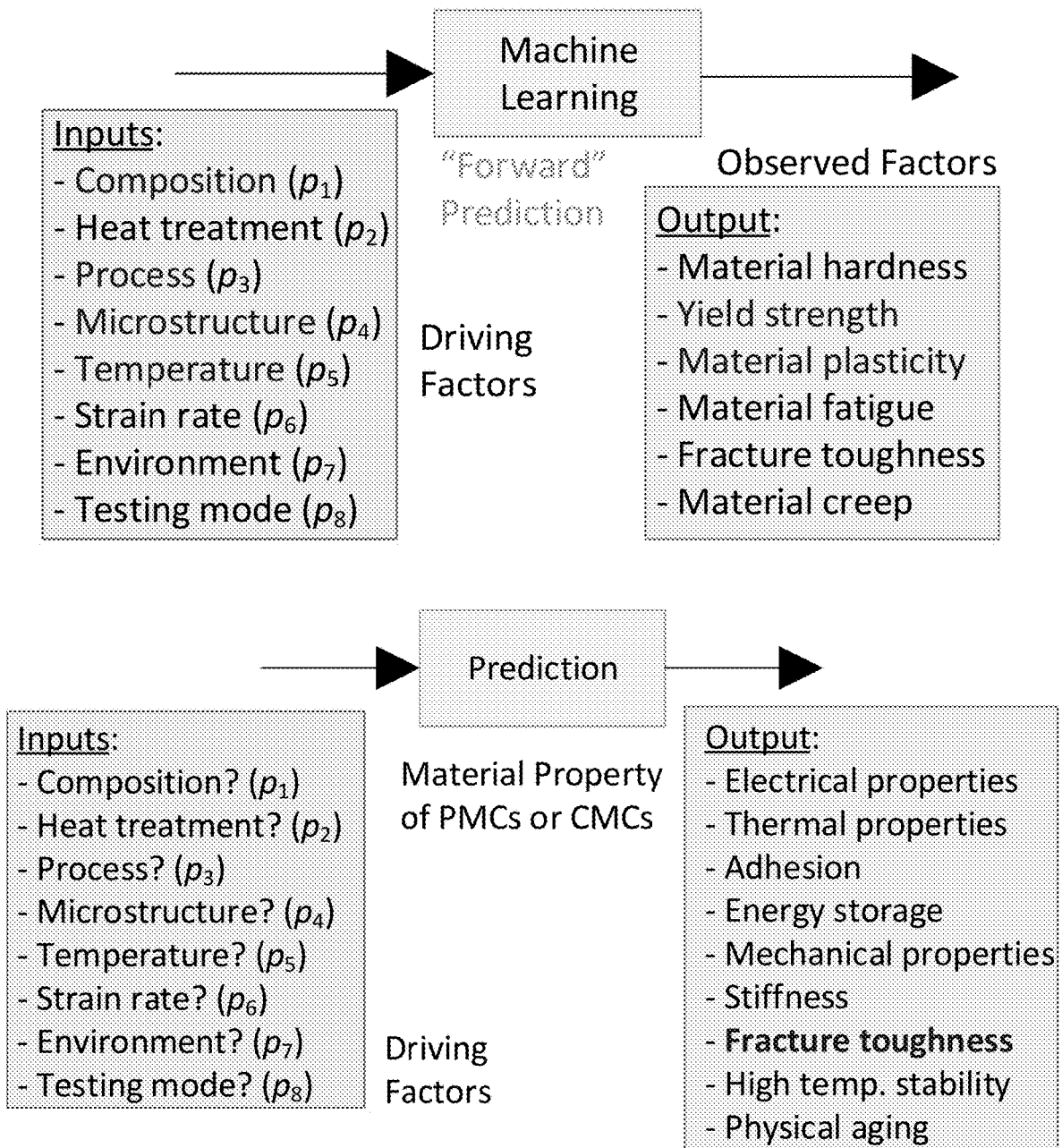
FIG. 13 outlines the high-level approach to "forward" prediction of material properties of alloys, such as HEAs.

FIG. 13 present a simple framework for predicting the observed properties for alloys or composites of interest. For each observed property of interest, we identify the corresponding driving factors. These input factors may include the material composition, heat treatment, process, microstructure, temperature, strain rate, environment, and testing mode. We then carry out the prediction through a customized averaging process in the space comprising the input parameters.

Figure 14:
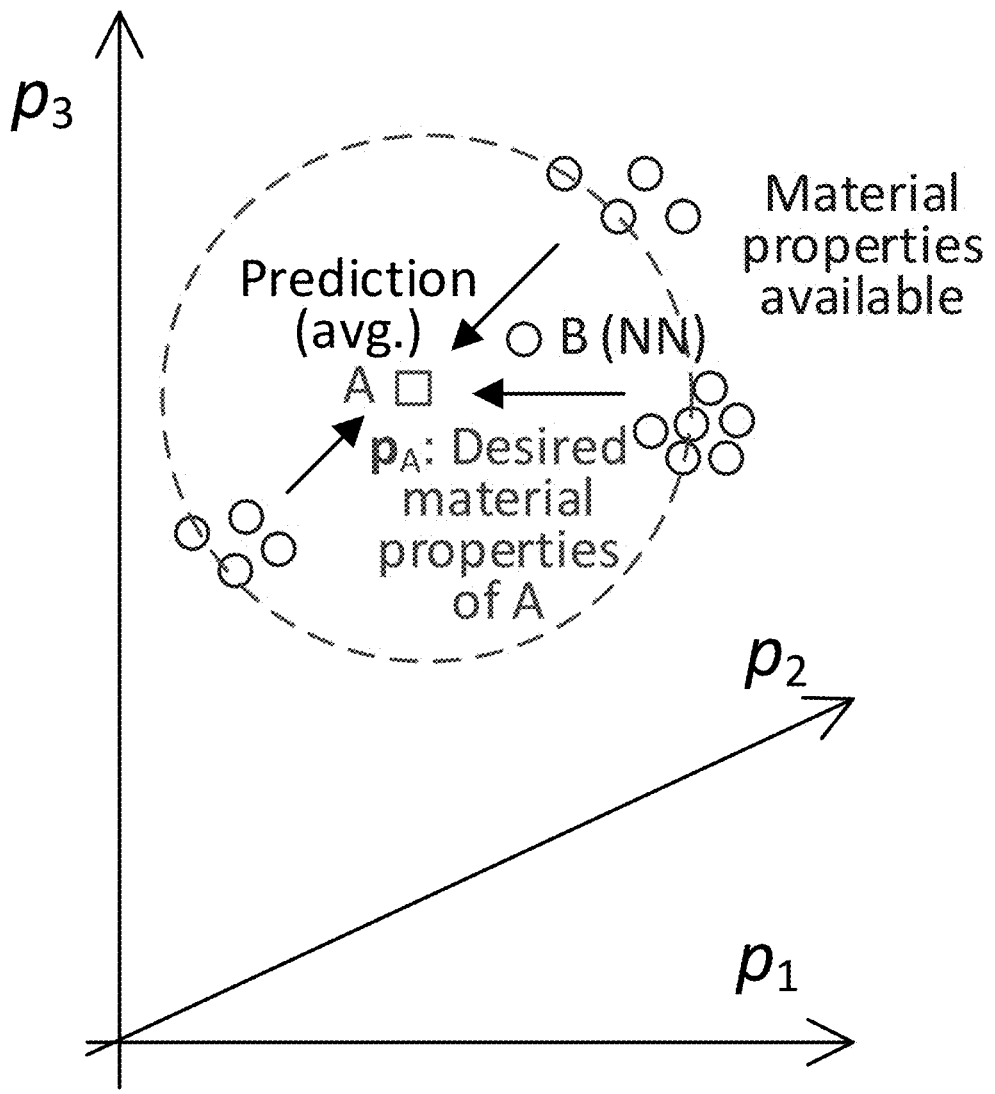
FIG. 14 presents the essentials of averaging in the space comprising the input parameters.

FIG. 14 explains, at a high level, how we are going to populate the input parameter space and carry out the prediction. In case of continuous-valued parameter space, one can apply k nearest neighbor (k-NN) averaging for determining the parameters corresponding to point A in FIG. 14, $p_A$:

$$p_A = \frac{1}{k} \sum_{i=1}^{k-NN} p_i \quad (3)$$

Here, $p_i$ represents the parameter vector corresponding to the i-th nearest neighbor of point A in FIG. 14.

4.3. Feed-Forward Neural Network

For further information on the neural networks, refer to (SteingrimssonJonesKisialiou 2018).

4.4 Alternative Methods Considered, but not Chosen
 1. Multi-Class ML or Multi-Class Neural Networks: More appropriate for classification problems.
 2. Evolutionary Methods: May exhibit problems with "curse of dimensionality" in high dimensional search spaces.
 3. Combinatorial search methods: Do not provide insight desired into the physics and numerical aspects.
5. Example: "Forward" Prediction of Fatigue Endurance Limit As a simple example, one can look to "forward" predict the fatigue endurance limit as follows:

$$\text{endurance limit} = f(\text{UTS}, \text{process}, \text{defect(process)}, \text{grain(process)}, \text{microstructure(process)}, T \ldots) \quad (4)$$

wherein the composition is specified in terms of the % strength of constituent elements, and UTS represents the ultimate tensile strength. In general, we may be looking at a complex, combinatorial optimization problem.

6. General Approach to Inferring the Feature Set (e.g., Composition): "Backward" Prediction "Backward prediction" (identification of candidate compositions) is accomplished through an inverse design framework, one that suggests candidate compositions to test next, based on a set of property specifications and design goals. Through a sequential learning workflow, the inverse design tool is used to suggest test candidates, and the data from those tests are then used to retrain the model, presumably leading to iterative refinements and convergence. For efficiency, we allow for polynomial fit, during the iterative refinements, when the underlying physics are not expected to result in major nonlinearity.

7. Specifics on the Approach to the "Backward" Prediction
   To develop the "backward" prediction, we will be considering a few approaches.
1. Starting Point: Microstructure of the Nearest Neighbor
   The simplest approach consists of identifying the neighbor, B, to the desired HEA, A, in FIG. 14, and simply using the microstructure of B as a starting point. Other options exist as well.
2. Baseline Approach: Generalization of (LiuKumarChen 2015)

Figure 16:
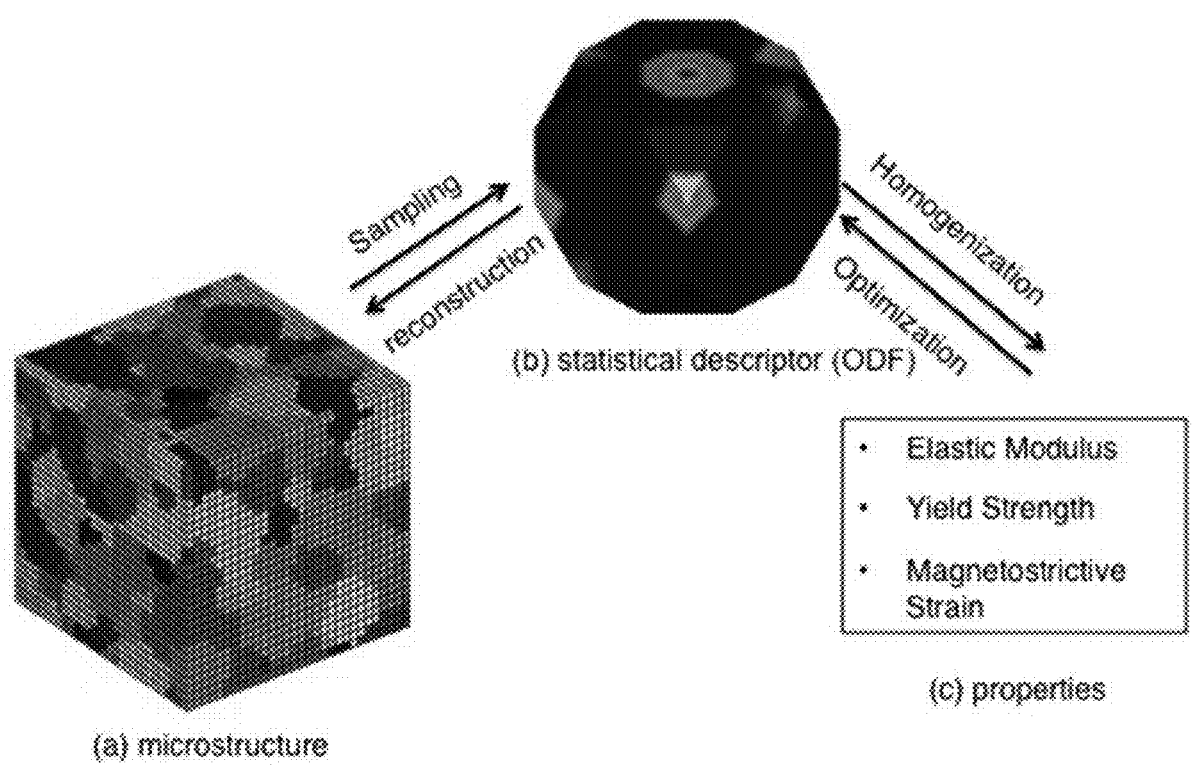
FIG. 16 outlines a baseline approach for inferring the microstructure from desired material properties.
Figure 17:
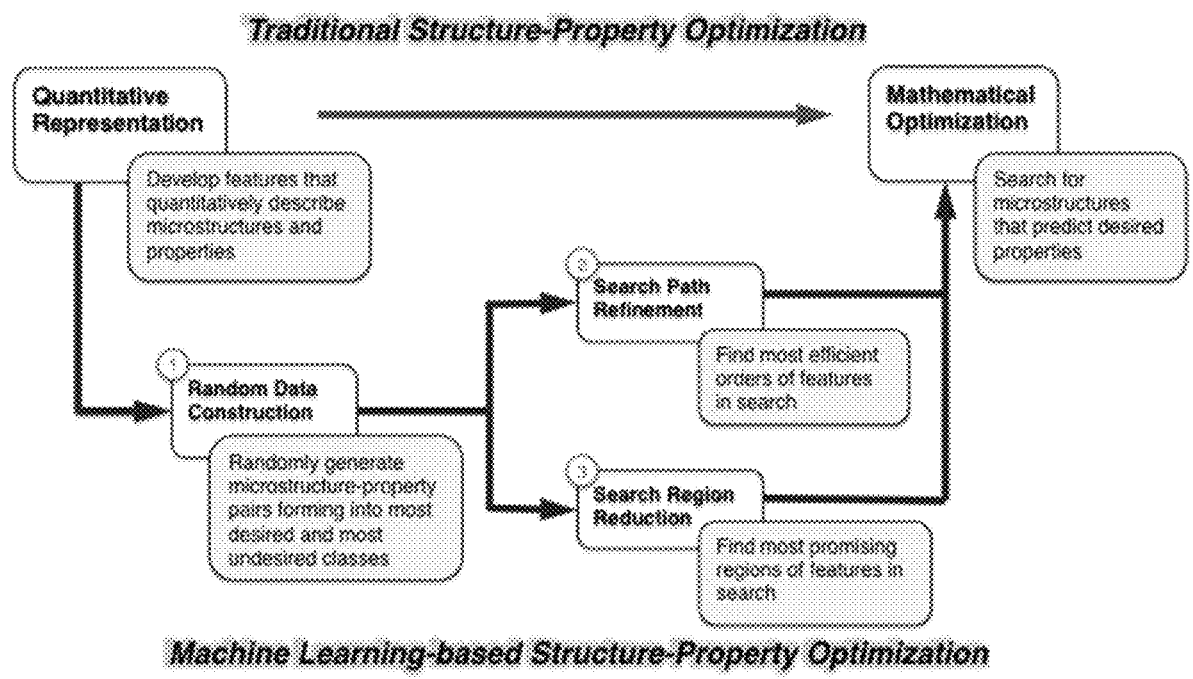
FIG. 17 summarizes material structure optimization through microstructure-property pairs.

Our baseline approach for inferring the microstructures from the properties desired, shown in FIG. 16 and FIG. 17, is based on (LiuKumarChen 2015). The microstructure design of polycrystals can be performed by tailoring the distribution of various crystal orientations [the oriental distribution function] in the microstructure (LiuKumarChen 2015). Structural optimization is carried out along different crystallographic directions to attain favorable properties. The multiple crystallographic directions embedded in the multi-dimensional ODF are used as control variables and the theoretical functions for properties are the objectives (Liu-KumarChen 2015). ML allows us to explore multiple design solutions and diminish search time in the high dimensional space of microstructure design problems, where the number of distinct design candidates can be infinite.

Two crucial ML steps, namely, search path refinement and search space reduction, are designed to develop heuristics that tour the search force to a much smaller preferable space (LiuKumarChen 2015). A ML-based preprocessing is designed to locate critical region of a search space with a small overhead, so that the search force can be consciously concentrated.

8. Towards Simplification—Suitability of ML vs. Polynomial Fit in Absence of Discrete Jumps in Data One can study if the alloy candidates of interest exhibit discrete jumps in the material properties observed. With increasing x, the AlxCoCrFeNi alloys change from the single face-centered-cubic (FCC) phase to single body-centered-cubic (BCC) phase with a transition duplex FCC/BCC region. If the data does involve continuous change (continuous $1^{st}$ and $2^{nd}$ derivatives), and there are not discrete jumps, similar to the on-set of superconductivity (where the conductivity suddenly exhibits a discrete jump to infinity), one can employ polynomial fit (of much lower complexity), in conjunction with ML, or at least as a part of a hybrid solution.

9. More on a Custom, Hybrid Solution for "Backward" Prediction: Polynomial Fit Employed for Complexity Reduction One can employ ML to predict if you are close to a close to a state transition. If not, then polynomial fit may suffice. If you are indeed close to a state transition, then a ML approach may be necessitated.

Similar to (LiuKumarChen 2015) and (LingAntonoBajaj 2018), one can employ ensample prediction, i.e., build many models (often hundreds) in order to predict a given quantity of interest. Each model will make a prediction for a given new test point, and the final ensemble prediction will be given by the average value of all the individual model predictions. A polynomial function with numerical representation can be inverted. If the polynomial is monotonically increasing or decreasing, the inverse is unique. Otherwise, more than one inverse may exist, and the designer is at liberty of picking the best one.

10. Prediction of Distributions (Mean and Variance)—Stochastic Prediction

It is important to keep in mind that we are looking to develop a stochastic, not deterministic, predictors. The outputs of the predictors will involve mean and variance, not a single scalar quantity. Our intent is to determine what % of data falls within a single std. dev (·), what within 26's, etc.

7.2 Specific Approach to Prediction Incorporating Physics-Based Modeling—Capturing of Physical Dependencies 1. Generic Approach to Incorporating a Physics-Based Model We start with developing qualitative understanding of the physics and dependencies underlying the data available. We then present a generic mathematical model describing the data. In case of limited data, we start with a simple, linear model, but if supported by sufficient data for training, we employ a more sophisticated model. Next, we introduce non-linearity into the model, based on the underlying physics. The kernel functions of the non-linear models may utilize tanh(·), log(·), or exp(·) functions, based on applications. In the case of reliability analysis, we may choose exponential functions. By carefully formulating the structure of the models, such as to capture underlying dependencies, together with a priori knowledge derived from the physics at play, one can expect to infer more from the—usually limited—data available than when directly using the same data to train generic, out-of-the-box models (with no apriori knowledge incorporated).

2. Overview Over the Primary Physics-Based Models Incorporated

One of the primary, unique aspects of the innovation involves incorporation of physics-based, metallurgical prediction models. There can be great benefits derived from combining ML with physics-based modeling approaches for design of alloys or composites (in particular HEAs), for improved prediction accuracy. These modeling approaches may include 1. Thermo-dynamics (CalPHAD) (MiracleSenkov 2017), (FengGaoZhangGuo 2018), (ZhangZhangDiaoGao 2016), (ShiCollinsFengZhang 2018).

2. First principle calculations of bond energies and phase stability (FengGaoZhangGuo 2018), (GludovatzHohenwaterCatoor 2014), (TroparevskyMorrisKent 2015), (FengGaoLeeMathes 2016).

3. Empirical rules (TroparevskyMorrisKent 2015), (ZhangZhouLinChen 2008), (FengGaoLeeMathes 2016), (GaoNgLuLiu 2011).

4. Mesoscale models to predict distribution of phases in the microstructure and their morphologies, as influenced by thermal history and alloy chemistry (RadhakrishnanGorti 2019), (RadhakrishnanGorti 2016).

5. Models for dislocation dynamics and slip band information to help with accurate prediction of stress/life curves.

6. Feature representations useful for characterizing, and distinguishing between, chemical reactions associated with specific corrosion attacks, such as CMAS or calcium sulfate attacks.

Table 8 lists leads towards incorporating physics-based intuition into machine learning algorithms for predicting the material properties of alloys. In reference to Table 8, mechanical nano-twins at low temperature can result in continuous steady strain hardening, which improves both fracture toughness and strength, according to B. Gludovatz et. al. (GludovatzHohenwaterCatoor 2014). By incorporating physics-based models, one can help the ML algorithms to avoid fitting to the input data. The physics-based models can also help with extrapolation into uncharted territories (into subspaces of the parameter space for which there are few or no experimentally obtained data points). The physics-based models can help with developing understanding into complex combinations of material and process-induced imperfections.

2.1 Thermodynamics: Interaction of ML with Phase Stability Models from CALPHAD

Figure 28:
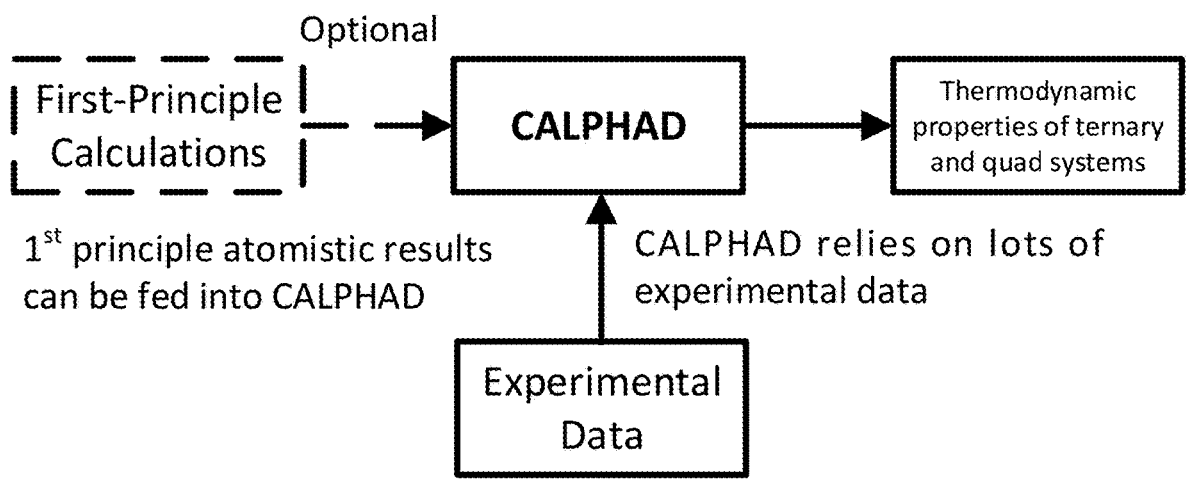
FIG. 28 provides high-level presentation of CALPHAD, in terms of the primary inputs, the primary outputs and association with first-principle calculations.
Figure 29:
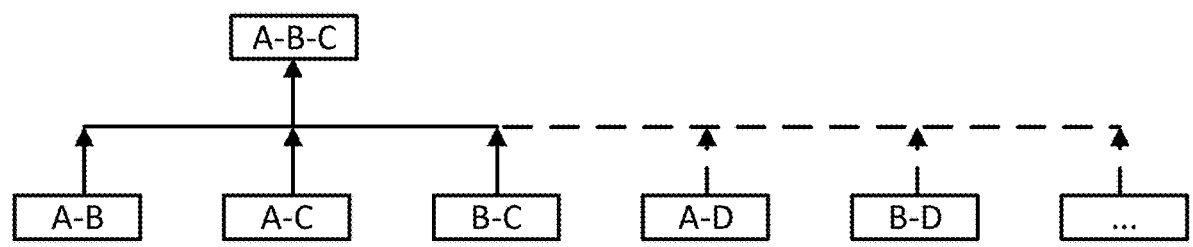
FIG. 29 illustrates how properties of a ternary system (A-B-C) are associated, at a high level, with the properties of the constituent binary systems (A-B, A-C and B-C).
Figure 30:
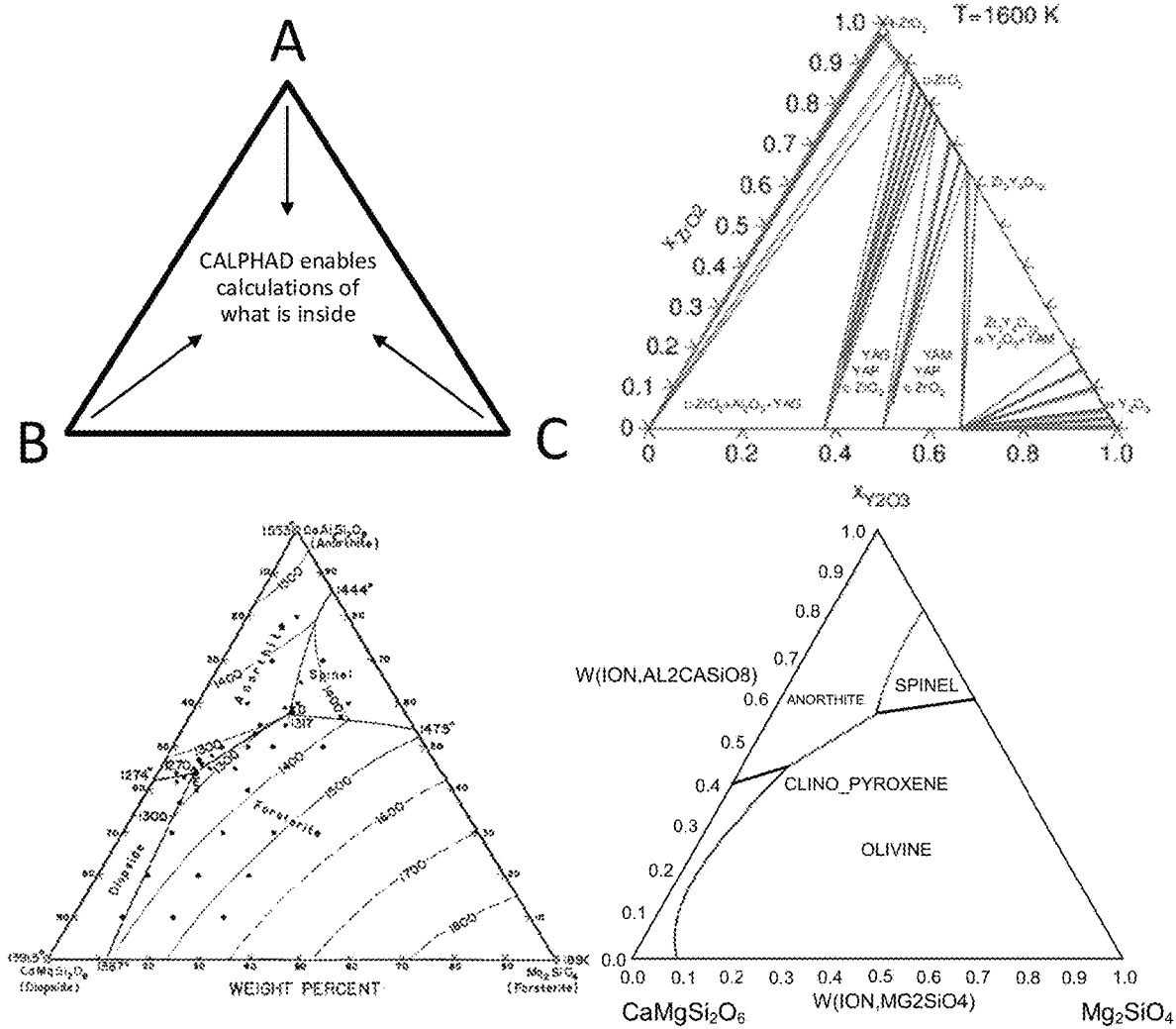
FIG. 30 presents an illustration of analysis of properties of ternary material systems in CALPHAD.
Figure 31:
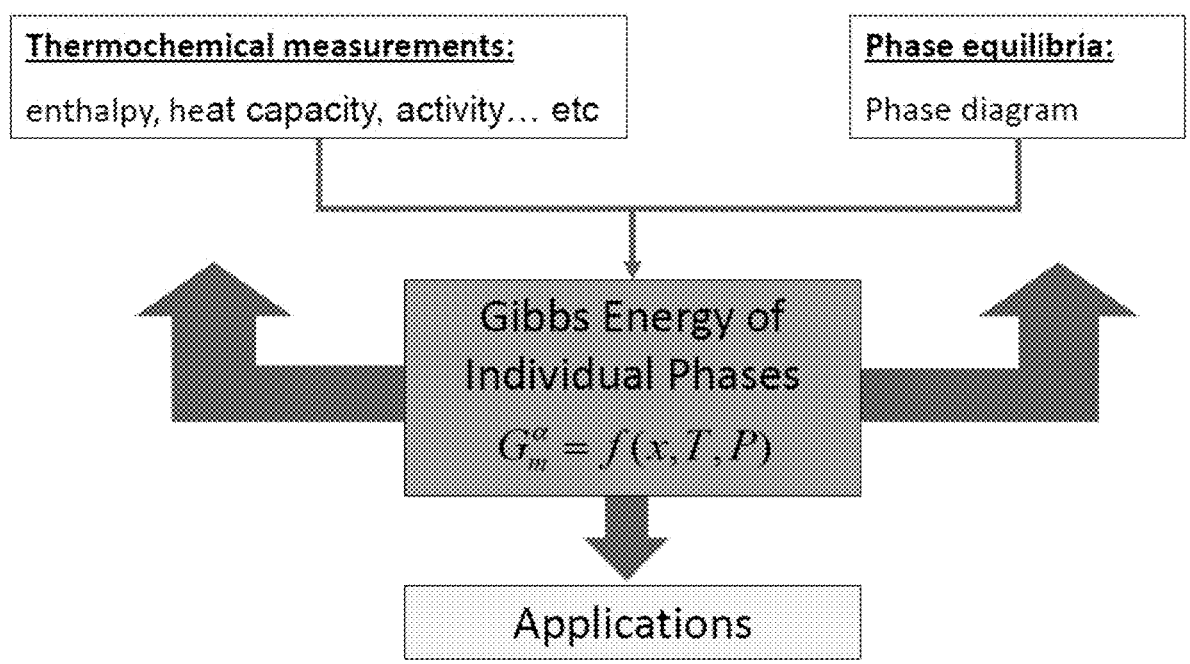
FIG. 31 illustrates, at a high level, how CALPHAD computes the Gibbs free energy of individual phases from thermochemical measurements and phase equilibria information (from (Thermo-Calc 2014)).
Figure 32:
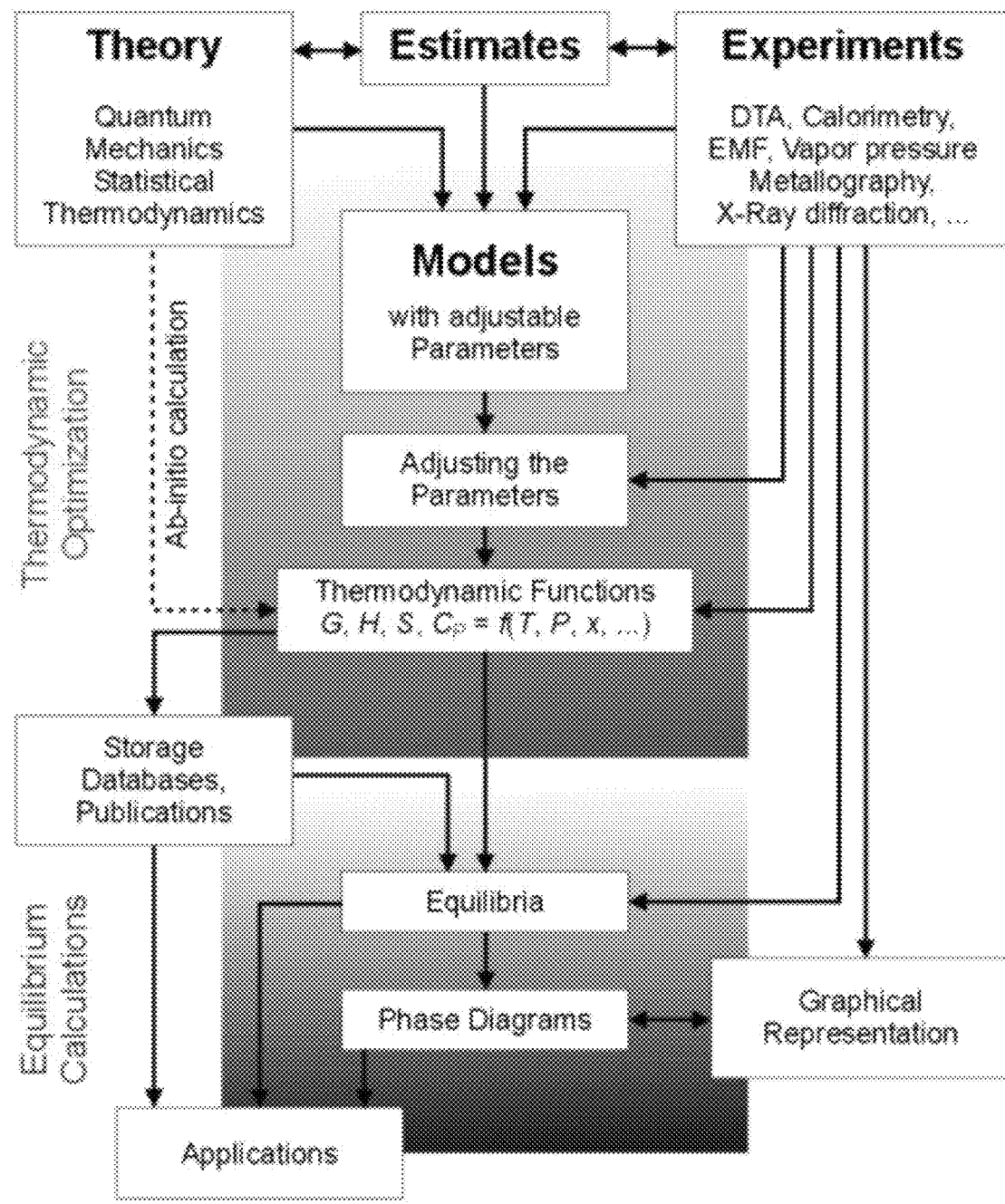
FIG. 32 provides more specific information of the internal structure of CALPHAD (again from (Thermo-Calc 2014)).

The CALPHAD methodology employs a phenomenological approach to calculate multi-component phase diagrams, based on binary phase information, as shown in FIG. 28, FIG. 29 and FIG. 30. Per FIG. 31 and FIG. 32. CALPHAD enables material designers to estimate the thermodynamic properties of ternary systems (A-B-C combinations), based on (a) thermodynamic

TABLE 8

Further specifics on application of machine learning to prediction of material properties.

| ID | Quantity Predicted | Sources of the Input Data | Leads towards Incorporating Physics-Based Intuition |
|---|---|---|---|
| 1 | Material Hardness | (MiracleSenkov 2017), (LyuLeeWangFan 2018) and (ZhangZuoTangGao 2014), (TsaiYeh 2014), (Jien-Wei 2006), (YehChenLinChen 2007) | X. Q. Chen et. al. can model hardness of polycrystalline materials (ChenNiuLiLi 2011) |
| 2 | Yield Strength | (Miracle Senkov 2017), (SenkovMiracleChaput 2018), (LyuLeeWangFan 2018), (ZhangZuoTangGao 2014), (ZhangYangLiaw 2012), (DiaoFengDahmen 2017), (TsaiYeh 2014), (GludovatzHohenwater Catoor 2014), and (YehChenLinGan 2014) | W. A. Curtin et. al. can predict yield strength, only based on edge or screw dislocation. Can predict yield strength of high-entropy alloys (LeysonHector Curtin 2012), (RaoVarvenne Woodward 2017), (VarvenneLuque Curtin 2016), (LeysonCurtinHector Woodward 2010), (NöhringCurtin 2018), (VarvenneLeyson 2017). W. Jiang et. al. have theory to predict strength and explain why strength higher than conventional metal (JiangZhaoQianSrolovitz 2019). |
| 3 | Material Plasticity/Ductility | (ZhangZuoTangGao 2014), (MiracleSenkov 2017), (DiaoFengDahmen 2017), (TsaiYeh 2014), (GludovatzHohenwater Catoor 2014), (LiPradeepDeng Raabe 2016). | (SarmaDawson 1996), (VanHoutte Delannay 2002), (Signorelli BertinettiTurner 2009), (Toth MolinariEstrin 2002), (Boudifa SaanouniChaboche 2009) |
| 4 | Material Fatigue | (HemphillYuanWang 2012), (Tang YuanTsaiYeh 2015), (Thurston GludovatzHohenwater 2017), (Chen WangSeifiLewandowski 2018), (ShuklaWangCottonMishra 2018), (LiuNeneFrankSinha 2018), (NeneFrankLiuSinhaMishra 2018), (SeifiLiYongLiawLewandrowski 2015), (GaoYehLiawZhang 2016) | Predicting the S/N curve may be difficult; (HemphillYuanWang 2012), (SangidMaierSehitoglu 2011) |
| 5 | Fracture Toughness | (MiracleSenkov 2017), (Thurston GludovatzHohenwater 2017), J. J. Lewandowski (SeifiLiYongLiaw Lewandrowski 2015), and (LiLiawGao 2018), (LiZhang 2016), (ZhangZuoTangGao 2014), (GludovatzHohenwaterCatoor 2014) | (SinghShetty 1989), (ShenderovaBrennerOmeltchenko 2000) |
| 6 | Material Creep | (LiWangWuLiaw 2018), (ChenLiXieBrechtl 2018), (PraveenKim 2018) | (a) Dislocation theory to predict regular (smooth) creep behavior (PraveenKim 2018) (b) See how stress changes; based on nano-identation (MuthupandiKimNaPark 2017). (WongHellingClark 1988), (LiDasgupta 1993) | database and (b) Gibbs free energy. CALPHAD can also help material designers analyze the phase stability of quad systems (A-B-C-D combinations), based on properties of the binary and ternary systems (Thermo-Calc 2014).

Applications, based on the CALPHAD methodology, such as Thermo-Calc, can tell material designers how stable, or how meta-stable, each phase in the ternary or quad system is. CALPHAD can provide estimates for stability for specific phases in a multi-component systems consisting of up to 20 compositions (TernaryPlot2020).

CALPHAD relies on lots of experimental data, much of which was collected in the fifties or sixties. There are gaps in the CALPHAD database, such as in regards to B2 phase in multi-component systems. The B2 phase that does not appear in binary or ternary systems. As a work-around, the B2 phase may be modeled into binary or ternary systems, even though it is not stable there (only meta-stable).

The methodology of accelerated design and qualification of new alloys can be extended such as to efficiently exploit the configurational entropy in high-entropy alloy systems. The solution thermodynamics of solvent-rich systems is well described by binary interactions. But the HEA systems involve significant contributions from ternary interactions that also need to be quantified for accurate prediction of phase stability. Extension of CALPHAD databases for this purpose can be facilitated by DFT calculations of mixing enthalpies in equi-atomic ternary systems.

The determination of the most appropriate heat-treatment process may also rely on thermodynamics calculations (formation of a $2^{nd}$ phase).

2.2 First-Principle Effects (DFT)

Investigations of alloys from first-principle perspective involves computational modeling at atomic scale, for example of bond energies or phase stability. First-principle studies leverage quantum mechanics calculations, with DFT approximating the Schrodinger equation, to simulate the electronic properties and stability of material candidate from which the most promising leads are confirmed experimentally. Even so, DFT calculations tend to be computationally expensive, often taking hours to days for a single molecular structure, and more accurate results are often associated with lengthier calculations performed at higher-levels of theory. On the other hand, properly trained neural networks can (in theory) yield highly accurate predictions with relatively low computational cost. First-principle (DFT) calculations can be used to validate (sanity check) the prediction outcomes of traditional ML systems, i.e., as a part of a hybrid computational system.

As suggested by FIG. 28, applications, based on the CALPHAD methodology, such as Thermo-Calc, do not carry out first-principle (DFT) calculations explicitly. However, applications based on CALPHAD can accept first-principle data from applications such as VASP. VASP is a computer program for atomic scale materials modelling, e.g. electronic structure calculations and quantum-mechanical molecular dynamics, from first principles. VASP computes an approximate solution to the many-body Schrödinger equation, either within DFT, by solving a Kohn-Sham equations, or within a Hartree-Fock (HF) approximation, by solving Roothaan equations. Hybrid functionals that mix the Hartree-Fock approach with density functional theory are implemented in VASP as well. Furthermore, Green's functions methods and many-body perturbation theory (2nd-order Møller-Plesset) are available in VASP as well (VASP 2020).

2.3 Empirical Rules

The empirical rules (ZhangZhouLinChen 2008) predict the formation of solid solution phases, based on Delta, which describes the comprehensive effect of the atomic-size difference in multi-component alloy systems, and the mixing enthalpy of a solid solution, $\Delta H_{mix}$. The empirical rules specify which combinations of ($\Delta H_{mix}$, Delta) result in formation of a S zone (a zone where only solid solution will form), which combinations result in formation of a S' zone (a zone where the a solid solution as a main phase), which combinations result in a $B_1$ zone, which in a $B_2$ zone and which in a C zone. The $B_2$ zone contains Mg and Cu based bulk metallic glasses, while the $B_1$ zone contains other kinds of bulk metallic glasses, such as Zr. In the C zone, many intermediate phases are expected to form.

In Table 16, we apply the empirical rules to verify the sanity (phase stability) of compositions predicted to yield high tensile strength, on basis of machine learning or regression analysis. Similar to the first-principle (DFT) and thermodynamics (CALPHAD) calculations, the empirical rules can be incorporated into a hybrid computational paradigm, and used to validate (sanity check) the prediction outcomes of traditional ML.

2.4 Mesoscale Models

The mesoscale models can be used to predict distribution of phases in the microstructure and their morphologies, as influenced by thermal history and alloy chemistry (RadhakrishnanGorti 2019), (RadhakrishnanGorti 2016). Similar to the first-principle calculations, and the empirical rules, this phase information can be used to complement (validate) the prediction outcomes of traditional ML, i.e., as a part of a hybrid computational system.

2.5 Models Involving Dislocation Dynamics or Slip Band Information

Models Involving Dislocation Dynamics or Slip Band Information may be incorporated into prediction models for fatigue life. The stress/life (S/N) curves tend to be related to crack initiation, which can associated with dislocation dynamics and slip band information.

2.6 Environmental Resistance (Oxidation, Corrosion or Radiation)

Depending on the chemical reactions involved, and the temperatures at which they occur, one can derive a list of features that properly describe the data, e.g., using canonical component analysis. This can help in terms of developing distinguishing characteristics between CMAS and calcium sulfate ($CaSO_4$) hot corrosion, with and without the influence of sea salt, and with developing coatings resistant to CMAS and calcium sulfate hot corrosion.

3. General Approach to Construction of a Physics-Based Model: Application to Prediction of Ultimate Tensile Strength

3.1 Approach

Figure 18:
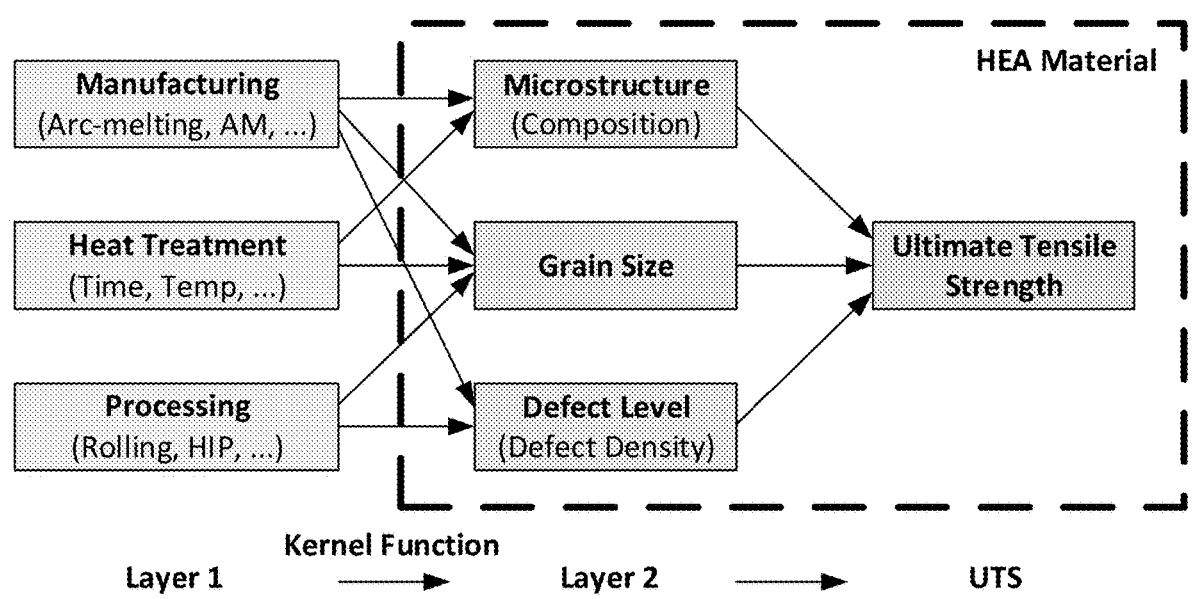
FIG. 18 presents underlying physical dependencies structured in a fashion resembling a neural network. Our intent is to construct models capturing the underlying physics. The model shows that microstructure formed depends on the heat treatment process applied.

First, we start out by capturing the physics-based dependencies, per FIG. 18. Assuming a linear model works, each arrow in FIG. 18 represents a coefficient in a matrix. In this case, the parameters at the $1^{st}$ level consist of manufacturing, heat treatment, and processing. The parameters at the $2^{nd}$ level consist of microstructure, grain size, and defect levels. As depicted in FIG. 18 the dependence relationships still represent a linear model.

Second, the approach assumes constructing an initial, linear regression model with input parameters from a continuous range. The first level of the model can be represented as follows:

$$z=[\text{micro-structure,grain size,defect level}] \quad (5)$$

$$x=[\text{manufacturing,heat treatment,processing}] \quad (6)$$

$$z=Ax+c. \quad (7)$$

Now, the second level in FIG. 18 can be written as shown below:

$$\text{UTS}=y=b^T z+d. \quad (8)$$

This equation could give rise to an overall linear model of the following type:

$$\text{UTS}=y=b^T(Ax+c)+d=b^T Ax+(b^T c+d)=\tilde{a}^T x+e. \quad (9)$$

Note if, say, microstructure is a function of other input parameters, then these other input parameters should not be present at the current level, but should be accounted for at a preceding level.

Third, alternatively, one can construct a initial, linear model as follows:

$$\text{UTS}=y=\tilde{a}^T x_B+e, \quad (10)$$

where, in the case of prediction of the UTS, $x_B$ can be defined as $$x_B=[\% \text{ Al},\% \text{ Mo},\% \text{ Nb},\% \text{ Ti},\% \text{ V},\% \text{ Ta},\% \text{ Zr},\% \text{ Hf},\% \text{ Cr}]. \quad (11)$$

Fourth, the set of input parameters (x) can be extended, by adding other continuous-valued input parameters, such as temperature. At this point, we have accounted both for the compositions, the temperature, and the continuous-valued input parameters. This arrangement involves a relatively-straight forward extension.

Fifth, one can further extend the set of input parameters (x), by adding categorical inputs, such as for the manufacturing process used. At this point, the problem becomes a mixed-integer optimization problem. Our approach assumes gradual introduction of complexity into the model.

Sixth, one can introduce nonlinearities (non-linear kernel functions), based on the underlying physics. In case of FIG. 18 [Eq. (9)], this formula can be represented as $$\text{UTS}=y=\tilde{a}^T f([\text{micro-structure,grain size,defect level}])+e=\tilde{a}^T f(x)+e. \quad (12)$$

Here, $f(\cdot)$ may represent the sigmoid function, a $\log(\cdot)$ function, or an $\exp(\cdot)$. This invention assumes that $f(\cdot)$ is selected such as to suit the application at hand.

Seventh, in case of the prediction presented in FIG. 24 and FIG. 25, the pre-direction model can be represented as $$\text{UTS}=y=g(x_B). \quad (13)$$

Figure 19:
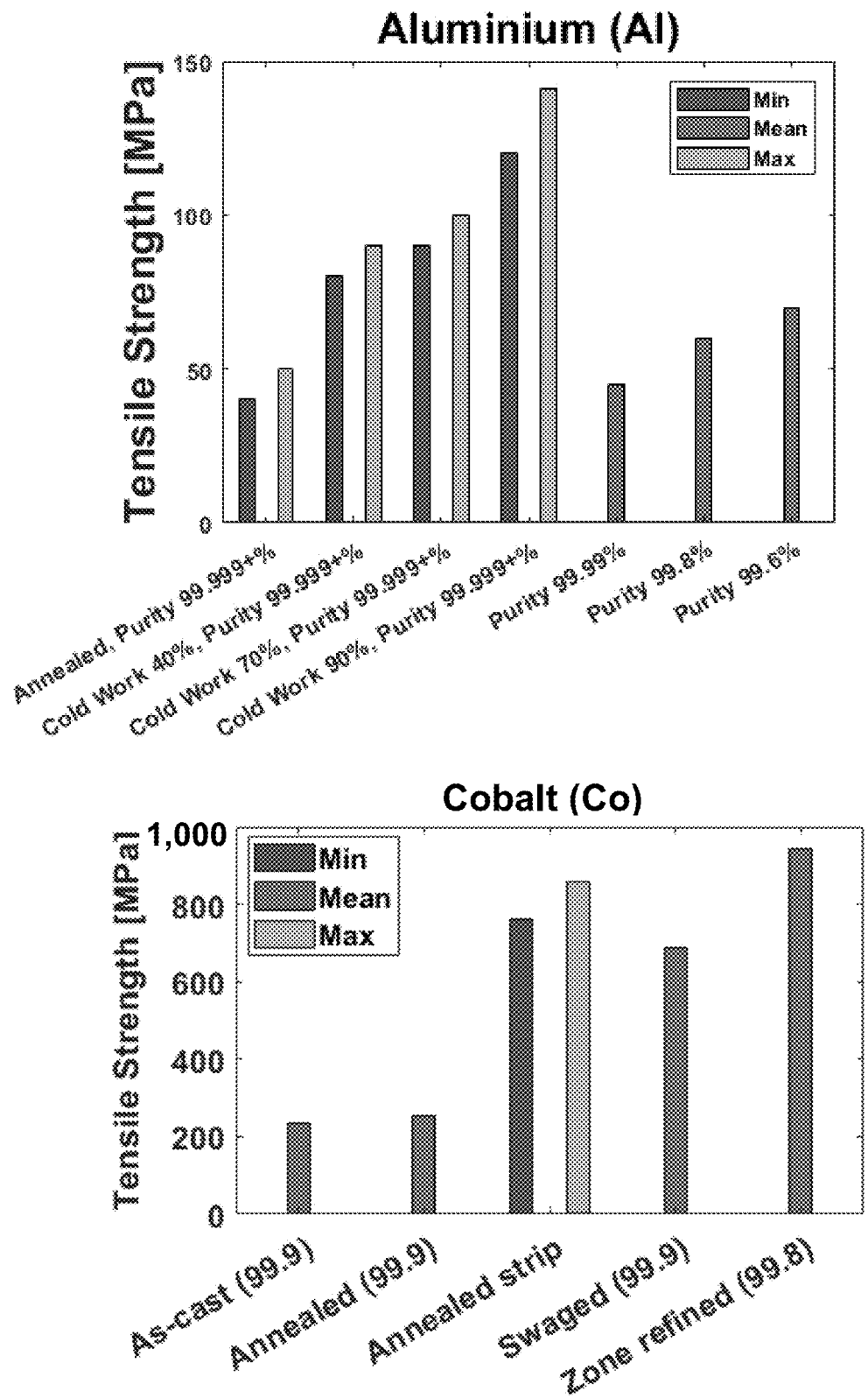
FIG. 19 presents variations in tensile strength of Aluminum and Cobalt, based on purity and processing conditions (AsmHandbook 1990).
Figure 20:
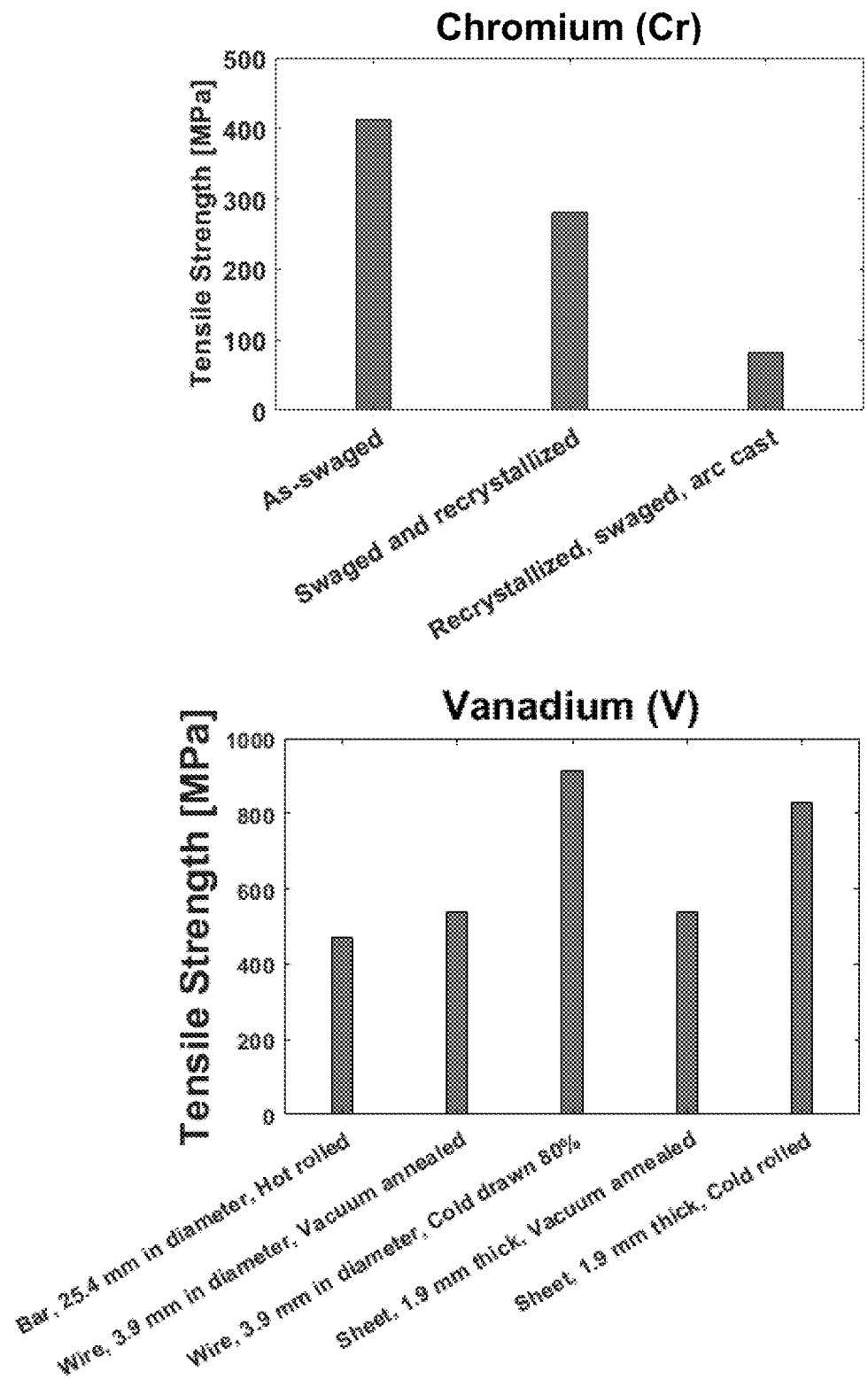
FIG. 20 presents variations in tensile strength of Chromium and Vanadium, based on processing conditions (AsmHandbook 1990).

Some of the underlying physics may be common for regular alloys and HEAs. Hence, one may develop certain aspects of the model, through the analysis of data available for regular alloys. FIG. 19 and FIG. 20 are presented with this in mind.

Eighth, one can systematically expanding the model, such as to introduce additional complexity.

Ninth, one can systematically retrain the model, as additional complexity is introduced. If the addition of a non-linearity or an input parameter (complexity) does not improve the prediction accuracy of the model, one can analyze why the observed prediction accuracy has not conformed with expectations?

3.2 Further Theoretical Considerations (Justifications)

Broadly speaking, for the selection of kernel functions based on underlying physics, one should first look at the general shape of the data. Sometimes, the selection may be based on qualitative physics-based insights of an expert. The expert may know what to expect, or if there is too much or too little of a given concentration.

A parametrized description related to the microstructure may be based on the following parameters: Radius asymmetry, difference in atomic radii, number of valence electrons, enthalpy of mixing, ideal entropy of mixing, mean melting temperature, difference in Pauling electro-negativity, electro negativity difference, cohesive energy, first ionization energy, covalence radius, electron affinity, molar volume, etc.

The parametrized description of the defect levels may involve a significant undertaking, as noted above, since there are so many different types to consider. A systematic approach to the parametrized description of defect levels may start with a single case (e.g., powder-bed AM) and a single category of defects (macro-scale, micro-scale or nano-scale defects).

A parametrized description of the grain size may similarly involve a significant undertaking. A systematic approach may exclude metallic glasses (amorphous metals), but instead focus on characterizing the distribution in the size and shape of polycrystalline grains.

The simplest description of the heat treatment process may involve a simple listing by categories. However, such categorical designation may be subject a level of arbitrariness with regards to how the data scatters along the axis listing the categories. In case of hot isostatic pressing, one soon would need to account for the temperature, pressure and duration of the HIP. Similarly, in case of annealing, one would need to account for the temperature and duration of homogenization.

4. Necessary Step Towards a Physics-Based Model: Characterization of Expected Sources of Variations—Application to Prediction of Ultimate Tensile Strength In order to yield highly accurate predictions, one needs to understand the sources causing variations in the property predicted, and properly account for these sources.

4.1 Expected Dependence of Tensile Strength on Alloy Type

As an example, we expect the mechanical properties of refractory HEAs to differ from those of traditional alloys. For refractory HEAs and transition metals, we expect higher yield strength and lower ductility, compared to other alloys. By increasing the concentration of aluminum (Al) in transition metal type materials, one has a reason to believe the strength will improve (JosephStanford 2017).

4.2 Expected Dependence of Tensile Strength on Temperature

Usually, when the temperature increases, the ultimate tensile strength tends to decrease. However, we are unaware of a theoretical model describing this relationship. But with that said, FIG. 21 captures empirical results supporting this observation.

4.3 Expected Dependence of Tensile Strength on Manufacturing Technique

Dependence of the tensile strength on the manufacturing technique employed may depend on specifics of the implementation. Traditionally, arc-melting and spark plasma sintering have been the two main processing techniques employed to fabricate bulk HEAs (GorsseHutchinson 2017). To successfully produce homogeneous bulk HEAs by arc-melting, extensive re-melting and intermittent ingot inversions are required, and powder alloying and refinement (typically via balling milling) is necessary when processing via the SPS route (GorsseHutchinson 2017). The main undesirable feature of the metal additive manufacturing process are the non-equilibrium thermal cycles, consisting of the solid-melting crystallization and solid-remelting recrystallization under fast heating and cooling conditions, which generate anisotropic microstructures and defects.

4.4 Expected Impact of Grain Size on Yield or Tensile Strength

Grain-boundary strengthening (or Hall-Petch strengthening) is a method of strengthening materials by changing their average grain size (GrainBoundaryStrengthening 2019). It is based on the observation that grain boundaries are insurmountable borders for dislocations and that the number of dislocations within a grain have an effect on how stress builds up in the adjacent grain, which will eventually activate dislocation sources and thus enable deformation in the neighboring grain (GrainBoundaryStrengthening 2019). So by changing grain size, one can influence the number of dislocations piled up at the grain boundary, which impacts the yield and tensile strengths (GrainBoundaryStrengthening 2019). The Hall-Petch relation models the relationship between the yield stress and the grain size as $$\sigma_y = \sigma_0 + \frac{k_y}{\sqrt{d}} \tag{14}$$

Here, $\sigma_y$ is the yield stress, $\sigma_0$ is a materials constant for the starting stress for dislocation movement (or the resistance of the lattice to dislocation motion), $k_y$ is the strengthening coefficient (a constant specific to each material), and d is the average grain diameter (GrainBoundaryStrengthening 2019).

4.5 Expected Dependence of Endurance Limit on UTS, for Fixed Defect Level and Heat Treatment Process Upon studying stress states, fracture surfaces, and tensile stress at the fracture-initiation site, one can expect the fatigue-endurance limit to scale in proportion with the UTS, for a fixed defect level and heat-treatment process. Ref. (MenzelDauskardt 2006) cites a study of the stress-life fatigue behavior of a $Zr_{41.25}Ti_{13.75}Ni_{10}Cu_{12.5}Be_{22.5}$ bulk metallic glass using notched cylindrical bars, where the fatigue endurance limit of ~½ of the UTS was reported. This result was significantly higher than the value of ~1/10 of the fatigue endurance limit previously reported using four-point bend specimens (MenzelDauskardt 2006).

4.6 Expected Dependence of Endurance Limit on Defect Levels, for Fixed UTS and Heat Treatment Process Defect levels are here taken to broadly represent microstructural effects. While one expects the increased defect level to exert adversarial impact on the endurance limit, complete characterization of microstructural aspects may involve a significant undertaking. Ref. (LiuGwalaniKomarasamy 2019) reports on the intrinsic role of microstructure on persistent slip bands. Ref (LiuGwalaniKomarasamy 2019) notes that although the nano-sized $L1_2$ precipitates enhance tensile strength, no improvement in fatigue properties have been observed.

5. Necessary Step Towards a Physics-Based Model: Characterization of Sources of Observed Variations—Application to Prediction of Ultimate Tensile Strength Table 9 shows that one can expect~2× variations in the endurance limit, based on defect levels (defect size, density, and type) and raw material purity, for a fixed UTS. This trend suggests that the explicit access to the information on the defect level may be needed in order to accurately predict the endurance limit. The samples in Table 9 were homogenized at 1,000° C. for 6 hour, water quenched, and then cold rolled. For Condition 1, shrinkage pores and macro-segregation remained in some portions. For Conditions 2 and 3, shrinkage pores and macro-segregation were removed before cold rolling.

Table 10 similarly illustrates that one can expect~2× variations in the endurance limit, likely caused by variations in the grain size, even for the same microstructure (FCC) and similar process (hot-rolled and heat-treated). Together, Table 9 and Table 10 illustrate that the accurate prediction of the endurance limit is not possible, based on the UTS alone. One also needs to know the defect levels (the defect size, density, and type), the gain size, and even parameters of the heat-treatment process. These observations are consistent with those of (HemphillYuanWang 2012) as well as with those of (TangYuanTsai 2015).

TABLE 9

For a given composition ($Al_{0.5}CoCrCuFeNi$), microstructure, grain size, and process, the endurance limit exhibits a high degree of correlation with the defects reported (HemphillYuanWang 2012), (TangYuanTsai 2015).

| Composition | Microstructure | Grain Size [um] | Process | Defects Reported | Tensile Strength (MPa) | Endurance Limit (MPa) |
|---|---|---|---|---|---|---|
| Al0.5CoCrCuFeNi Condition-1 | 2 FCC | 2 or 1 mm (matrix phase or Cu-rich) | annealed + cold-rolled | Few defects- | 1,344 | 472 |
| Al0.5CoCrCuFeNi Condition-2 | 2 FCC | 2 and 1 mm (matrix phase and Cu-rich) | annealed + cold-rolled | commercial-purity raw elements | 1,344 | 382 |
| Al0.5CoCrCuFeNi Condition-3 | 2 FCC | 2 and 1 mm (matrix phase and Cu-rich) | annealed + cold-rolled | high-purity raw elements | 1,344 | 360 |
| Al0.5CoCrCuFeNi Condition-1 | 2 FCC | 2 and 1 mm (matrix phase and Cu-rich) | annealed + cold-rolled | High defect level | 1,344 | 270 |

TABLE 10

Variations in endurance limits for CoCrFeNiMn (the Cantor alloy) (KimHamKimLee 2019), (KashaevVentzke 2019), (ChlupFintovaHadraba 2019), (SuzukiKoyamaHamada 2019).

| Composition | Microstructure | Grain Size [um] | Manufacturing Technique | Process | Defects Reported | Load Ratio (R) | Tensile Strength (MPa) | Endurance Limit (MPa) |
|---|---|---|---|---|---|---|---|---|
| CoCrFeNiMn | FCC (random solid solution) | 245.48 (avg.) | Vacuum induction melting | hot-rolled + heat-treated | Not Specified | 0.1 | 625.6 | 126 |
| CoCrFeNiMn | FCC (single phase, coarse grained) | 250-500 100-300 | Thermite-type self-propagating high-temperature synthesis (centrifugal set-up) | as-sintered laser beam welded | | 0.1 0.1 | 362 349 | 90 90 |
| CoCrFeNiMn | FCC (no sign of martensitic transform.) | 41 | Vacuum induction melting | hot-rolled at 1373 K + solution-treated at 1073 K + water-quenched | | −1 | 585 | 250 |
| CoCrFeNiMn | Only microstructural characteristics Specified | 0.407 (median) 0.628 (median) | Powder metallurgy (ball milling process) | Spark plasma sintering (SPS) at 1150° C. for 5 min | | 0.1 0.1 | N/A (Bending test) | 495 450 |

5.1 Comparison Across Compositions, Process Parameters, Defect Levels, and Grain Sizes for a Given UTS Further Explanations of the Scatter 1. UTS≈1,100 MPa Variations in the defect level alone can result in ~2× variations in the endurance limit for the multi-variate data point, as noted in Table 9. At UTS≈1,100 MPa, the variations observed can additionally be explained in terms of variations in the grain size, microstructure and composition, per Table 10.

2. UTS≈1,340 MPa

At UTS≈1,340 MPa, the variations observed can similarly be explained in terms of variations in the microstructure, grain size, and processing parameters, per Table 9 and Table 10. One cannot expect the accurate prediction of the fatigue resistance, unless knowing parameters of the heat treatment process and the defect levels, in addition to the UTS.

5.2 Comparison Across Process Parameters, Defect Levels, Grain Sizes, and UTS for a Given Composition 1. Comparison for AlCoCrFeNi$_{2.1}$ We believe that the increments of the UTS and endurance limit, shown in Table 11, are—at least in part—caused by the lower defect level for the AlCoCrFeNi$_{2.1}$ cold-rolled and heat-treated eutectic HEA (EHEAw) composition. Since the EHEAw samples were annealed after cold-rolling, the grain sizes are likely similar. In addition to defect structures and grain sizes, the variations may be impacted by persistent slip bands in the micro-structure (FengGaoLeeMathes 2016), (AsmHandbook 1990).

2. Further Comparison for CoCrFeNiMn

Figure 27:
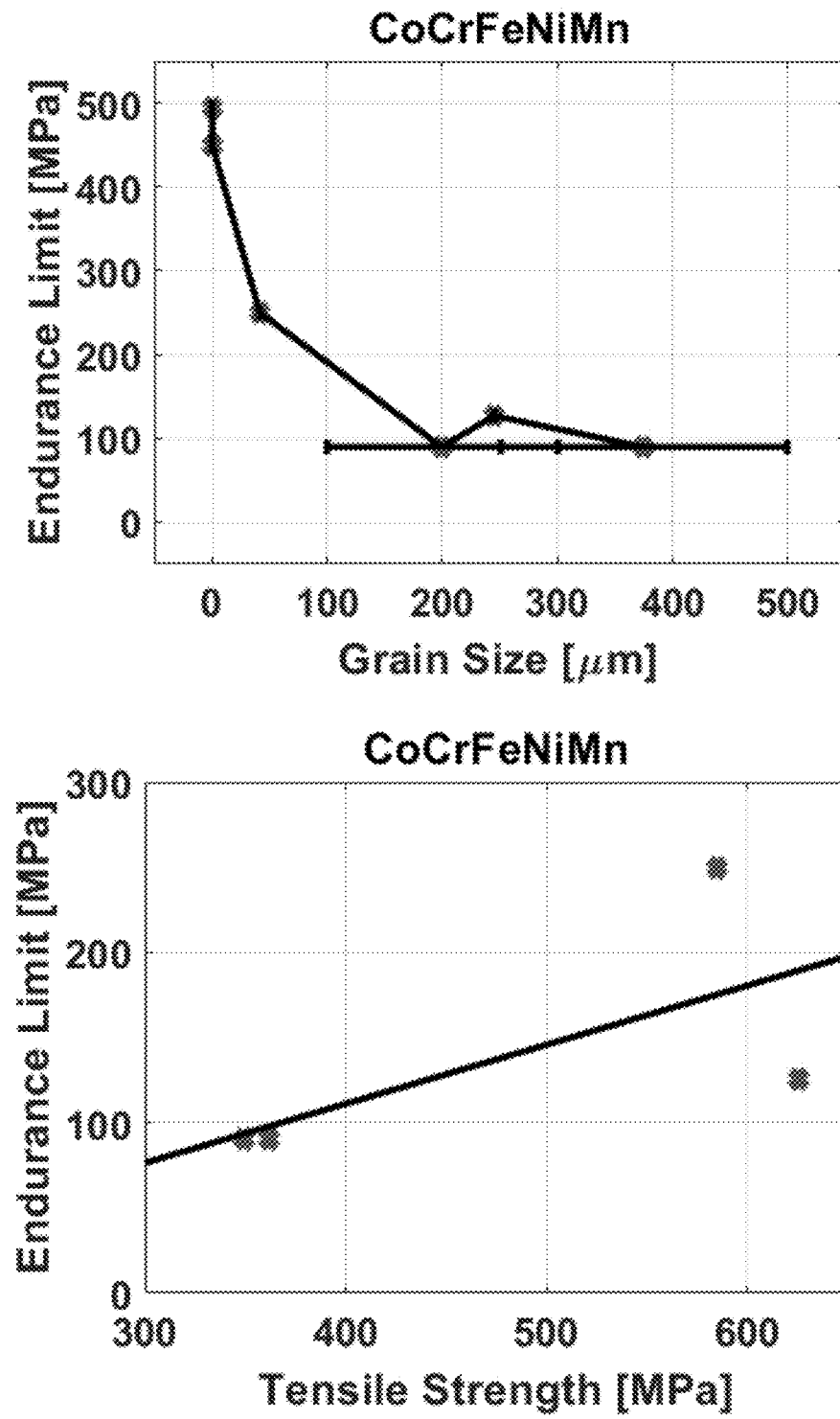
FIG. 27 captures analysis of the dependence of the endurance limit of CoCrFeNiMn (the Cantor alloy) on gain size (top) and tensile strength (bottom).

Similar to the case for AlCoCrFeNi$_{2.1}$, we believe that the hot-rolled and heat-treated process may have contributed to a little higher UTS and endurance limit for CoCrFeNiMn listed in Table 10 and FIG. 27, compared to the cases of as-sintered or laser-beam welded. But more importantly, we believe that the smaller grain size is resulting in a higher strength and endurance limit, per the Hall-Petch relation (Eq. (14)). The hot rolling and heat treatment may have given rise to smaller grain sizes, compared to sintering or laser beam welding. FIG. 27 demonstrates clear inverse correlation between the endurance limit and the grain size, but positive correlation between the endurance limit and the UTS. For information on the fatigue-crack growth behavior of CoCrFeNiMn, refer to (ThurstonGludovatzHohenwater 2017).

TABLE 11

Variations in endurance limits for as-cast eutectic HEA (EHEAc) and cold-rolled and heat-treated eutectic HEAs (ShuklaWangCottonMishra 2018).

| Composition | Micro-Structure | Grain Size [um] | Process | Defects Reported | Tensile Strength (MPa) | Endurance Limit (MPa) |
|---|---|---|---|---|---|---|
| AlCoCrFeNi2.1 EHEAc | FCC + BCC | Not Specified | as-cast | Not Specified | 1,057 | 374 |
| AlCoCrFeNi2.1 EHEAw | FCC + BCC | Not Specified | cold-rolled + heat-treated | Not Specified | 1,340 | 466 |

5.3 Comparison for 4340 Steel

Since both 4340 steel samples were heat treated, we expect similar defect levels. Judging from Table 9-Table 11, the difference in the tensile strength and endurance limit, listed in Table 12, likely is caused by the difference in the grain size, and possibly—depending on the annealing temperature (not specified in (GorsseHutchinson 2017))—microstructure (phases).

TABLE 12

Variations in endurance limits for 4340 steels (BrownHoMindlin 1979).

| Composition | Micro-structure | Grain Size [um] | Process | Defects Reported | Tensile Strength (MPa) | Endurance Limit (MPa) |
|---|---|---|---|---|---|---|
| 4340 Steel | Not Specified | Not Specified | Quenched & tempered at 538° C. | Not Specified | 1,260 | 335 |
| 4340 Steel | | | Annealed | | 745 | 170 |

6. Example 1: Prediction of Fatigue Endurance Limit

Figure 22:
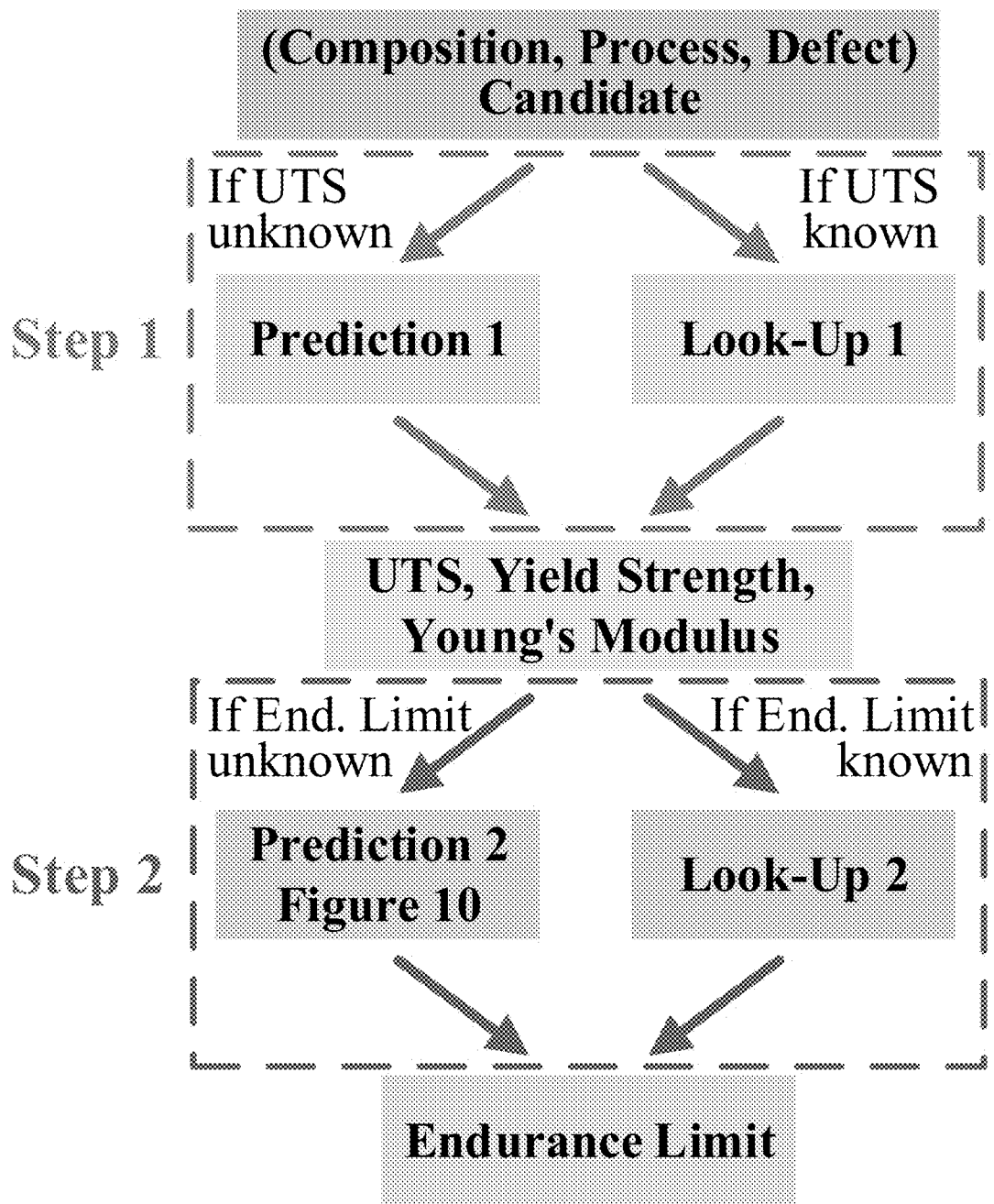
FIG. 22 presents overall methodology for deriving the output quantity of interest (the endurance limit) from the input sources (compositions, processes and defects).

The overall methodology for predicting the fatigue resistance is presented in FIG. 22. This is a two-stage prediction process, where we first determine the tensile strength, given an input combination, and then determine the fatigue resistance, given the tensile strength and the inputs.

FIG. 26 compares the high-cycle fatigue properties of HEAs to those of conventional alloys. The HEAs seem to generally result in higher UTS and endurance limits, compared to conventional alloys. Still, there is a lot of scatter in the data. But despite the scatter, the endurance limit seems primarily correlated with the UTS. Hence, by identifying compositions with larger UTS, one can expect greater fatigue resistance. A key to accurate prediction entails understanding, and properly accounting for (explaining), the sources of variations in the data.

The scatter in the data is caused by input sources, such as defect levels, process parameters, or grain sizes, which are not accounted for in the prediction model, or accounted for in the prediction model, but not available at the time of prediction.

The endurance limits in FIG. 26 represent multi-dimensional data points, which in addition to the UTS exhibit dependence on the grain size, process parameters, and defect characteristics.

6.1 Formulation of the Input Combinations

Our intent is to capture in the input sources that contribute to variations in the fatigue resistance (to variations in the output). In this invention, we like to model the input combination as $$\text{input combination}=(\text{composition},\text{heat treatment process},\text{defect level}). \quad (15)$$

Here defects are defined broadly such as to include inhomogenities, impurities, and unwanted features.

While we are primarily looking for compositions yielding attractive fatigue resistance, we will see (from Table 9) that the defect level also significantly impacts the fatigue resistance. Hence, the accurate prediction of the fatigue resistance (endurance limit) may be impossible, without knowing the defect information. Similarly, we preferably would like to determine the heat-treatment process that yields the least scatter in the fatigue resistance observed.

6.2 Estimating the Tensile Strength, Given an Input Combination

Step 1 in FIG. 22 summarizes the overall approach. If the UTS corresponding to a given input combination is known, we can apply a simple look-up. If the UTS corresponding to a given input combination is not known, we can apply prediction (interpolation or extrapolation), based on the nearest neighbors.

FIG. 18 captures a general model of physical dependencies for prediction of the UTS. This model is a generalization of the input sources modeled in Eq. (15). Capturing of the physical dependencies helps greatly in terms of the incorporation of a priori knowledge, derived from the underlying physics, and in terms of making the most of the—usually limited—input data available.

6.3 Arriving at the Fatigue Resistance, Given the Tensile Strength and the Remaining Inputs Step 2 in FIG. 22 summarizes the overall approach, for one embodiment of the invention. Here, we model the fatigue resistance (the fatigue endurance limit) as $$\text{endurance limit}=f(\text{UTS},\text{heat treatment process},\text{defect level}) \quad (16)$$

If the endurance limit corresponding to a given input combination is known, we can apply simple look-up. If the endurance limit corresponding to a given input combination is not known, we can predict the endurance limit, on basis of the estimated $$\text{UTS}(\text{composition},\text{heat treatment process},\text{defect level}) \quad (17)$$

as shown in FIG. 26.

The significant variations observed in FIG. 26 reinforce the need for the access to the relevant input data, for accurate prediction. To obtain the prediction accuracy within the measurement error (10%-20%), or within the accuracy limits on fatigue life expected for given parts, one may need to know quite a bit more about the input (configurational) parameters. An accurate prediction model seems to have the form $$\text{endurance limit}=f(\text{UTS},\text{process},\text{defect}(\text{process}),\text{grain}(\text{process}),\text{microstructure}(\text{process}),T\ldots) \quad (18)$$

where $$\text{UTS}=\text{UTS}(\text{composition},\text{heat treatment process},\text{defect level}(\text{process}),\text{grain size},T). \quad (19)$$

7. Example 2: Identification of Compositions Yielding High Tensile Strength

Figure 21:
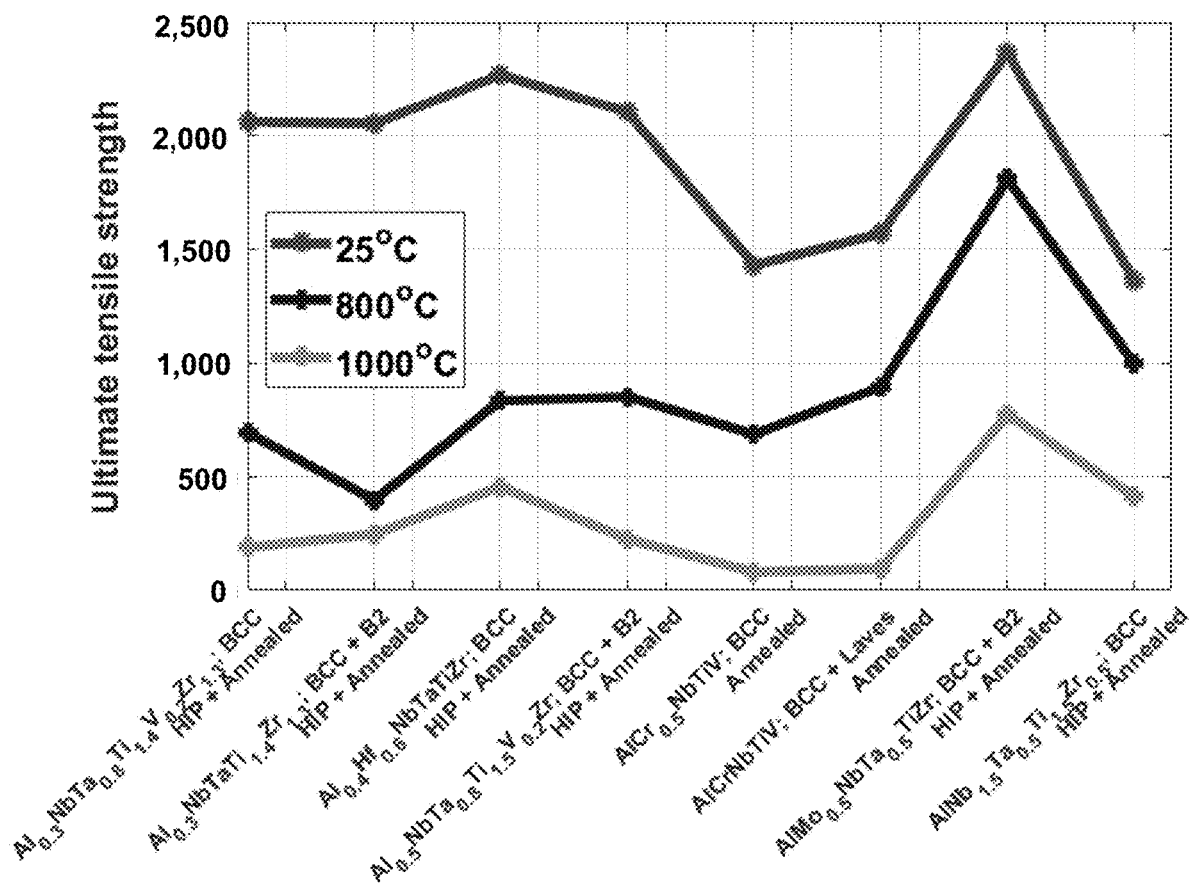
FIG. 21: Towards the characterization of temperature dependence of the ultimate tensile strength of HEAs. For a given temperature, the data points listed correspond to the same heat-treatment process.

7.1 Review of the Original Data Set—Rational for Restricting Analysis to Room-Temperature Data As illustrated in FIG. 21, the ultimate tensile strength exhibits the significant dependence on the temperature. While all compositions in FIG. 21 contained a BCC phase, and were subjected to some type of annealing, the tensile strength at 1,000° C. can be ~$\frac{1}{8}^{th}$ (~12%) to ~$\frac{1}{3}^{rd}$ (~33%) of the tensile strength at room temperature. With this in mind, and to maintain consistency across compositions, we elected only to apply our optimization framework to tensile strengths at room temperature. Our original data set, listed in Table 13, contains some 24 compositions that yield relatively-high UTS at room temperature. We derived two feature sets, hereafter referred to as A and B from the original data set in Table 13:

$$\text{Feature Vector } A=x_A=[\%\,Al,\%\,Mo,\%\,Nb,\%\,Ti,\%\,V,\%\,Ta,\%\,Zr,\%\,Hf] \quad (20)$$

$$\text{Feature Vector } B=x_B=[\%\,Al,\%\,Mo,\%\,Nb,\%\,Ti,\%\,V,\%\,Ta,\%\,Zr,\%\,Hf,\%\,Cr]. \quad (21)$$

We have available nineteen (19) instances of the feature vector, A, and twenty two (22), of the feature vector, B. While the set of input data may seem small, we will show that it suffices for the meaningful prediction, provided that a suitable optimization technique is selected.

TABLE 13

Compositions from the original and enhanced databases yielding the high UTS at room temperature (25° C.). Compositions No. 1 - No. 36 were all fabricated using arc melting.

| No. | Composition | Microstructure | Process | Select Process Specifics | UTS | Example (Data Set) | |
|---|---|---|---|---|---|---|---|
| 1 | $Al_{0.25}NbTaTiZr$ | BCC + B2 | HIP + anneal | HIP: 2 hr., 1400° C. | 1,830 MPa | A, B, C | Original |
| 2 | $Al_{0.2}MoTaTiV$ | BCC | As-cast | N/A. Remelted a few x | 1,249 MPa | A, B, C | Database |
| 3 | $Al_{0.3}NbTa_{0.8}Ti_{1.4}V_{0.2}Zr_{1.3}$ | BCC | HIP + anneal | HIP: 2 hr., 1200° C. | 2,061 MPa | A, B, C | |
| 4 | $Al_{0.3}NbTaTi_{1.4}Zr_{1.3}$ | 2 BCC | HIP + anneal | HIP: 2 hr., 1200° C. | 2,054 MPa | A, B, C | |
| 5 | $Al_{0.4}Hf_{0.6}NbTaTiZr$ | BCC | HIP + anneal | HIP: 2 hr., 1200° C. | 2,269 MPa | A, B, C | |
| 6 | $Al_{0.5}Mo_{0.5}NbTa_{0.5}TiZr$ | BCC + B2 | HIP + anneal | HIP: 2 hr., 1400° C. | 2,460 MPa | A, B, C | |
| 7 | $Al_{0.5}NbTa_{0.8}Ti_{1.5}V_{0.2}Zr$ | 2 BCC | HIP + anneal | HIP: 2 hr., 1200° C. | 2,105 MPa | A, B, C | |
| 8 | $Al_{0.6}MoTaTiV$ | BCC | As-cast | N/A. Remelted a few x | 1,033 MPa | A, B, C | |
| 9 | $AlCr_{0.5}NbTiV$ | BCC | Annealed | Homog: 24 hr., 1200C | 1,430 MPa | B, C | |
| 10 | $AlCrNbTiV$ | BCC + Laves | Annealed | Homog: 24 hr., 1200C | 1,570 MPa | B, C | |
| 11 | $AlMo_{0.5}NbTa_{0.5}TiZr$ | BCC + B2 | HIP + anneal | HIP: 2 hr., 1400° C. | 2,370 MPa | A, B, C | |
| 12 | $AlNb_{1.5}Ta_{0.5}Ti_{1.5}Zr_{0.5}$ | BCC | HIP + anneal | HIP: 2 hr., 1400° C. | 1,367 MPa | A, B, C | |
| 13 | $AlNbTa_{0.5}TiZr_{0.5}$ | B2 | HIP + anneal | HIP: 2 hr., 1400° C. | 1,357 MPa | A, B, C | |
| 14 | $AlNbTiV$ | BCC | Annealed | Homog: 24 hr., 1200 C. | 1,280 MPa | A, B, C | |
| 15 | $AlNbTiVZr$ | B2 + Al3Zr5 + Laves | Annealed | Homog: 24 hr., 1200 °C 99.9 + % purities; | 1,675 MPa | A, B, C | |
| 16 | $AlNbTiVZr_{0.1}$ | B2 + Al3Zr5 | Annealed | Prior to annealing, the | 1,395 MPa | A, B, C | |

TABLE 13-continued

Compositions from the original and enhanced databases yielding the high UTS at room temperature (25° C.). Compositions No. 1 - No. 36 were all fabricated using arc melting.

| No. | Composition | Micro-structure | Process | Select Process Specifics | UTS | Example (Data Set) | |
|---|---|---|---|---|---|---|---|
| 17 | AlNbTiVZr$_{0.25}$ | B2 + Al3Zr5 | Annealed | samples were | 1,480 MPa | A, B, C | |
| 18 | AlNbTiVZr$_{1.5}$ | B2 + Al3Zr5 + Laves | Annealed | incapsulated in vacuumed ($10^{-2}$ Torr) quartz tubes. | 1,550 MPa | A, B, C | |
| 19 | CrHfNbTiZr | BCC + Laves | Annealed | 973 K for 600 sec | 1,908 MPa | B, C | |
| 20 | Hf$_{0.5}$Mo$_{0.5}$NbTiZr | BCC | As-cast | N/A. Melt 5 times | 1,538 MPa | A, B, C | |
| 21 | MoTaTiV | BCC | As-cast | N/A. Remelted a few x | 1,454 MPa | A, B, C | |
| 22 | HfNbTaTiZr | BCC | Cold roll + anneal | 1373 K anneal in He atmos. for 5 hr | 1,095 MPa | A, B, C | |
| 23 | CrMo$_{0.5}$NbTa$_{0.5}$TiZr | 2BCC + FCC | HIP + anneal | 1723 K/207MN/m$^2$/3 hr | 2,046 MPa | C | Enhanced |
| 24 | MoNbTaV | BCC | As-cast | N/A. Remelted a few x | 2,400 MPa | C | Database |
| 25 | CrNbTiVZr | BCC + Laves | HIP + anneal | HIP at 1473 K & | 1,725 MPa | C | |
| 26 | CrNbTiZr | BCC + Laves | HIP + anneal | 207 MPa for 2 hr. | 1,575 MPa | C | |
| 27 | HfNbTiVZr | BCC + Unknow | As-cast | N/A. Remelted a few x | 1,463 MPa | C | |
| 28 | MoNbTiV$_{0.25}$Zr | BCC | As-cast | N/A. Remelted a few x | 3,893 MPa | C | |
| 29 | MoNbTiV$_{0.5}$Zr | BCC | As-cast | N/A. Remelted a few x | 3,307 MPa | C | |
| 30 | MoNbTiV$_{0.75}$Zr | BCC | As-cast | N/A. Remelted a few x | 3,929 MPa | C | |
| 31 | MoNbTiV$_{1.5}$Zr | 2 BCC | As-cast | N/A. Remelted a few x | 3,300 MPa | C | |
| 32 | MoNbTiV$_2$Zr | 2 BCC | As-cast | N/A. Remelted a few x | 3,176 MPa | C | |
| 33 | MoNbTiV$_3$Zr | 2 BCC | As-cast | N/A. Remelted a few x | 2,508 MPa | C | |
| 34 | MoNbTiVZr | BCC | As-cast | N/A. Remelted a few x | 3,828 MPa | C | |
| 35 | MoNbTiZr | BCC | As-cast | N/A. Remelted a few x | 3,450 MPa | C | |
| 36 | MoTaTiV | BCC | As-cast | N/A. Remelted a few x | 1,454 MPa | C | |
| 37 | Al | | | Purity: 99.99% [44] | 45 MPa | C | |
| 38 | Mo | | | Annealed [45] | 324 MPa | C | |
| 39 | Nb | | | Annealed [45] | 275 MPa | C | |
| 40 | Ti | | | Purity 99.9% [44] | 235 MPa | C | |
| 41 | V | | | Cold rolled [44] | 828 MPa | C | |
| 42 | Ta | | | Cold worked [45] | 900 MPa | C | |
| 43 | Zr | | | Typical [45] | 330 MPa | C | |
| 44 | Hf | | | Typical [45] | 485 MPa | C | |
| 45 | Cr | | | As-swaged [44] | 413 MPa | C | |

7.2 Analysis of Variations in UTS for the Pure Elements Selection of a Suitable Prediction Model In order to develop insight into the causes of variations in tensile strengths for the pure elements comprising feature vectors A and B, and for the identification of a model for predicting compositions yielding high tensile strengths, and presumably attractive fatigue resistance, we present FIG. 19 and FIG. 20. FIG. 19 shows that processing conditions and purity can contribute to variations in tensile strengths of Al of ~3× and of ~4× in the tensile strength of Co. FIG. 20 similarly illustrates that processing methods have significant influence on the tensile strength of V and Cr. For the Vanadium, the variations in the tensile strength are ~2×, and for the Chromium, we are looking at variations of up to ~5× (!) This trend suggests that an accurate model for predicting the tensile strength may indeed have the form of Eq. (19). But for relative comparison of tensile strengths across compositions, for the same heat-treatment process and defect levels, and at fixed (room) temperature, the model $$UTS = UTS(\text{composition}) \quad (22)$$

may suffice. For the prediction presented in FIG. 36 and the experimental verification outlined in FIG. 37, we employ the prediction model of Eq. (UTS=UTS(composition)(22).

7.3 Selection of a Suitable Optimization Technique

Given the small size of the data set in Table 13, it suffices to say that we are not ready for traditional ML models. Models, such as artificial neural networks, decision trees, support vector machines, Bayesian networks, or genetic algorithms, tend to be effective in organizing and extracting complex patterns from large sets of data, as noted above. But for the application and limited data set at hand, it makes sense to select a simple linear-prediction model, multi-variate linear regression, to begin with, and build from there. As suggested by Agrawal et. al. (AgrawalDeshpande 2014), changing the method may not change the results that much. According to FIG. 5 and Table 2 in (AgrawalDeshpande 2014), the linear regression yields $R^2$ of 0.963, when predicting the fatigue strength of the stainless steel, compared to $R^2$ of 0.972 for the artificial neural networks.

Our intent is to start out with the statistical (linear) regression analysis, and account for the underlying sources of (input) variations. We intend to then expand the model, and add non-linearities, based on the underlying physics, and as necessitated by the application at hand and the data available.

7.4 Setting Up the Optimization Problem

1. Multi-Variate Linear Regression

When applying the linear regression, we solve a constrained optimization problem of the form $$\min_x \|Bx - y\|_2^2 \text{ such that } \begin{array}{l} 0 \leq x_i \leq 100 \\ \sum_i x_i = 100 \end{array}. \quad (23)$$

Here, y represents a vector of tensile-strength values, but B the training set of compositions [a stacked version of x vectors, derived from Table 13]. To solve this constrained optimization problem, one can use a function from Matlab® or Octave called lsqlin(·).

2. Quadratic Regression with Diagonal Matrix (for Comparison)

When applying the quadratic regression, we model the UTS (y) as $$y = x^T A x + b^T x + c. \tag{24}$$

Assuming a general A matrix and a 9-element feature vector ($x_B$), this model consists of $$9 + 9 \times 9 + 1 = 91 \text{ parameters.} \tag{25}$$

Using an unconstrained model with 91 parameters to fit to the data sets in Table 13 does not make sense, since the number of model parameters greatly exceeds the number of data points. Hence, we should be able to fit the model perfectly to the data. In order to reign in the model complexity, we restrict the A matrix to a diagonal form. In this case, the model consists of $$9 + 9 + 1 = 19 \text{ parameters,} \tag{26}$$

i.e., fewer parameters than listed for Data Set C in Table 13.

In the case of a diagonal A matrix, $$A = \begin{bmatrix} a_{11} & 0 & \cdots & 0 \\ 0 & a_{22} & \cdots & 0 \\ 0 & 0 & \cdots & 0 \\ \vdots & & \ddots & \vdots \\ 0 & 0 & \cdots & a_{mm} \end{bmatrix}, \tag{27}$$

the quadratic regression can be cast as an enhanced version of standard linear regression. To accomplish this process, we write the training set, as shown below:

$$y_1 = a_{11} x_1(1) x_1(1) + a_{22} x_1(2) x_1(2) + \tag{28}$$
$$a_{33} x_1(3) x_1(3) + \ldots + a_{99} x_1(9) x_1(9) + b^T x_1 + c$$
$$y_2 = a_{11} x_2(1) x_2(1) + a_{22} x_2(2) x_2(2) + a_{33} x_2(3) x_2(3) +$$
$$\ldots + a_{99} x_2(9) x_2(9) + b^T x_2 + c$$
$$y_3 = a_{11} x_3(1) x_3(1) + a_{22} x_3(2) x_3(2) + a_{33} x_3(3) x_3(3) +$$
$$\ldots + a_{99} x_3(9) x_3(9) + b^T x_3 + c$$
$$\ldots$$
$$y_N = a_{11} x_N(1) x_N(1) + a_{22} x_N(2) x_N(2) +$$
$$a_{33} x_N(3) x_N(3) + \ldots + a_{99} x_N(9) x_N(9) + b^T x_N + c.$$

We then rearrange the terms as follows:

$$y_1 = c + x_1(1) x_1(1) a_{11} + x_1(2) x_1(2) a_{22} + \tag{29}$$
$$x_1(3) x_1(3) a_{33} + \ldots + x_1(9) x_1(9) a_{99} + x_1^T b$$
$$y_2 = c + x_2(1) x_2(1) a_{11} + x_2(2) x_2(2) a_{22} +$$
$$x_2(3) x_2(3) a_{33} + \ldots + x_2(9) x_2(9) a_{99} + x_2^T b$$
$$y_3 = c + x_3(1) x_3(1) a_{11} + x_2(3) x_2(3) a_{22} + x_3(3) x_3(3) a_{33} +$$
$$\ldots + x_3(9) x_3(9) a_{99} + x_3^T b$$
$$\ldots$$
$$y_N = c + x_N(1) x_N(1) a_{11} + x_N(2) x_N(2) a_{22} +$$
$$x_N(3) x_N(3) a_{33} + \ldots + x_N(9) x_N(9) a_{99} + x_N^T b.$$

This process results in the linear system $$\begin{bmatrix} y_1 \\ y_2 \\ y_3 \\ \vdots \\ y_N \end{bmatrix} = \begin{bmatrix} 1 & x_1(1)x_1(1) & x_1(2)x_1(2) & \ldots & x_1(9)x_1(9) & x_1^T \\ 1 & x_2(1)x_2(1) & x_2(2)x_2(2) & \ldots & x_2(9)x_2(9) & x_2^T \\ 1 & x_3(1)x_3(1) & x_3(2)x_3(2) & \ldots & x_3(9)x_3(9) & x_3^T \\ 1 & \vdots & \vdots & \ddots & \vdots & \vdots \\ 1 & x_N(1)x_N(1) & x_N(2)x_N(2) & \ldots & x_N(9)x_N(9) & x_N^T \end{bmatrix} \begin{bmatrix} a_{11}^C \\ a_{22} \\ a_{33} \\ \vdots \\ a_{99} \\ b \end{bmatrix}. \tag{30}$$

$$\bar{y} = \tilde{x} \bar{b}. \tag{31}$$

The least-squared solution of Eq. (30) can now be obtained in closed form as.

$$\bar{b} = (\tilde{X}^T \tilde{X})^{-1} \tilde{X}^T \bar{y} \tag{32}$$

7.5 Prediction of Composition Yielding Higher UTS, and Presumably More Attractive Fatigue Resistance, than Previously Observed Based on Data Sets A and B FIG. 23 and FIG. 24 illustrate the process of predicting compositions yielding higher UTS, and presumably higher fatigue resistance, based on Data Sets A and B. The prediction process consists of three main steps:

First, we identify the composition with the highest measured UTS, which in the case of Data Sets A and B is $Al_{0.5}Mo_{0.5}NbTa_{0.5}TiZr$, with the measured UTS of 2,460 MPa.

Second, we decrease the concentrations corresponding to negative (or small, positive) values of the a vector. In case of FIG. 23 and FIG. 24 this results in decreasing the concentrations of Ti and Hf. But the concentration of Hf in $Al_{0.5}Mo_{0.5}NbTa_{0.5}TiZr$ is already 0.0%, so the Hf cannot be decreased further.

Third, we increase the concentration of elements corresponding to the largest values of the weighting vector, a. These elements exhibit the largest correlation with (or contributions to) the UTS observed. Hence, by increasing these elements, one can expect the largest relative increase in the UTS. In an effort to maximize the UTS, this process results in increasing the concentrations of Nb and Zr (and for Data Set B, the concentration of Cr).

Both Data Sets A and B give rise to the same, predicted composition ($Al_{0.5}Mo_{0.5}Nb_{1.5}Ta_{0.5}Zr_{1.5}$). This consistency suggests that the prediction algorithm may be somewhat immune to minor variations or redundancy (or even discrepancy) in the input data.

Next, we assess the predictive capability of the regression model. The top two figures in FIG. 36 show the predicted UTS as a function of the measured UTS. Here we are applying the same data points from Table 13 (19 and 22, respectively) for training and testing. Even so, we are looking at $R^2 = 0.592$ and normalized standard deviation per data point of 15.0 MPa for Data Set A. Similarly, for Data Set B, we are looking at $R^2 = 0.591$ and normalized standard deviation of 12.2 MPa. We attribute the spread observed to the fact we are obtaining the data from the open literature, and that variations primarily in the process, but also the microstructure, shown in Table 13, are not accounted for in the prediction model in Eq. (22). FIG. 19 and FIG. 20 clearly indicate that the heat-treatment process applied can significantly impact the UTS observed.

7.6 Towards Understanding What is Causing Limitations of the Model—Analysis of Variance (Outliers)

For the purpose of confirming the conjecture about variance in the post-processing (heat-treatment process) applied being a major cause of the variance observed in FIG. 36, we pick a few outliers for further analysis. We are in particular interested in identifying (analyzing) the processing applied to the outliers. Table 14 and Table 15 summarize our analysis of the annotated outliers from FIG. 36. Our anticipated outcome can be characterized as follows:

For outliers above the red lines in FIG. 36 corresponding to $$\text{Measured(UTS)} < \text{Predicted(UTS)}, \quad (32)$$

we expected poor processing (no heat-treatment process, or a cheap process) to be applied.

Here, the other compositions, esp. the ones with good heat treatments, impact the overall weighting (the a vector) such as to improve the overall prediction of the UTS for this data point.

But for outliers below the red lines in FIG. 36, corresponding to $$\text{Measured(UTS)} > \text{Predicted(UTS)}, \quad (33)$$

we thought good processing might have been applied. Here, the other compositions, esp. the ones with poor heat treatment, impact the overall weighting (the a vector) such as to degrade the overall prediction of the UTS for this data point.

The results from Table 14 indeed serve to confirm our conjecture: The outlier, $Al_{0.4}Hf_{0.6}NbTaTiZr$, from FIG. 36 falls below the red line, and has a reasonably-good heat treatment applied (HIP for 2 hours at. 1,200° C.). The other outlier from FIG. 36, $Hf_{0.5}Mo_{0.5}NbTiZr$, shows up quite a bit above the red line, and has no heat-treatment process applied.

The results from Table 15 further serve to confirm our conjecture: The outlier, AlCrNbTiV, from FIG. 36 falls below the red line, and has a reasonably-good heat treatment applied (annealed for 24 hours at 1,200° C.). The other outlier from FIG. 36, MoNbTiZr, shows up somewhat above the red line, and has no heat-treatment process applied. [For full disclosure, the compositions within the green circle had no heat-treatment applied, but yet appeared beneath the red line. This trend may have had to do with the fact that none of the compositions with highest UT Shad heat-treatments applied.]

Overall, these observations strengthen our belief in that the prediction accuracy, measured in terms of $R^2$ and the standard deviation normalized per data point, is primarily limited by the quality of (variance in) the input data. These limitations in the prediction accuracy are consistent with the variations observed in Table 13, FIG. 19 and FIG. 20. The observations further underline the importance of selecting an optimization technique suitable for the application at hand and data available, and suggest that multi-variate regression is indeed suitable for analysis of the tensile strength.

The methodology presented here is not specific to the tensile strength. Comparison, such as Eq. (32) and Eq. (33), can be presented as a part of outlier analysis for other quantities of interest, as long as combinations of predicted and measured values are available.

TABLE 14

Analysis of .properties, in particular heat treatment properties, corresponding to two of the annotated outliers in FIG. 36.

| Outlier | $Al_{0.4}Hf_{0.6}NbTaTiZr$ | $Hf_{0.5}Mo_{0.5}NbTiZr$ |
|---|---|---|
| Process | HIP + anneal | As-cast |
| Process Specific | HIP: 2 hr., 1,200° C. | N/A. Re-melt 5 times |
| $UTS_{meas}$ | 2,269 MPa | 1,538 MPa |
| $UTS_{predict}$ | 1,657 MPa | 2,700 MPa |
| Above or Below Red Line in FIG. 36? | Below | Above |
| Expectation | Since $UTS_{meas} > UTS_{predict}$, we expect good processing applied | Since $UTS_{meas} < UTS_{predict}$, we expect poor processing applied |
| Observation | Indeed, here a reasonably good heat treatment process has been applied | Indeed, here no heat treatment process was applied |

TABLE 15

Analysis of .properties, in particular heat treatment properties, corresponding to other two of the annotated outliers in FIG. 36.

| Outlier | AlCrNbTiV | MoNbTiZr |
|---|---|---|
| Process | Annealed | As-cast |
| Process Specific | Homogenized for 24 hr. at 1,200° C. | N/A. Remelted a few times. |
| $UTS_{meas}$ | 1,570 MPa | 3,450 MPa |
| $UTS_{predict}$ | 1,043 MPa | 3,615 MPa |
| Above or Below Red Line in FIG. 36? | Below | Above |
| Expectation | Since $UTS_{meas} > UTS_{predict}$, we expect good processing applied | Since $UTS_{meas} < UTS_{predict}$, we expect poor processing applied |
| Observation | Indeed, here a reasonably good heat treatment process has been applied | Indeed, here no heat treatment process was applied |

7.7 Assessing the Need for a More Sophisticated Prediction Model Further Analysis of Data Set C 1. Criterion for Assessment of Suitability of the Linear Regression, Upon Addition of New Data The results for Data Sets A and B in FIG. 36 show that one can predict the UTS, using multi-variate linear regression, but that the variance is somewhat large, for reasons stated above.

Further assessment of the suitability of the linear regression can be obtained, by looking at the error margins, upon the addition of new data: If the variances decrease (improve), upon the addition of new data, then linear regression is a good model. If the variance stays approximately the same, then the linear regression is a questionable technique. But if the variance increases (deteriorates), upon the addition of new data, then we may need to look for another method.

2. Prediction of Compositions with Higher UTS than Previously Observed, Based on Data Set C FIG. 25 illustrates the process of predicting compositions yielding higher UTS, and presumably higher fatigue resistance, than previously observed, based on Data Set C from Table 13. The prediction process consists of the same three, main steps, as the prediction in FIG. 23 and FIG. 24. The 4,847.1 MPa tensile strength for the predicted composition, MoNbZr, is 918 MPa higher than the highest UTS that has been previously observed (which is 3,929 MPa, observed for $MoNbTiV_{0.75}Zr$).

If desired, one can include the tensile strength of the pure elements comprising Feature Vector B, such as to introduce natural "barriers", which—together with the measured compositions—can limit the extent of the extrapolation. The nine (9) pure elements in feature vector B provide references, which one can compare against, during the extrapolation.

When expanding the data set, we considered also expanding the feature vector, by adding Co, Fe, and Ni. But eventually, we decided against it. While expanding the feature vector would have allowed us to introduce at least forty (40) additional compositions, and the addition of Cu would have allowed us to introduce several new compositions on top of that, all of these compositions corresponded to lower UTS than the highest UTS observed in Table 13.

cated than linear regression (e.g., quadratic regression), we still believe the overall accuracy is primarily limited by variations in the inputs. This assessment is motivated by FIG. 19 and FIG. 20.

7.8 Verifying Feasibility of the Predicted Compositions Empirical Rules

Table 16 captures the outcomes from applying the empirical rules of (ZhangZhou 2008), (FengGaoLeeMathes 2016) to the formation of the predicted compositions, $Al_{0.5}Mo_{0.5}Nb_{1.5}Ta_{0.5}Zr_{1.5}$ and MoNbZr.

TABLE 16

Assessment of viability of the predicted compositions ($Al_{0.5}Mo_{0.5}Nb_{1.5}$ $Ta_{0.5}Zr_{1.5}$ and MoNbZr) through the application of empirical rules (ZhangZhou 2008).

| Alloy | $Al_{0.5}Mo_{0.5}NbTa_{0.5}TiZr$ | $Al_{0.5}Mo_{0.5}Nb_{1.5}Ta_{0.5}Zr_{1.5}$ | $MoNbTiV_{0.75}Zr$ | MoNbZr |
|---|---|---|---|---|
| $\delta_r$ (%) | 4.41 | 4.89 | 5.65 | 5.56 |
| $\Delta H_{mix}$ (kJ/mol) | −10.52 | −10.17 | −2.70 | −3.56 |
| $\Delta S_{mix}$ (J/K/mol) | 14.43 | 12.18 | 13.33 | 9.13 |
| $\Omega$ | 3.16 | 2.89 | 11.79 | 6.66 |

Out of these additional compositions considered, the UTS, which came closest to the composition in Table 13 with the highest UTS ($MoNbTiV_{0.25}Zr$ with UTS of 3,893 MPa), was AlCoCrFeNi, which exhibited UTS of 3,531 MPa. Out of the additional compositions considered, a dozen or so exhibited UTS in the range of 2,500-3,200 MPa. But very few measured at higher UTS.

3. Suitability of Linear Regression for Data Set C

To the bottom left, FIG. 36 presents results from applying the multi-variate linear regression to Data Set C. Based on the figure, and $R^2$=0.77, it does seem that the data points are more or less following linear regression. But the results also may not be conclusive; still more data may be necessary. Although quadratic dependence is not apparent in the figure, such (weak?) dependence may still be present in the data.

When comparing the accuracy of the fit for the linear regression for Data Sets B and C, we notice that the normalized standard deviation per data point has decreased somewhat (from 12.0 MPa to 11.1 MPa). Applying the criterion above, this trend suggests that linear regression is a reasonably-good technique. Linear regression seems to provide the reasonably-good description of the data.

4. Suitability of Quadratic Regression for Data Set C

To the bottom right, FIG. 36 presents results from applying quadratic regression, with the diagonal A matrix per Eqs. (24) and (27), to Data Set C. Judging from the figure, $R^2$=0.94, and the normalized standard deviation of only 5.6 MPa per data point, it may seem that the prediction accuracy is limited by the prediction method more so than the variance in the inputs. Note though that, given limitations in the availability of the input data, we are using Data Sets A, B, and C (the same data sets) both for training and testing. Note also that the linear regression involves 10 model parameters, but the quadratic regression 19, per Eq. (26). Hence, the improvement in the accuracy of the fit, in case of the quadratic regression, is accomplished in part by fitting data to the 9 new model parameters. While quadratic regression with a diagonal matrix may indeed be a good technique for the application at hand, proper characterization of the relative merits of linear vs. quadratic regression will require separate data sets for training and testing. Further, although we may have sufficient data for a technique more sophisti- 1. Expected Properties of $Al_{0.5}Mo_{0.5}Nb_{0.5}Ta_{0.5}Zr_{1.5}$, Based on the Empirical Rules By comparing the calculated parameters for the atomic difference, $\delta_r$, and the enthalpy of mixing, $\Delta H_{mix}$, from Table 16 to FIG. 2 from (ZhangZhou 2008), one can see that a solid solution will likely form both in the predicted composition, $Al_{0.5}Mo_{0.5}Nb_{0.5}Ta_{0.5}Zr_{1.5}$, and in the reference composition, $Al_{0.5}Mo_{0.5}NbTa_{0.5}TiZr$. However, the predicted and reference compositions fall near the boundary between S and S' regions in FIG. 2 from (ZhangZhou 2008). This trend suggests a small amount of the ordered solid solution precipitates may also form as a minor phase. We expect $Al_{0.5}Mo_{0.5}Nb_{1.5}Ta_{0.5}Zr_{1.5}$ to be a stable composition with two types of phases.

2. Expected Properties of MoNbZr, Based on the Empirical Rules

Figure 2:
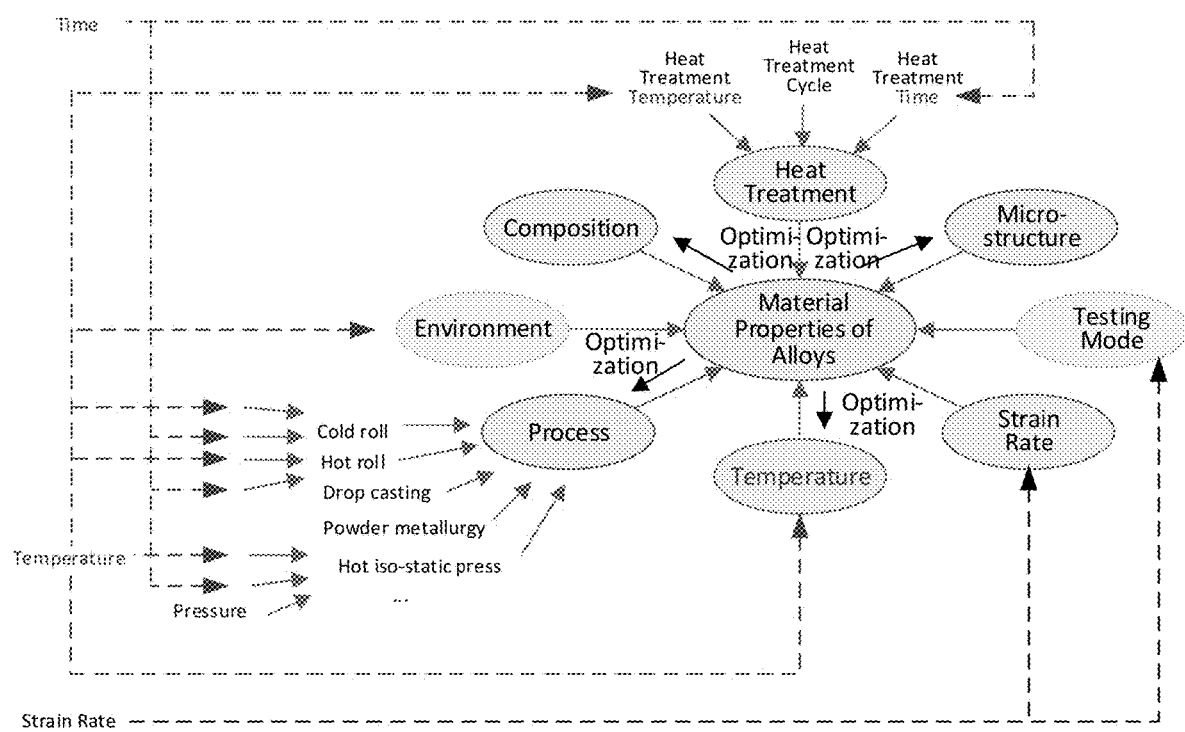
FIG. 2 presents a more detailed version of FIG. 1, one specific to fatigue properties, and one that illustrates dependence between the sources.

Again, by comparing the calculated parameters for the atomic difference, Sr, and the enthalpy of mixing, $\Delta H_{mix}$, from Table 16 to FIG. 2 from (ZhangZhou 2008), one notices that the predicted composition, MoNbZr, sits in the middle of the S' region in FIG. 2, which suggests the composition has high chance of forming a solid solution main phase with ordered solid solution precipitates.

Figure 37:
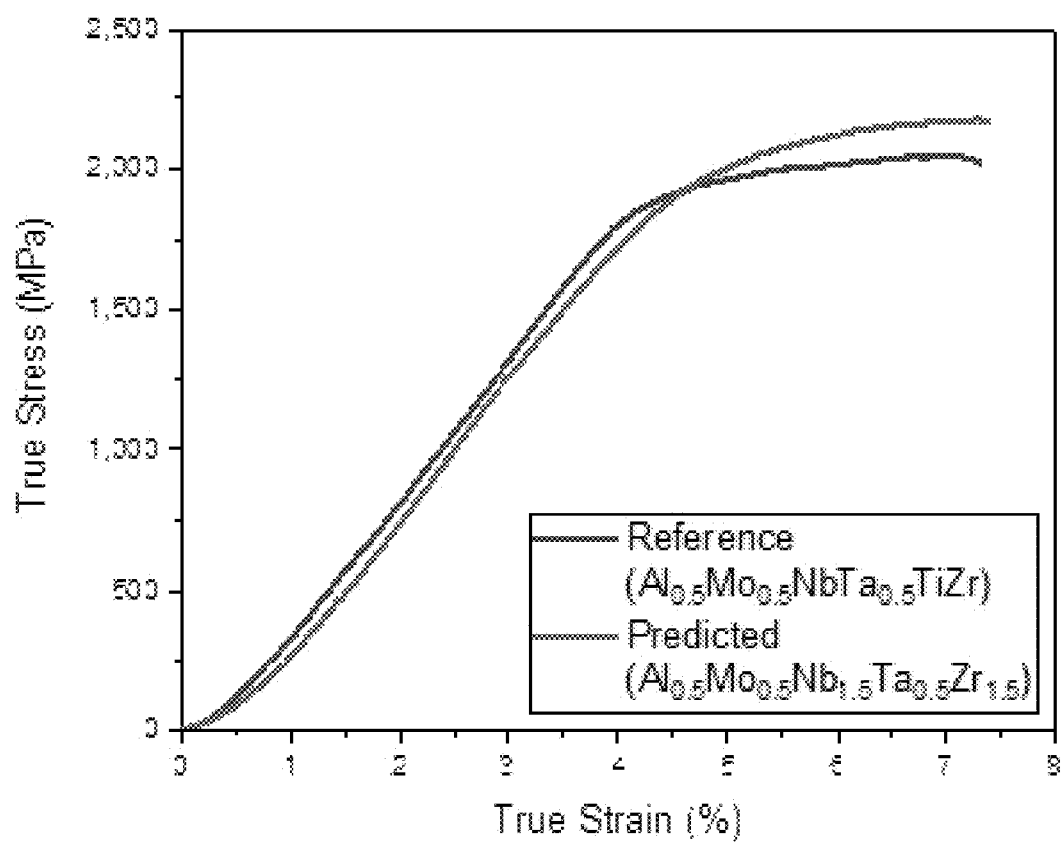
FIG. 37 presents results from experimental verification of superior tensile strength of the predicted composition (Al0.5Mo0.5Nb1.5Ta0.5Zr1.5) over the reference composition (Al0.5Mo0.5NbTa0.5TiZr). Coupons for both compositions were prepared through arc melting and with no heat treatment applied.

7.9 Experimental Verification of Predicted Compositions—$Al_{0.5}Mo_{0.5}Nb_{1.5}Ta_{0.5}Zr_{1.5}$ and MoNbZr FIG. 37 summarizes results from the experimental verification of the strength of the predicted composition, $Al_{0.5}Mo_{0.5}Nb_{1.5}Ta_{0.5}Zr_{1.5}$, in comparison to the reference, $Al_{0.5}Mo_{0.5}NbTa_{0.5}TiZr$. We conclude from the experimental results in FIG. 37 that the candidate composition indeed exhibits higher UTS than the reference, hence confirming the outcome of our prediction. Coupons for both the predicted and reference compositions were prepared, using arc melting and compression testing, for as-cast samples, and with no heat treatment applied. The casted samples had the initial diameter of a quarter inch (6.27 mm) based on the mold used. The diameter of the samples was then decreased by grinding the cylindrical surfaces to diameter of 4-5 mm, in order to obtain higher stress, and ultimately break the samples, using a mechanical compression testing machine with maximum force of 15,000 lbs. From the compression tests, it turned out that the predicted composition had relatively higher yield strength and fracture strength than the reference, as shown in FIG. 37. But both compositions were very brittle. Reminiscent of the trade-off between strength and ductility, this came as no surprise.

8. Example 3: Prediction of Fatigue Life (Stress Life or Strain Life) and Crack Growth 8.1 Prediction of Fatigue Life Remaining (S/N Curve), in Presence of No Cracks 1. Objective For the triplet (process,stress applied,cycles to failure), (34)

the goal is to accurately infer the "process" parameter from the combination (stress applied,cycles to failure), (35)

in order to properly differentiate between "process" categories.

Similarly, we can look to estimate "cycles to failure" (fatigue life) from the combination (process, stress applied), or "stress applied" (fatigue strength) from the combination (process, cycles to failure).

2. Method

The method, presented in FIG. 36, is analogous to the method used for prediction of the endurance limit (see Eq. (16)-Eq. (19)). The main difference is that here we are taking the stress applied as an additional input parameter. The method will be essentially the same as for predicting the endurance limit, except here we are doing separate prediction at each stress level.

3. Metric Used to Measure Success:

We will characterize quality in terms of the variance of the predictor or the MSE.

The variance in the system output, A y, for the system model in Eq. (1), is in part determined by the variance in the system input, A k, and in part by the model. In case of independent inputs, the variance in the system output can be modeled as $$\Delta y_i = \sum_{j=1}^{P} \frac{\partial f}{\partial x_j} \Delta x_j. \qquad (36)$$

4. Expected Results

Defects are easier to introduce with AM. Hence, we expect more scatter in S/N data for AM than for casting.

8.2 Prediction of Fatigue Life Remaining, Given a Crack

Fatigue life, defined in terms of the number of cycles, N, in the presence of cracks, is usually estimated as $$N = \int_{a_0}^{a_f} \left(\frac{dN}{da}\right) da. \qquad (37)$$

According to the NASGRO equation by Forman and Mettu (FormanMettu 1992)

$$\frac{da}{dN} = (C*F)^{-1} * \Delta K^{-m} * \frac{\left(1 - \frac{K_{max}}{K_C}\right)^q}{\left(1 - \frac{\Delta K_{th}}{\Delta K}\right)^p} = \qquad (38)$$

$$(C*F)^{-1} * \Delta K^{p-m} K_C^{-q} \frac{(K_C - K_{max})^q}{(\Delta K - \Delta K_{th})^p}.$$

Here, C represents a crack growth constant, F a crack velocity factor, $\Delta K$ a stress intensity factor range and $K_{max}$ a maximum stress intensity factor. Furthermore, m denotes Paris exponent and $\Delta K_{th}$ threshold of stress intensity factor range for crack propagation.

By applying ML to estimating the number of cycles, N, directly, one may avoid error magnification that otherwise could occur during the integration process, due to over- or under-fitting.

Figure 33:
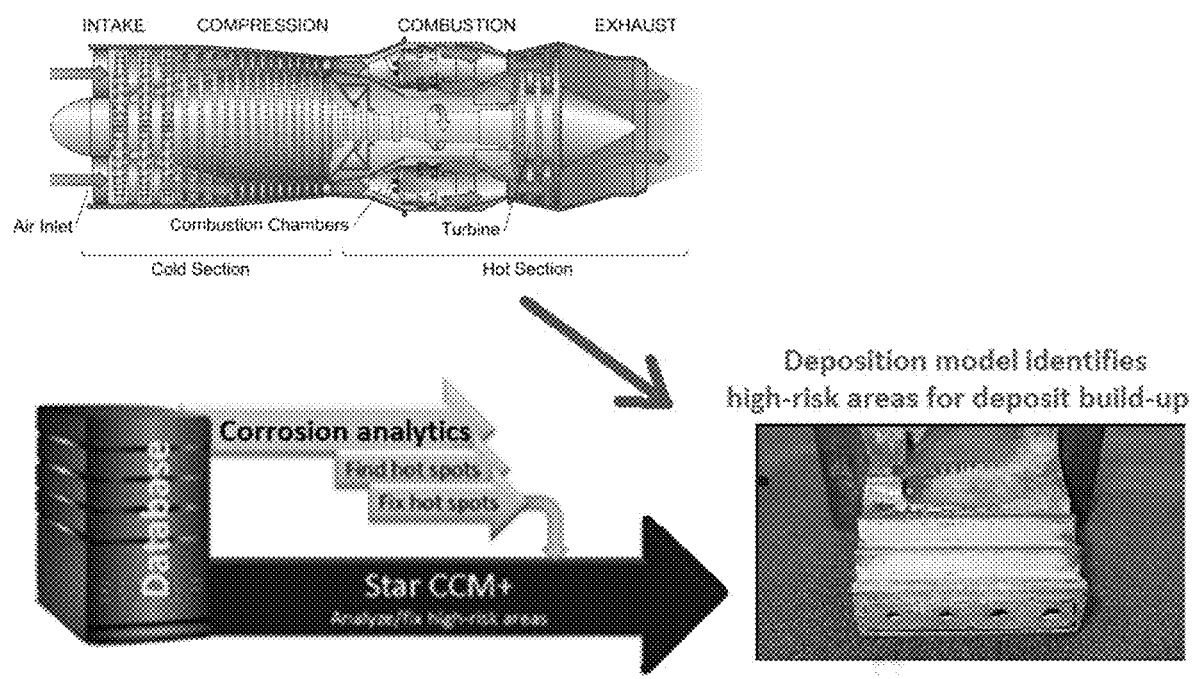
FIG. 33 presents corrosion analytics in context with the overall effort to identify high-risk areas for deposit build-up on actual components in gas turbines.

9 Example 4: Towards Corrosion Resistant Coatings—Analysis of CMAS and Calcium Sulfate Attacks 9.1 Overall Picture This invention can utilize literature materials data or experimental data to develop models or algorithms for machine learning (ML) that will detect data patterns and characteristic trends, learn from the accumulated data, and evolve distinguishing characteristics between calcium-magnesium-alumino-silicate attack (CMAS) and calcium sulfate (CaSO4) hot corrosion, with and without the influence of sea salt, in order to develop resistant coatings to CMAS and calcium sulfate hot corrosion. FIG. 33 presents corrosion data analytics in context with the overall effort to identify high-risk areas for deposit build-up in gas turbines.

We seek to link structure and chemistry to observed reaction mechanisms to accelerate materials design for corrosive environments.

The intent is to develop sophisticated physics-based prediction models from experimental data.

The deposition model of (KulkarniEPRI 2020) provides valuable information on where deposits are likely to take place inside a gas turbine. The deposition model incorporates the particulate characteristics and component design conditions to identify high risk areas for deposit buildup for actual components. The deposition model covers the cases of hot corrosion for land-based, air-borne or sea water applications of gas turbines. In sea water, sodium chloride or sodium sulfate tend to be prevalent, and the corrosion reactions may occur at lower temperature. But the deposition model still applies (with adjusted input values).

9.2 Essence of CMAS and Calcium Sulfate Corrosion Attacks

The CMAS attacks the ceramic (top coating) first, and then attacks the metal side. For CMAS, reaction with TBC is the only thing we consider. The calcium sulfate (CaSO4), on the other hand, soaks into the ceramics (top coating), and then attacks the bond coat surface and the base alloy (the super-alloy). For the calcium sulfate, there is less interaction with the TBC, but more with the base alloys.

9.3 Specifics of Interaction of CMAS with the Thermal Barrier Coating

CMAS consists a combination of $SiO_2$, CaO, Mg, $Al_2O_3$ and FeO. For information on relative concentration of these constituents between different types of CMAS simulated sand, engine deposits, average earth's crust, Saudi sand, airport runway sand, Mt. St. Helen's volcanic ash, Eyjafjallajokull volcanic ash, subbituminous fly ash or bituminous fly ash, refer to (LeviHutchinson 2012).

Figure 34:
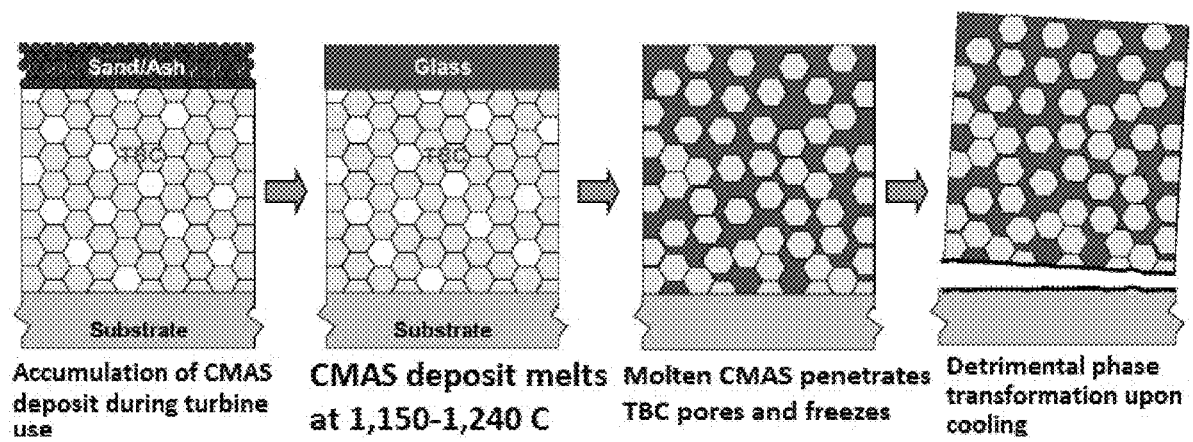
FIG. 34 presents the essential mechanism behind corrosion of the thermal barrier coating instigated by a CMAS hot corrosion attack.
Figure 35:
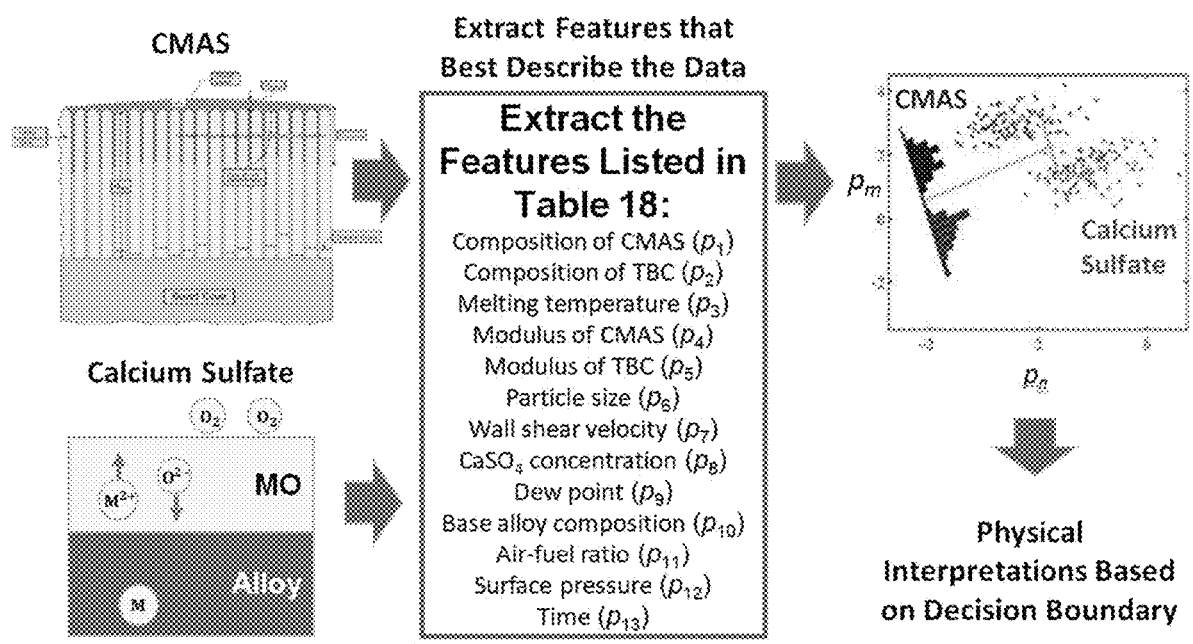
FIG. 35 shows how canonical correlation analysis can be applied to analysis of feature sets corresponding to CMAS and calcium sulfate hot corrosion attacks.

CMAS degradation is both thermochemical and thermomechanical to the thermal barrier coatings (TBCs), as shown in FIG. 34. Molten CMAS (1,150-1,240° C.) penetrates the TBC pores and freezes a given depth within the TBC. Above 1250° C., CMAS deposits can infiltrate and significantly dissolve YSZ top coatings via thermochemical interactions. Upon cooling, zirconia can reprecipitate with a spherical morphology and a composition that depended on the local melt chemistry. Upon cooling, the CMAS can destabilize the YSZ top coating through a detrimental phase transformation (t'→t→f+m).

Calcium oxide (CaO) is known to react with chromium contained in MCrAlY (M=Ni, Co) alloys and nickel-based superalloys to form a low-melting (1,100° C.) calcium chromate. The reactivity of gamma-NiAl and gamma-Ni-based NiCoCrAlY alloys with CaO at 1,100° C. produced multi-layer scales of $Al_2O_3$ and calcium aluminates (xCaO-yAl2O3). Increasing alloy chromium content only enhances corrosion severity. The reaction of two-phase beta-gamma MCrAlY alloys with CaO progressed according to two distinct mechanisms:

1. During the initial stage, formation of a liquid calcium chromate led to the rapid consumption of the Cr-rich gamma-phase. The extent of degradation was particularly important for a single-phase gamma-composition, and was significantly reduced by increasing the alloy beta fraction.
2. In the subsequent stage, a continuous $Al_2O_3$ layer was established at the base of the scale, which led to a much lower oxidation rate. Additions of $Al_2O_3$ or $SiO_2$ decreased the CaO reactivity due to the formation of aluminates or silicates.

Upon cooling, the glass and reaction product phases solidify and the void structure that is utilized to reduce thermal conductivity and provide the strain compliance is lost leading to TBC delamination, as shown in FIG. 34.

9.4 Specifics of Interaction of Calcium Sulfate with the Thermal Barrier Coating and Base Alloy Due to relatively short history, modeling of $CaSO_4$ is in part based on analogy with sodium sulfate ($Na_2SO_4$).

Early research has shown that $CaSO_4$ tends to attack yttria, destabilizing zirconia-based TBCs.

CoNiCrAlY in both as-sprayed and preoxidized condition suffered a significant damage by $CaSO_4$ deposits via a basic fluxing mechanism that yielded $CaCrO_4$ and $CaAl_2O_4$.

sulfate tend to be prevalent, and the corrosion reactions may occur at lower temperature. But the same feature list still applies (with adjusted input values).

TABLE 18

Unified feature list for analysis of CMAS and calcium sulfate hot corrosion, both covering attacks in air and sea water.

| I/O | Parameter | Note |
| --- | --- | --- |
| Inputs | Composition of CMAS | Applicable to CMAS attacks |
| | Composition of TBC | Applicable to CMAS and $CaSO_4$ attacks |
| | Melting/solidification temperature | Applicable to CMAS attacks |
| | Modulus of CMAS | Applicable to CMAS attacks |
| | Modulus of TBC | Applicable to CMAS attacks |
| | Particle size | Applicable to CMAS attacks |
| | Surface temperature | Applicable to CMAS attacks |
| | Wall shear velocity | Applicable to CMAS attacks |
| | $CaSO_4$ concentration | Applicable to $CaSO_4$ attacks |
| | Dew point | Applicable to $CaSO_4$ attacks |
| | Base alloy composition | Applicable to $CaSO_4$ attacks |
| | Air-fuel ratio | Applicable to $CaSO_4$ attacks |
| | Surface pressure | Applicable to $CaSO_4$ attacks |
| | Time | Applicable to CMAS and $CaSO_4$ attacks |
| Outputs | Chemical reactions | Applicable to CMAS attacks |
| | Particle temperature | Applicable to CMAS attacks |
| | Particle velocity | Applicable to CMAS attacks |
| | Coating modulus after infiltration | Applicable to CMAS attacks |
| | Deposit build-up rate | Applicable to CMAS attacks |
| | Weight change | Applicable to $CaSO_4$ attacks |
| | Metal loss | Applicable to $CaSO_4$ attacks |
| | Depth of attack | Applicable to $CaSO_4$ attacks |

9.7 Canonical Component Analysis for Deriving Distinguishing Characteristics Between CMAS and Calcium Sulfate Hot Corrosion Attacks In order to evolve distinguishing characteristics between CMAS and calcium sulfate hot corrosion, with or without

TABLE 17

Characterization of the reaction space for CMAS and calcium sulfate attacks, with and without sea salt. Siemens has a few sites where they have seen $CaSO_4$ attacks, and they have done the reaction studies for those super-alloys.

| Attack/Deposit | Environment | Reactions | Temperature |
| --- | --- | --- | --- |
| CMAS (Calcium-magnesium-alumino-silicate; $CaO-MgO-Al_2O_3-SiO_2$) | Natural/Air (without sea salt) | $CaSO_4 + 2H_2O = CaSO_4$ | Dehydration at 150° C. |
| | | $CaCO_3 = CaO + CO_2$ | ~800° C. |
| | | $CaSO_4 = CaSO_3 + 1/2 O_2$ | ~1200° C. |
| | | $CaSO_3 = CaO + SO_2$ | |
| | Reaction with TBC (7YSZ) | $CaO-MgO-Al2O3-SiO2-Y2O3-ZrO_2$ is the key system | |
| | Prototypical salt: $Na_2SO_4$ ($T_{melt} = 881°$ C.) | Fluxing process (Type I) | ~900° C. |
| | | Salt-component processes (Type II) | ~700° C. |
| Calcium Sulfate | Natural/Air | $CaSO_4 \cdot 2H_2O = CaO + SO_3 + 2 H_2O$ | ~1220° C. |
| Sodium sulfate | Natural/Air | $2 NaCl + SO_2 + O_2 = Na_2SO_4 + Cl_2$ | ~900° C. |

9.5 Overview of the Reaction Space

The reaction space for CMAS, calcium sulfate and sodium sulfate ($Na_2SO_4$) deposition is summarized in Table 17. We are including sodium sulfate for historic reference. Research into hot corrosion and its preventive measures in gas turbine engines has mostly focused on sodium sulfate since the early 1950s.

9.6 List of Features Jointly Characterizing CMAS and Calcium Sulfate Corrosion Attacks Table 18 summarizes a unified list of features characterizing CMAS and calcium sulfate corrosion attacks, both in air and sea water. In sea water, sodium chloride or sodium the influence of sea salt, in order to develop resistant coatings to CMAS and calcium sulfate hot corrosion, we apply canonical component analysis, as qualitatively shown in FIG. 35.

As an alternative to canonical component analysis, one also can conduct correlation between the input and output features, using regression analysis, as shown in (SteingrimssonJonesKisialiou 2018).

9.8 Joint Optimization

To accurately identify a (TBC, base alloy) combination that is likely both protect against a CMAS and calcium sulfate attack, assuming the CMAS protection is measured through deposit build-up rate, but the calcium sulfate protection through weight change, metal loss and depth of attack, we apply joint optimization.

We optimize a weighted objective function of the form $$\text{Objective} = w_1 \text{ deposit\_build\_up\_rate} + w_2 \text{ weight\_change} + w_3 \text{ metal\_loss} + w_4 \text{ depth\_of\_attack}. \tag{39}$$

Example 5: Joint Optimization of Material Strength and Ductility

For operating turbines or other energy conversion devices at higher temperature, and with improved efficiency, there is need for materials yielding good strength at higher temperature, without sacrificing ductility at room temperature. The design goals involve joint optimization:
  5. Achieving the required material strength at higher temperature.
  6. Improving room temperature ductility (decreasing the brittle-to-ductile transition below room temperature).
  7. Offering acceptable oxidation resistance.

In principle, there are two, primary routes for formulating such joint optimization problems:
  1. Through maximization of a joint objective function, one accounting both for strength and ductility.
  2. Through maximization of an objective function only capturing the strength, but where the ductility is accounted for in the constraints.

7.3 Specific Approach to Prediction of Employing Statistical Modeling—Prediction of Fatigue Life of Additively Manufactured Components 1. Statistical Modeling Compared and Contrasted to Physics-Based Modeling For certain applications, the selection of the prediction model may be based on a probabilistic, not physics-based, derivation. The assumption of a constant failure rate, i.e., of $1/\lambda$ representing the time to failure, results in an exponential function (a standard Weibull distribution).

At times, one may assume independence between events, and invoke the Central Limit Theorem of statistics. In case of alloy design, the parameters may tend to be inter-related, and hence, we may not be able to invoke the Central Limit Theorem. One may need to derive dependent distributions, based on the dependency relations established (per FIG. 18).

Figure 38:
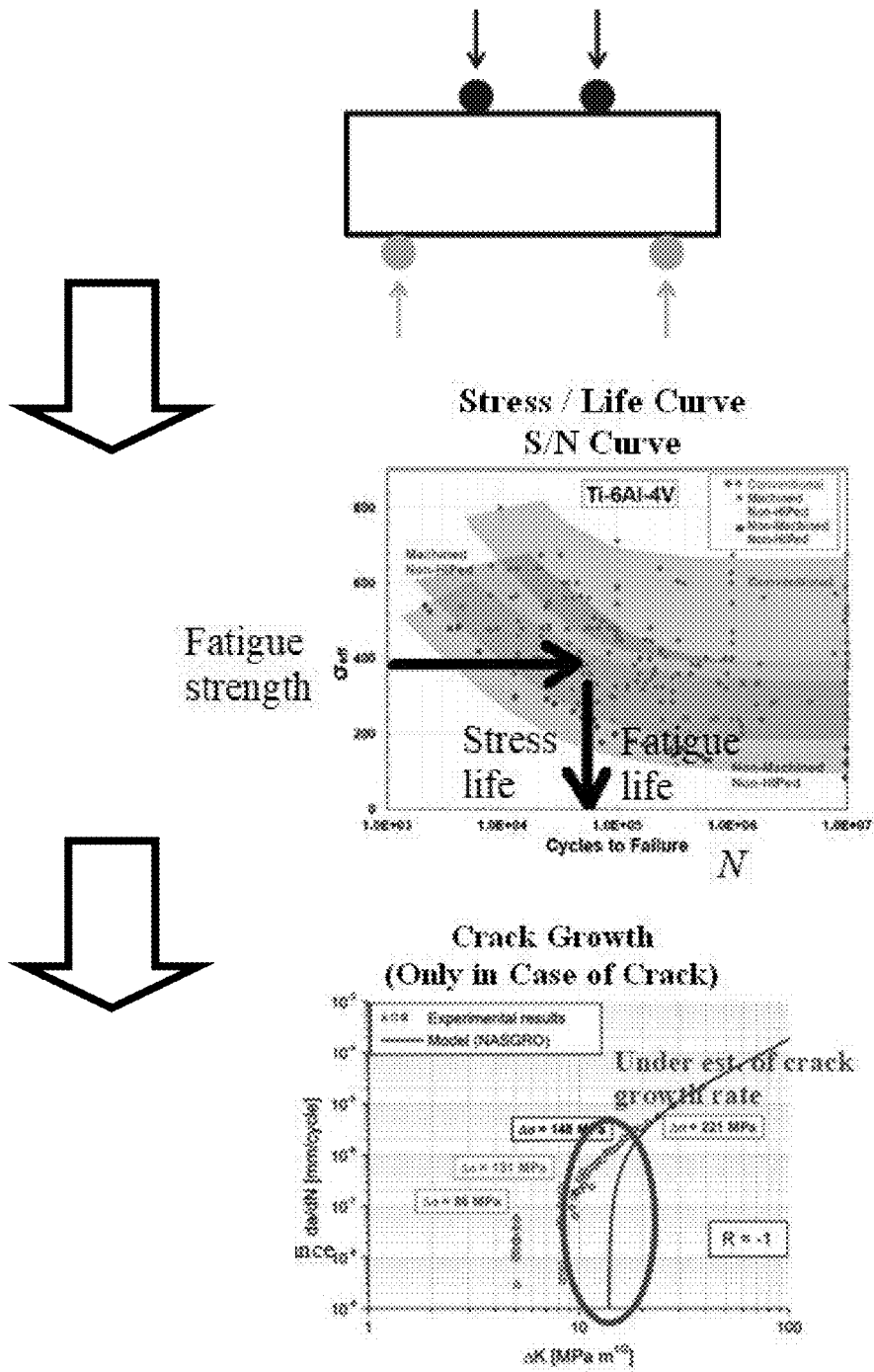
FIG. 38 outlines a classical approach for analyzing fatigue life. The top figure shows the stress applied (from 4-point testing). The middle figure shows the fatigue life obtained from the stress applied. The bottom figure shows the fatigue life remaining (curve fit to data). The classical NASGRO model can yield over- or under-estimation of the fatigue life, due to over- or under-fitting. This results in error magnification during integration. Machine learning may account for all the parameters affecting fatigue life of AM components, not only those modeled by the NASGRO equation, and hence yield more accurate results.

2. Statistical Fatigue Life Model for Analytical Representation of Stress/Life (S/N) Curves A commonly used analytical representation of S/N curves, like the ones presented in FIG. 38, is given by (ChernNandwana 2019), (HemphillYuanWang 2012):

$$N(\sigma) = c\sigma^{-d}. \tag{40}$$

Here, $\sigma$ represents the applied stress, $N(\sigma)$ is the expected cycles to failure at the stress a, and c and d are positive material parameters. Taking the logarithm of the S/N relation given by Eq. (39) yields (ChernNandwana 2019), (HemphillYuanWang 2012):

$$\log[N(\sigma)] = a + b*\log(\sigma), \tag{41}$$

where $a = \log(c)$ and $b = -d$. Eq. (40) describes the relationship between the mean-log of the fatigue life and the applied stress. In order to account for scattering observed in the fatigue-life experiments, a regression model is formulated by adding a random error term (ChernNandwana 2019), (HemphillYuanWang 2012):

$$\log[N_{ij}] = \mu_i(\sigma_{ij}) + \varepsilon_{ij} = a_i + b_i*\log(\sigma_{ij}) + \varepsilon_{ij} \tag{42}$$

Here, i indexes the process categories available, but j the data points available for each process category. $N_{ij}$ is the j-th data point under condition i collected at the stress $\sigma_{ij} \ldots \varepsilon_{ij}$ is a random error term, which is assumed to follow normal distribution with mean zero and standard deviation, $s_i$. $\mu_i(\sigma)$ is the mean (also the median) logarithm transformed fatigue life at stress, $\sigma$, under condition i. The collected fatigue life data is denoted by $\{N_{ij}, \sigma_{ij}, \delta_{ij}\}$, where $\delta$ is a runout indicator, defined as $\delta = 1$ for a failure observation and $\delta = 0$ for a runout. The likelihood function for the observed fatigue life data under condition i is then given by (ChernNandwana 2019), (HemphillYuanWang 2012):

$$L_i(a_i, b_i, s_i) = \prod_{j=1}^{m_i} \left[\phi\left(\frac{\log(N_{ij}) - a_i - b_i*\log(\sigma_{ij})}{s_i}\right)\right]^{\delta_{ij}} \times \left[1 - \Phi\left(\frac{\log(N_{ij}) - a_i - b_i*\log(\sigma_{ij})}{s_i}\right)\right]^{1-\delta_{ij}} \tag{43}$$

where $\phi(\cdot)$ and $\Phi(\cdot)$ represent the probability density function and the cumulative distribution function of the standardized normal distribution, respectively.

3. Augmentations of the Statistical Fatigue Life Model

The Statistical Fatigue Life Model can be augmented such as to include additional input parameters.

In case of N independent events, the probability of failure, P(fail), can be formulated using Poisson distribution:

$$P(\text{fail}) = \Pi_{i=1}^N P_i(\text{fail}) = \Pi_{i=1}^N f_i \exp(-c_i) = f_1 * f_2 * \ldots f_N * \exp(-\Sigma_{i=1}^N c_i). \tag{44}$$

With this in mind, it makes sense to model the augmented version of the Statistical Fatigue Life model (Eq. (39)) as $$N(\sigma, p_1, p_2, p_3, \ldots, p_N) = f_1(p_1, p_2, p_3, \ldots, p_N) \sigma^{-f_2(p_1, p_2, p_3, \ldots, p_N)}. \tag{45}$$

Here, $p_1, p_2, p_3, \ldots, p_N$ model the input parameters impacting the fatigue life of AM metallic components. For a specific parameter selection, refer to Table 1. We are assuming that multiple effects cause failure and that these effects are close to independent. The function $f_1(\cdot)$ models a prior knowledge and the function $f_2(\cdot)$ conditional probabilities. For dependent events, one can apply a Bayesian model, with the same definition of $f_1(\cdot)$ and $f_2(\cdot)$.

In case of independent events, it makes sense to apply the direct linear regression to assess $f_1(\cdot)$ and $f_2(\cdot)$. But in case of coupled failure modes, $f_1(\cdot)$ and $f_2(\cdot)$ may consist of complex Bayesian functions. We may not know these functions, and one may be able to apply regression analysis, but these functions still may be hard to derive. So this is where ML comes in. One can apply neural networks or support vector machines to effectively deduce these functions from the data. Even if 100-200 parameters impact the fatigue life of AM metallic components, this is still a relatively small set by the standards of ML.

The model of Eq. (44) should be able to predict the time to failure with better accuracy, for reasons similar to the quadratic regression model in FIG. 36 providing accuracy superior to that of the linear regression. The main objective is to quantify the accuracy and reduce the error bars (improve the accuracy of the fatigue prediction).

One of the primary advantages of the model in Eq. (44) involves the ability to (a) determine the top factors that contribute to fatigue life, and (b) provide feedback, through sensitivity analysis. By estimating $$\frac{\partial N(\sigma, p_1, p_2, p_3, \ldots, p_N)}{\partial p_i}, i = 1, 2, 3, \ldots, N, \qquad (46)$$

one can assess the contribution of the input parameter, i, to the fatigue life. Such feedback may yield significant, tangible benefits. The dominant factors contributing to the reliability may involve something in manufacturing. Maybe it is something involving the material properties. Maybe the smaller gain size will improve the fatigue life. Our model may be able to quantify for how long to expose the laser, at which temperature, with which grain size, and translate into fatigue life. Such information can be of great value, and may lead to iterative refinements. The fatigue-prediction toolset can advise on, say, how to change a given material property. Once the property has been changed, and new data generated, the data can be fed back into the model and the impact assessed.

It is our understanding that small variations in the atomic % of Sulphur or Carbon can have significant impacts on fatigue life of the stainless steel.

4. Review of Advantages of Machine Learning for Prediction of Fatigue Life of AM Components ML can help address (avoid) inaccuracies in fitting traditional models to real-world fatigue data. Traditional models are prone to under- or over-fitting, and can lead to error magnification during integration.

ML can help in terms of accounting for all the sources that can impact fatigue life of AM components. As noted above, it has been reported that over 100 different process parameters can affect the fatigue life of AM components (Chern-Nandwana 2019). Traditionally, parametric models have been designed to account for key sources, but not for all the sources.

Existing software tools cannot predict the material properties or account for AM.

Given the Statistical Fatigue Life model, or its augmented version, one can play with the input parameters such as to maximize fatigue life (optimize for fatigue life), and provide feedback on manufacturing process. The invention can provide feedback on the impact that variations in input parameters have on fatigue life.

7.4 Prediction for an Intelligent AM System

Figure 39:
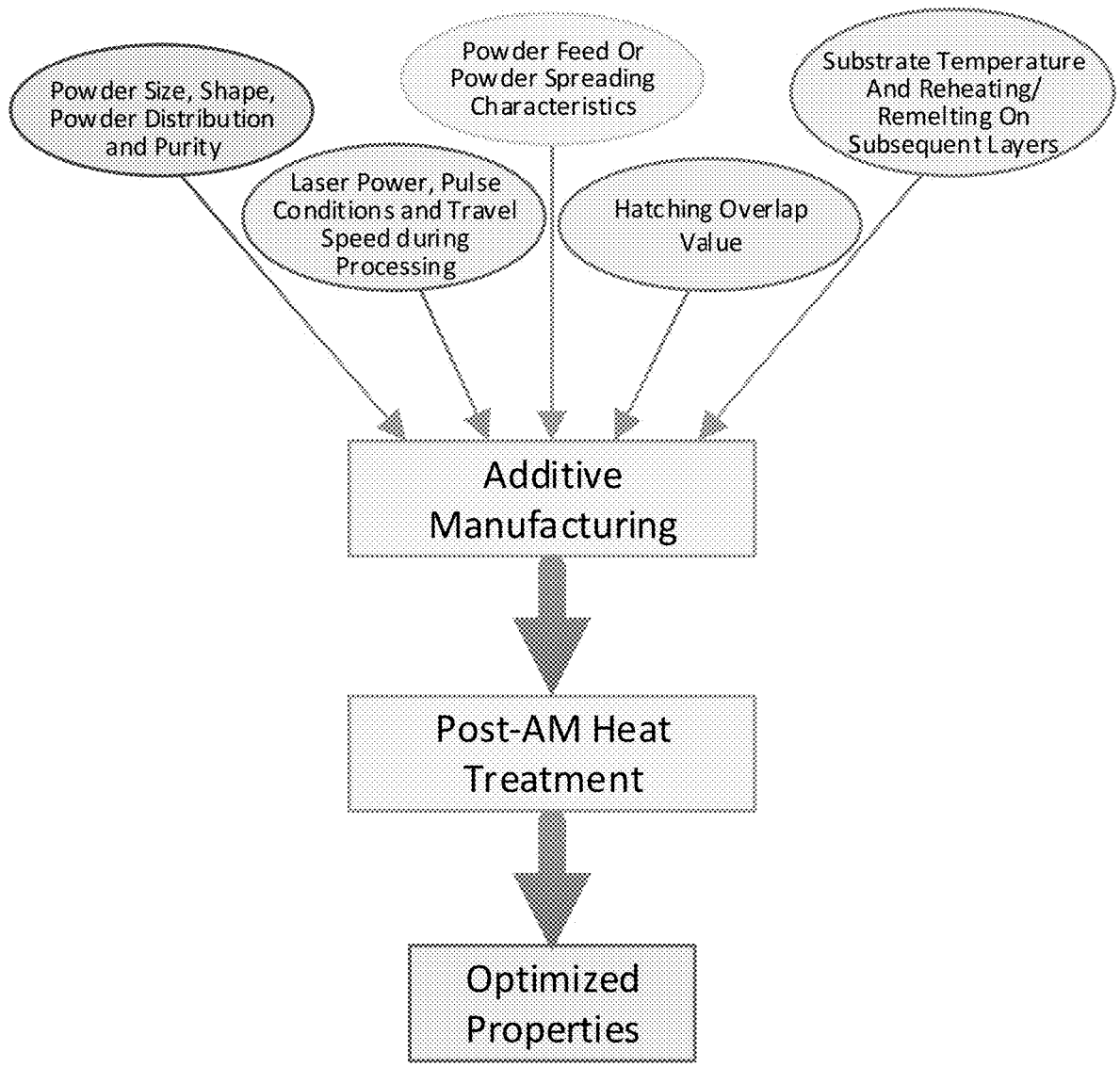
FIG. 39 presents a high-level overview over optimization of an AM process for HEAs.

Key steps will include systematically changing the key parameters (the laser power and travel speed during deposition, powder feed rate and increment, number of laser tracks for each patch and overlap value, repeat times and laser power during re-melting, the powder size, powder shape, powder distribution and purity), as shown in FIG. 39.

Factors that make AM, and in particular laser powder bed fusion AM, such a challenging manufacturing process are:

1. The smallness of the laser processing volume and rapid melt time when compared to the final part size and build time respectively and the associated process variabilities that result from them.
2. The intrinsic variability of all the powder bed physical (mass, heat capacity, thermal conductivity, emissivity, reflectivity) and chemical (composition, oxidation state, wetting angle) properties that compound to the above-mentioned process variabilities.
3. The large power densities required to process the powder bed and the associated large heating rates and thermal gradients, which when combined with the above-mentioned variability makes it difficult to control the microstructure of the processed volume.
4. The chaotic nature of the AM process that results from combining the small spatial and temporal scales described above with the high energy densities required for melting the powder, which makes it difficult to reliably predict the process trajectory in the multi-parameter process space before the build process starts and virtually impossible to control it in real time.
5. The large number of process parameters (in some cases over 100) that can affect the outcome of the AM process and make it almost impossible to model with physics-based models.
6. The non-symmetric deposition of the processing energy that results from rastering a single laser beam over the powder bed which leads to non-uniform heating/cooling rates, thermal gradients, residual stresses and part defects and distortion.

Most of these challenges can be alleviated by better controlling and distributing the laser energy at and around the melt pool area and/or the processing part surface area combined with real-time monitoring of the same area or beyond and by intelligently linking the laser energy control parameters with the process monitoring sensors to learn and adapt to the continuously evolving environment. Distributing the process energy intelligently at and around the melt pool would help reduce the process variability, the powder bed physical property variability, the heating/cooling rates and the thermal gradients. For example, it might be desirable to pre-heat the powder ahead of the melt-pool without melting it, to reduce the heating rates and thermal gradients later during melting. Doing so might allow processing the powder faster and reducing the build time while at the same time reducing evaporative recoils, ejecta and denudation effects (which induce defects in the final part). Monitoring the temperature profile around the melt-pool area could be used to adjust the distributed laser energy control parameters (power levels and distribution) in real time in a system where the temperature profile is directly linked to the heating source control parameters via an AI processor. Similar improvements could be achieved by intelligently distributing the laser processing energy over the entire part surface while monitoring the temperature evolution over the same area.

The intelligent AM system links the actuators controlling the laser energy distribution over the powder bed with the sensors that monitor the temperature distribution and/or other relevant process parameters over the powder bed using a real-time AI controller.

Figure 40:
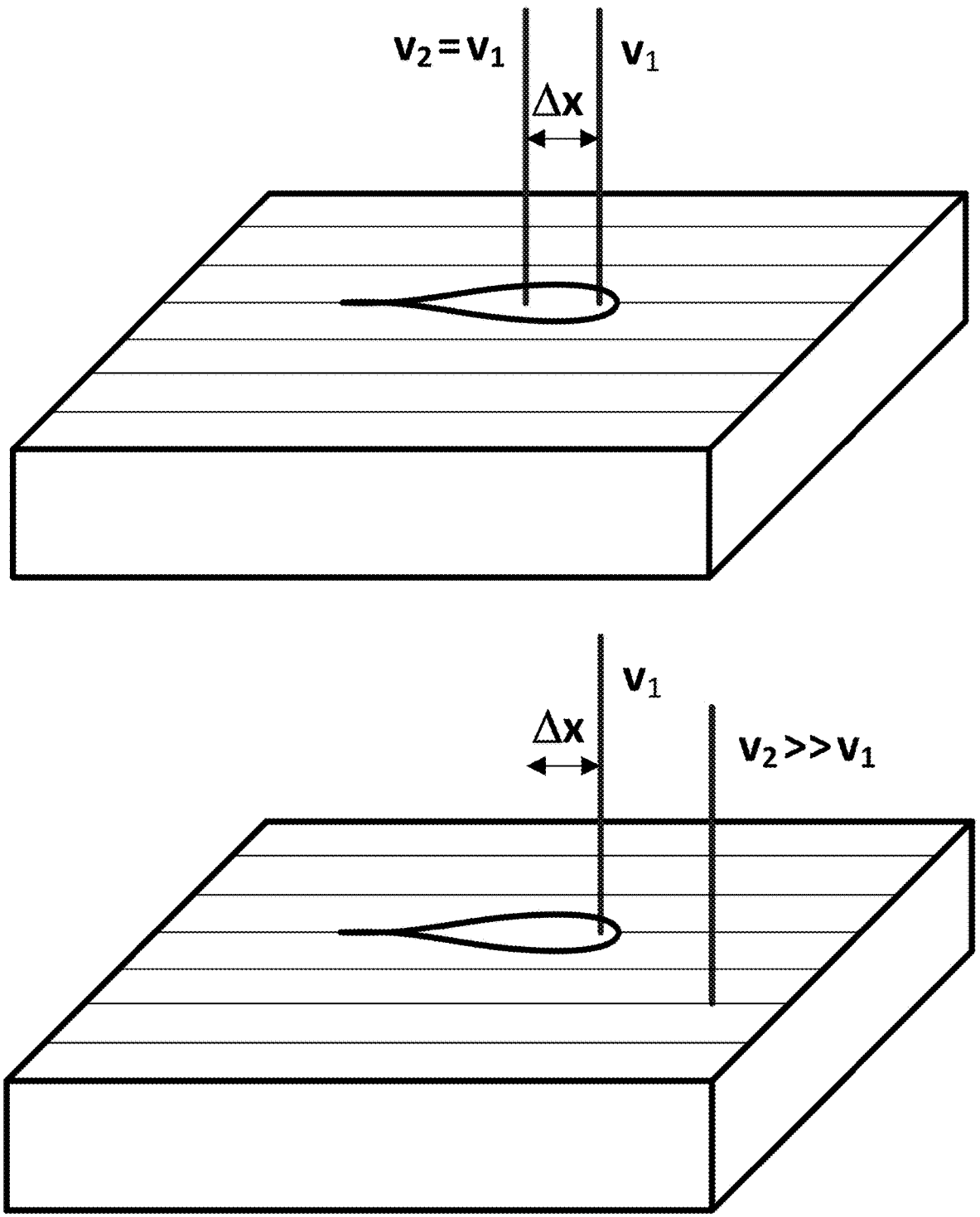
FIG. 40 (top) shows an offset strategy, using two beams in a defined offset at the same speed.

Specifically, the intelligent AM system employs a multi-beam strategy to customize the melt pool temperature and the energy distribution over the powder bed, as shown in FIG. 40.

7.5 Other Applications—Prediction of Properties Beyond Alloy Compositions—Composites Our approach entails establishing correspondence with existing research work for HEAs. The data analytics and optimization techniques would be extended to next-generation multi-functional composites.

Figure 3:
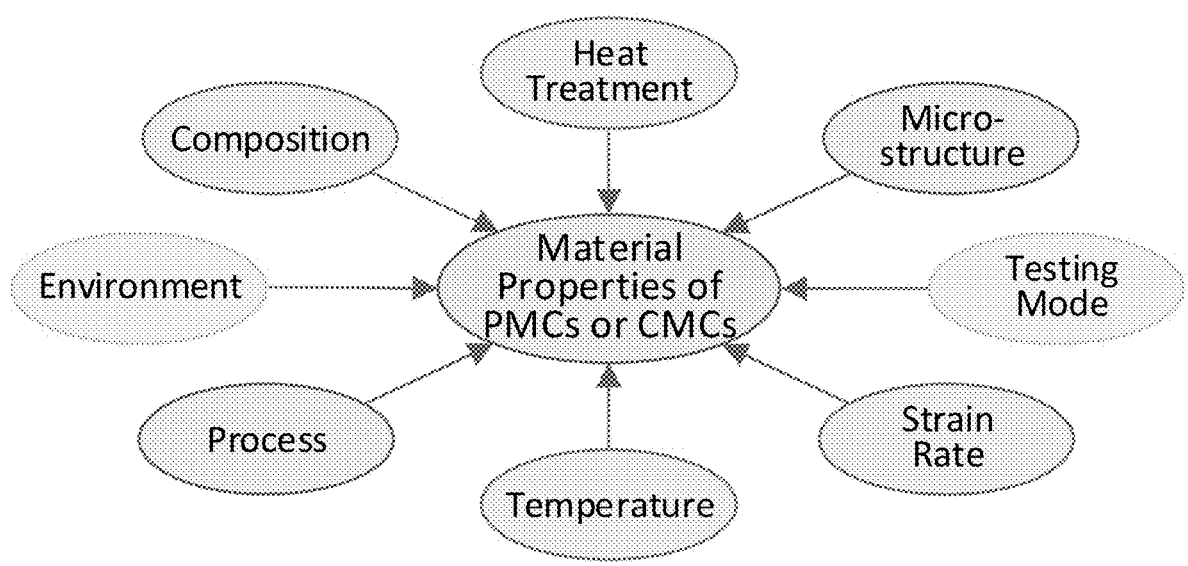
FIG. 3 presents a figure similar to FIG. 1 of the primary factors impacting the material properties of matrix composites.
Figure 4:
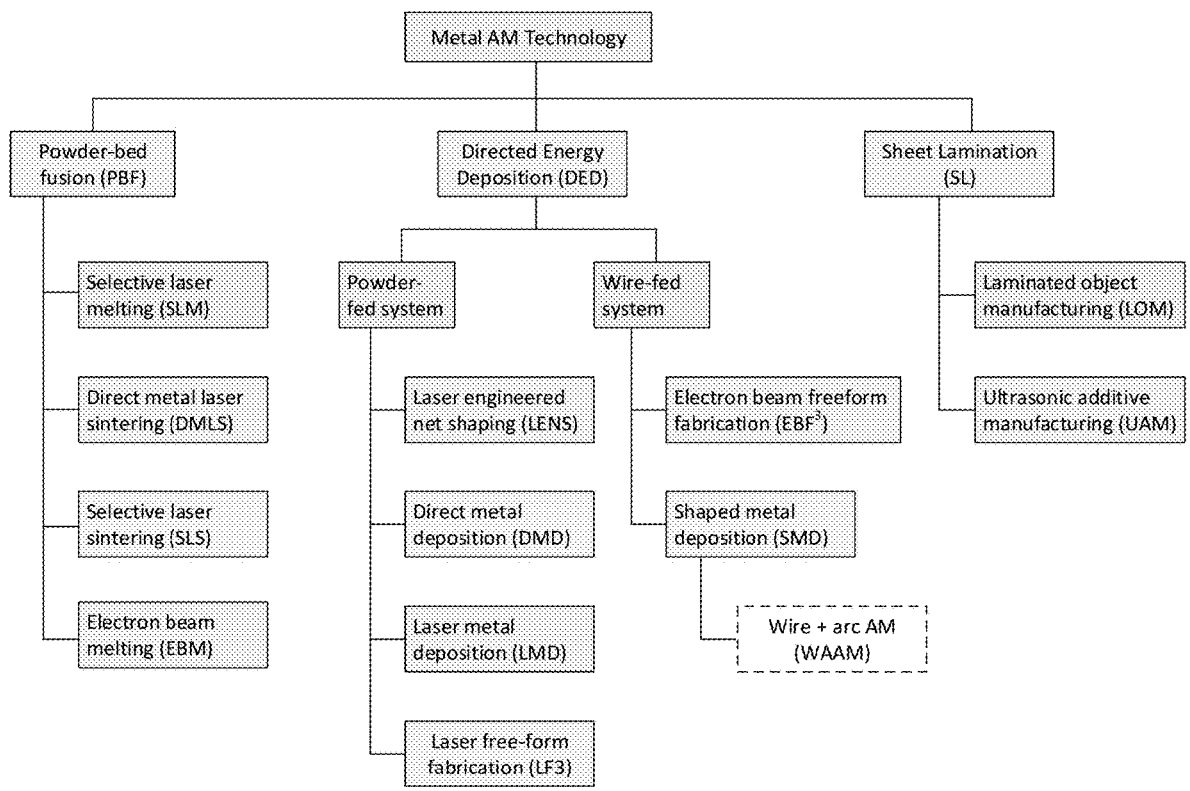
FIG. 4 presents an overview over metal AM technologies.

FIG. 3 presents the primary sources impacting the material properties of HEAs to matrix composites.

FIG. 13 shows how prediction of material properties of HEAs can be extended to matrix composites.

One can formulate models capturing the underlying physical dependencies, similar can FIG. 18.

Similar to the case of alloy design, one can start with simple models and build up from there (look to capture the underlying physics and correspondingly introduce non-linearities in the models, for improved accuracy).

In further correspondence with the case of alloy design, one can select an analysis technique, suitable for the application at hand and for the data available.

8. Verification, Validation and Reporting

8.1 Verifying Predictive Capability of ML Algorithms

Verification of the predictive capability of the ML algorithms is primarily based on comparison with experimental results, as shown in FIG. 37. One can print materials in relevant geometries from down-selected compositions predicted by the ML algorithm, such as materials predicted to perform well in elevated temperature creep environments. Comparison of predicted material properties to the observed properties will enable assessment of the predictive capabilities of the machine learning algorithms.

8.2 Analysis of Outliers—Verification Addressing Implications of Incomplete Data Sets Table 14 and Table 15 illustrate how outliers, resulting from a limited data set (FIG. 36) can be analyzed.

8.3 Approach to Rapid Screening

For rapid screening (high throughput experiments), one may emphasize properties that do not depend heavily on the microstructure.

8.4 Uncertainty Quantification

We assume the uncertainty quantification is consistent with similar activities within NIST or CALPHAD.

NIST has some interesting projects for AI/ML data extraction and uncertainty prediction, such as AI self-quality assurance using learning curves in feedback loops and CALPHAD Uncertainty (NistAiUncertainty 2019).

8.5 Reporting

The reporting mechanism is integrated into the user interface listed above.

In one embodiment of the invention, reporting of results predicted is based on the traditional Model-View-Controller paradigm (Steingrimsson 2017).

9. System Integration (Case of Embedded Implementation)

9.1 General Considerations

The primary use case for an embedded implementation involves a plugin to or web service for ICME or Product Lifecycle Management tools, such as Thermo-Calc or Siemens STAR CCM+. Thermo-Calc, which was created using the CALPHAD methodology, comes with a diffusion module, called DICTRA. DICTRA is an add-on package for accurate simulation of diffusion controlled reactions in multi-component alloy systems. Thermo-Calc also comes with a SDK and a publicly available Thermo-Calc Application Programming Interface (TC-API), consisting of a library of C functions.

An alternative use case for an embedded implementation involves a plugin or add-on to, or even web service for, toolboxes (or libraries) for machine learning, artificial intelligence or data analytics, including the TensorFlow package (TensorFlow 2020) or scikit-learn (SciKit-Learn 2020) The physics-based models may be incorporated as add-ons to open-source, off-the-shelf toolboxes (libraries) for machine learning, artificial intelligence or data analytics, to provide physical insight as unexplored sections of the composition space are navigated.

9.2 Specific Example: Prediction of Fatigue Life of Additively Manufactured Components

9.1.1.1 Input

The input consists of finite-element data files from tools, such as Abaqus, ANSYS, NX Nastran and Altair OptiStruct.

9.1.1.2 Desired Output

The toolset is expected to calculate (estimate) realistic fatigue lives, accounting for AM.

9.1.1.3 API to Abaqus

Abaqus returns output database (.odb) files, which are binary files, but can be imported into our plugin, and decoded, using the Abaqus C++ API (Abaqus 2019).

9.1.1.4 API to ANSYS

ANSYS returns results (.rst) files, which are also binary files, and which can be imported into our plugin, using source code, such as available through ParaView or OpenFOAM (ParaView 2019), (OpenFOAM 2019).

9.1.1.5 API to NX Nastran and Through FEmap

FEmap is an advanced engineering simulation application for creating, editing and importing/re-using mesh-centric FE analysis models of complex products or systems. You can combine FEmap with a wide variety of CAD systems and finite-element solvers, including NX Nastran. The FEmap API is an OLC/COM based programming interface that supports object oriented programming. There are a number of codes that can call FEmap through the API (Visual Basic, Excel, Word, Access, C or C++) (PredictiveEngineering 2019).

9.1.1.6 Case of Altair OptiStruct

OptiStruct in HyperWorks supports scripts for reading in .fem files (AltairHyperWorks 2019).

10. How to Make the Invention

10.1 User Interface

In case of a prediction engine employing statistical modeling, such as for predicting the fatigue life of additively manufactured components, the preferred embodiment of the invention assumes the design of an efficient user interface, one capable of effectively guiding the user through (effectively helping the user specify) the multiple parameters impacting the fatigue life of additively manufactured components.

10.2 Data Base System

Using matlab .dat files or .xlsx or .csv files from Excel available, one can populate a test SQL data base with material records resembling the ones from (GorsseNguyenSenkovMiracle 2018). In one embodiment of the invention, Ref. (GorsseNguyenSenkovMiracle 2018) may provide a good starting point for a classification scheme:

Universe→Family→Class→Member→Attributes→Material Records.

The structure of the data in (GorsseNguyenSenkovMiracle 2018) seems to map well to relational databases.

In one embodiment of the invention, the feature extraction may resemble the Citrination platform for materials science data (LingAntonoBajaj 2018), (O'MaraMeredigMichel 2016). The Citrination platform automatically parses chemical formulas and alloy compositions, calculating over ninety different features based on the elemental properties (e.g., ionization energy, melting temperature and the number of valence electrons).

10.3 Prediction Logic

The prediction logic receives primitives from the prediction engine and passes to the reporting and validation module. The primitives include the quantity predicted, such as the feature list.

10.4 Prediction Engine

In one embodiment of the invention, the procedure for constructing the prediction engine may consist of the following steps:

1. One can start out by populating a sample SQL database with pertinent materials data, such as from (ChenWangSeifi Lewandowski 2018). (HemphillYuanWang 2012) (TangYuanTsaiYeh 2015), (Thurston GludovatzHohenwater 2017) (ShuklaWangCottonMishra 2018) (SeifiLiYongLiaw Lewandrowski 2015) (LiuKomarasamyGwalani 2019) or (JiaoSimKomarasamyMishra 2018).

2. One can normalize the data according to (1) and derive features in accordance with Table 7.

3. One can train the prediction model on pertinent materials data, such as from (((ChenWangSeifi Lewandowski 2018) (HemphillYuanWang 2012), (TangYuanTsaiYeh 2015), (Thurston GludovatzHohenwater 2017). (ShuklaWangCottonMishra 2018), (SeifiLiYongLiaw Lewandrowski 2015) (LiuKomarasamyGwalani 2019) and (JiaoSimKomarasamyMishra 2018)), and expand from there.

1. "Forward" prediction can be based on approaches such as outlined in FIG. 13 and FIG. 14.

2. "Inverse" prediction can be based on approaches, such as outlined in FIG. 15-FIG. 17.

10.5 Verification, Validation and Reporting

One can report verification and validation results in the form of scatter plots and error histograms similar to (Ling AntonoBajaj 2018) and (AgrawalDeshpande 2014).

11. How to Use the Invention

1. For Accelerating the Development of New Materials (Alloys or Composites)

The machine learning prediction framework is presented as a dual-use technology, intended both for military and civilian use. Direct dual use applications are expected to include a wide range of commercial applications, e.g., within the aerospace, marine, automotive, and oil and gas industries.

Tools for accelerating the new material discovery and optimizing AM processes for HEAs may benefit DoD Warfare Centers and Production Facilities. Dual-use applications may include aircrafts, land vehicles, ships, submarines and materials processing entities.

In case of an embedded implementation of the prediction engine, host applications used by alloy designers may include ICME tools, such as Thermo-Calc, DICTRA or the Pandat Software from CompuTherm, CFD tools, or tools for crack growth analysis (NASGRO, FE-SAFE, nCode DesignLife, AFGROW).

2. For Design of RHEAs for Use in Energy Conversion or Propelling Systems with Increased Conversion Efficiency The invention addresses development of useful inverse design representations, and advanced physics-based metallurgical models, enabling the identification of HEAs suitable for energy conversion devices, such as for compressor blades of land-based gas turbines operating with ultrahigh efficiency.

The invention can be used for design of refractory HEAs for application in land-based or air-borne gas turbines, or for application in propeller systems, such as used by the Navy, Air Force or the Army, operating with superior conversion efficiency, compared to conventional designs.

Stage one turbine blades are currently cast from nickel-base (Ni-base) superalloys, and due to material-property limitations, the combustor firing temperatures are capped at 1,450° C., which correlates to a carbon conversion efficiency of 62%. In order to achieve CCE in excess of 65%, a 300° C. increase in the combustor firing temperature is required. In materials terms, this requirement places a demand on stage one blade alloys to increase material capability by 200° C. (cooling and coating is expected to account for 100° C. difference).

Figure 8:
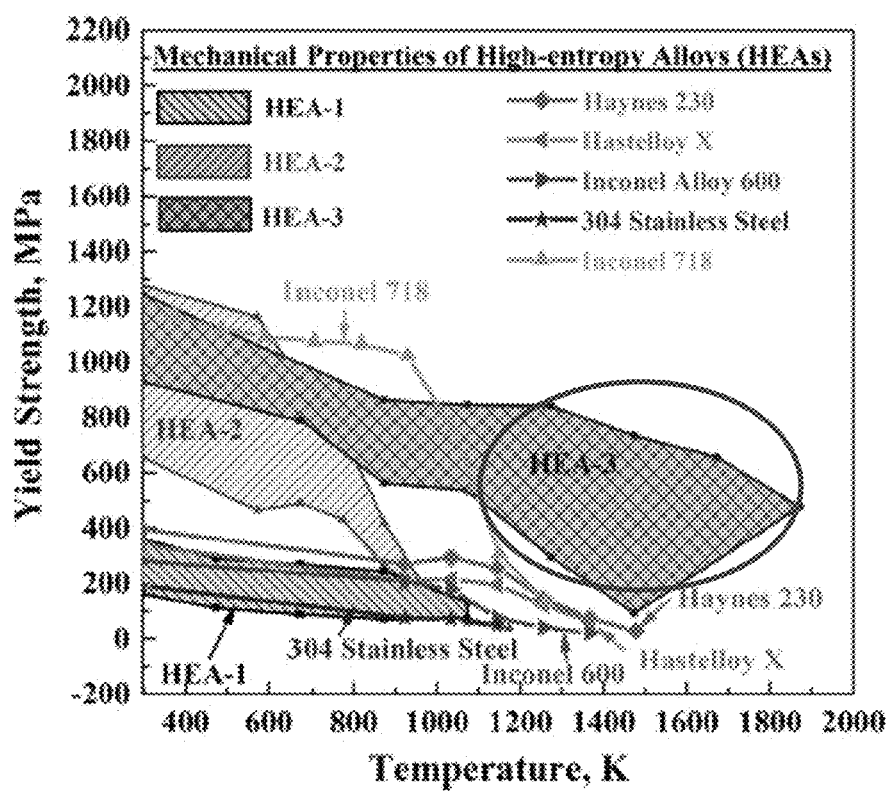
FIG. 8 illustrates that refractory metals in category HEA-3, yield much superior yield strength at high temperature, compared to alloys conventionally used in turbine blades.

3. For Design of RHEAs for Use in Energy Conversion or Propelling Systems Resulting in Reduced Cost of Manufacturing The invention helps advance the manufacture of new energy materials leading to improved performance and to lower manufacturing cost. The cost reduction can be achieved in part by redesigning the turbine blades such as to take advantage of the superior yield strength of the RHEAs, per FIG. 8, for the purpose of reducing the mass. Additional cost reductions are expected for air-borne turbines, where lighter turbine blades contribute to lighter vessels, and improved fuel economy.

Further, according to Siemens Energy, the high temperature materials capability of HEAs, combined with AM processing, enables a 30-50% reduction in product deployment time, leading to earlier realization of higher engine efficiency improvements.

4. For Design of RHEAs for Use in Automotive Applications

The invention can be used to design and develop advanced, lightweight materials for use in advanced internal combustion engines or emission systems. These will require structural materials, to withstand environments that exhibit temperatures (and pressures) well above conventional technologies. To successfully implement such advanced vehicle technologies, materials are required that can maintain their original material properties over a vehicle's lifespan.

ML and AM methods to design and fabricate lightweight HEAs for motor vehicle fuel efficiency applications. The AM and ML techniques have an enormous potential to produce lightweight materials that have superior corrosion and fatigue resistance as compared to conventional alloys. Furthermore, the combined use of the AI and ML techniques have the potential to reduce product development times from 15 to within ~5 years. This potential can be made possible in part by taking advantage of the physics-based metallurgical predictions that are inherent in the models.

5. For Developing Coatings Protecting Against Corrosion Attacks, Esp. CMAS or Calcium Sulfate, in Air or Sea Water The invention can be used in conjunction with applications for Product Lifecycle Management, such as Siemens STAR CCM+, to develop coatings resistant of CMAS or calcium sulfate corrosion attacks.

6. For Predicting Properties (Performance) of Additively Manufactured Parts

The invention is capable of optimizing the process parameters for additively manufactured components to achieve enhanced performance, including enhanced fatigue performance, such as for aircraft components.

7. For Estimating the Fatigue Life of Additively Manufactured Components

The invention can be used to estimate the fatigue life of an AM component, such as from a rotor of an aircraft (or any aircraft). One can use the invention to predict the stress/life curves for components of interest. From estimates of the fatigue life of a given component of interest, one can look to estimate service life of an entire subsystem or even of an entire aircraft.

8. For Deriving Optimal AM Processes

The invention (software application) can also accelerate and optimize the process of additively manufacturing alloys, such as high-entropy alloys. In terms of the fabrication of the high-entropy alloys, the invention can help optimize the selection of the laser power and travel speed during deposition, the powder distribution, shape, feed rate and increment, the number of laser tracks for each patch and overlap value, as well as the repeat times and laser power during re-melting.

The invention can help reliably predict the optimal trajectory in the multidimensional process parameter space due to the inherent spatiotemporal variability in the process parameter and the chaotic nature of the AM process. Despite the continued progress in AM technologies, AM parts still require several trial and error runs with post-processing treatments and machining to optimize the build, reduce defects and residual stresses, and meet tolerances. AM still lacks a stable process that can produce consistent, defect-free parts on a first time basis due to our inability to reliably predict the optimal trajectory.

9. For Intelligent AM Systems

Machine learning or AI can help with better distributing, monitoring, and controlling the processing energy in a laser metal powder bed fusion AM systems, for purposes of real-time process monitoring and control towards producing high-quality, defect-free AM parts with build periods comparable to or shorter than present ones. Using an AI controller (ML, deep neural network or neuromorphic processor), one can monitor the temperature distribution and/or other relevant process parameters over the powder bed.

10. As a Plugin to ICME Tools

In one embodiment of the invention, the prediction engine can be employed as a plugin to ICME tools, such as Thermo-Calc.

11. As a Plugin to Tools for Crack Growth Analysis

In another embodiment of the invention, the prediction engine can be employed as a plugin to tools for crack growth analysis, such as NASGRO, FE-SAFE, nCode DesignLife or AFGROW.

12. As a Plugin to Toolboxes (Libraries) for Machine Learning, Artificial Intelligence or Data Analytics As noted above, the physics-based models may be incorporated as add-ons to open-source, off-the-shelf toolboxes (libraries) for machine learning, artificial intelligence or data analytics, to provide physical insight as unexplored sections of the composition space are navigated.

13. As a Plugin or Web Service for Tools for Product Lifecycle Management

The prediction engine can be deployed as a plugin or web service for tools for Product Lifecycle Management, such as Siemens STAR CCM+.

14. For Design of CMCs or PMCs for High-Temperature Aerospace Applications

There is an ever-changing, constant need for designing novel composite materials for aerospace applications that offer a broader gamut of multi-functionality (sensing, electrical and thermal properties, desired interface characteristics, adhesion, energy storage/harvesting, low density, etc.) and structural stability (mechanical behavior, stiffness or compliance, fracture toughness, high temperature stability, minimal physical aging, etc.) with an eventual goal of minimizing costs and maximizing operational performance and efficiency. Experimentally, this design space is often explored via building upon previous reported literature towards synthesizing and characterizing state-of-the-art composite materials for various applications. Hence, there is opportunity to formalize modeling methods and data analytics, machine learning or artificial intelligence frameworks to investigate and understand structure-property-performance relationships in multi-functional PMCs or CMCs to (a) complement experimental efforts towards better appreciation of molecular origins of structure-property-performance relationships; and (b) facilitate accelerated materials design for next-generation multi-functional composites, geared towards aerospace applications.

In the gas turbine industry, CMCs are particular attractive, since they have the potential to replace nickel based superalloys in various hot section components.

12. Further Examples of the Invention

Thus, it will be appreciated by those skilled in the art that the present invention is not restricted to the particular preferred embodiments described with reference to the drawings, and that variations may be made therein without departing from the scope of the invention.

The invention claimed is:

1. An apparatus for predictive analytics, an apparatus that employs a prediction module, for the purpose of efficiently searching composition space of alloys or composites of interest, and hence for accelerating design or manufacturing of alloys or composites with desired material characteristics, an apparatus comprising of
   a database importing module, for ingesting materials or manufacturing data,
   an optional data base abstraction module, also referred to as prediction logic, for abstracting the interface between the prediction module and the database,
   an optional preprocessing module, for unified comparison of materials or manufacturing data across data sets,
   an optional feature selection module, for extracting features that best describe the material or manufacturing data of interest,
   a prediction module, also referred to as a prediction engine, for predicting material properties or manufacturing parameters of interest, along with a corresponding composition or composition range, given the materials or manufacturing data ingested, where the prediction engine employs a prediction technique, where the prediction engine combines physics-based models, or analytical models, specific to the alloys or composites of interest, with traditional black-box prediction models, for improved prediction accuracy, and where the prediction technique employed can involve regression analysis, with relatively few unknown model parameters, when limited data is available, but a machine learning predictor, with relatively many unknown model parameters, when sufficiently large data set is available, where the prediction technique is selected such that at least one data point is available for each unknown prediction model parameter, and
   an optional reporting and verification module, for reporting, evaluating or verifying the materials properties or manufacturing parameters estimated,
an apparatus presented either in the form of an integrated or an embedded application.

2. An apparatus according to claim 1, where the data importing module employs an Export, Transform and Load operation for importing data from a source into the destination prediction database logic, when the destination prediction database logic system represents the data differently from the source.

3. An apparatus according to claim 1, where the preprocessing module applies normalization for standardizing the input data ingested, for unified comparison, and where the standardization can involve division of endurance limit with tensile strength, in case of prediction of fatigue behavior of the alloys or composites of interest.

4. An apparatus according to claim 1, where the feature selection module utilizes features related to composition or micro-structure of the alloys or composite of interest, process, heat treatment, temperature, environment, testing mode or loading rate.

5. An apparatus according to claim 1, where the prediction engine is capable of accommodating models capturing physical dependencies, referred to as physics-based models, as a priori information, and correspondingly constructing dependencies within the prediction model, for purpose of expediting training of the prediction model or improving prediction accuracy.

6. An apparatus according to claim 5, where the physics-based models employ thermodynamics, first principle, empirical rules, mesoscale models, or in case of prediction of fatigue life, models for dislocation dynamics or slip band information.

7. An apparatus according to claim 1, where the prediction engine consists of optional "forward" prediction along with optional "inverse" prediction, where the "forward" prediction is responsible for predicting the material properties or manufacturing parameters of interest from source characteristics, where the "inverse" prediction is responsible for inferring source characteristics, in particular alloy composition, from source characteristics from material properties desired, and where the source characteristics can consist of composition, microstructure, process, heat treatment, temperature, environment, testing mode or loading rate.

8. An apparatus according to claim 1, where the feature selection module employs canonical component analysis or regression, for purpose of selecting features capable of distinguishing between calcium-magnesium-alumino-silicate and calcium sulfate hot corrosion attacks, in air or sea water, in order to develop coatings resistant to calcium-magnesium-alumino-silicate and calcium sulfate hot corrosion.

9. An apparatus according to claim 1, where the prediction engine utilizes a parametrized model, referred to as augmented Statistical Fatigue Life model, a model capable of accounting for multiple sources impacting fatigue life of additively manufactured components, for purpose of accurately predicting the fatigue life.

10. An apparatus according to claim 1, where the prediction engine supports inverse design representations.

11. An apparatus according to claim 1, where the prediction engine can employ custom kernel functions consistent with underlying physics, for the purpose of attaining tighter coupling, better prediction, than with generic, non-custom kernel functions, and for extracting the most out of the materials or manufacturing data ingested.

12. A method for predictive analytics, one that incorporates a prediction step, for the purpose of efficiently searching composition space of alloys or composites of interest, and hence for accelerating design or manufacturing of alloys or composites with desired material characteristics, a method utilizing a database importing step, for ingesting materials or manufacturing data, an optional preprocessing step, for unified comparison of materials or manufacturing data across data sets, an optional feature selection step, for extracting the features primarily impacting the material properties of interest, a prediction step, for predicting material properties or manufacturing parameters of interest, along with a corresponding composition or composition range, given the materials or manufacturing data ingested, where the prediction step employs a prediction technique, where the prediction step combines physics-based models, or analytical models, specific to alloys or composites of interest, with traditional black-box prediction models, for improved prediction accuracy, and where the prediction technique employed can involve regression analysis, with relatively few unknown model parameters, when limited data is available, but a machine learning predictor, with relatively many unknown model parameters, when a sufficiently large data set is available, where the prediction technique is selected such that at least one data point is available for each unknown prediction model parameter, and a reporting and evaluation step, for reporting or evaluating the materials properties or manufacturing parameters of interest.

13. A method according to claim 12, where the data importing step employs an Export, Transform and Load operation for importing data from a source into the destination predictive analytics system, when the destination system represents the data differently from the source.

14. A method according to claim 12, where the preprocessing step applies a normalization step for standardizing the input data, and where the standardization involves division of endurance limit with tensile strength, in case of prediction of fatigue behavior of alloys or composites of interest.

15. A method according to claim 12, where the feature selection step utilizes features related to composition or microstructure of the alloy or composite of interest, process, heat treatment, temperature, environment, testing mode or loading rate.

16. A method according to claim 12, where the prediction step is capable of accommodating models capturing physical dependencies, referred to as physics-based models, as a priori information, and correspondingly constructing dependencies within the prediction model, for the purpose of expediting training or improving prediction accuracy.

17. A method according to claim 16, where the physics-based models involve thermodynamics, first principle, empirical rules or mesoscale models, or in case of prediction of fatigue life, models for dislocation dynamics or slip band information.

18. A method according to claim 12, where the prediction step consists of an optional "forward" prediction step along with an optional "inverse" prediction step, where the "forward" prediction step is responsible for predicting the material properties or manufacturing parameters of interest from source characteristics, where the "inverse" prediction step is responsible for inferring source characteristics, in particular alloy composition, from source characteristics from material properties targeted, and where the source characteristics can consist of composition, microstructure, process, heat treatment, temperature, environment, testing mode or loading rate.

19. A method according to claim 12, where the feature selection step employs canonical component analysis or regression analysis, for purpose of selecting features capable of distinguishing between calcium-magnesium-alumino-silicate and calcium sulfate hot corrosion attacks, with or without influence of sea salt, in order to develop coatings resistant to calcium-magnesium-alumino-silicate and calcium sulfate hot corrosion.

20. A method according to claim 16, where the physics-based models involve thermodynamics, first principle, empirical rules or mesoscale models, or in case of prediction of fatigue life, models for dislocation dynamics or slip band information.

21. A method according to claim 12, where the prediction step supports inverse design representations.

* * * * *